United States Patent [19]

Hirai et al.

[11] Patent Number: 5,120,746
[45] Date of Patent: Jun. 9, 1992

[54] AMINE DERIVATIVES, SALTS THEREOF, PROCESS FOR PREPARING THE SAME AND AN ANTI-ULCER AGENT CONTAINING THE SAME

[75] Inventors: Shiro Hirai, Toyama; Hiroshi Hirano, Oyabe; Hirotoshi Arai, Toyama; Yasuo Kiba, Toyama; Hisanari Shibata, Toyama; Yoshikazu Kusayanag, Toyama; Minako Yotsuji, Toyama; Kazuhiko Hashiba, Toyama; Kikuko Tanada, Takaoka, all of Japan

[73] Assignee: Toyama Chemical Co., Ltd., Tokyo, Japan

[21] Appl. No.: 490,056

[22] Filed: Mar. 30, 1990

Related U.S. Application Data

[62] Division of Ser. No. 919,716, Oct. 16, 1986, Pat. No. 4,923,882, which is a division of Ser. No. 550,933, Nov. 14, 1983, Pat. No. 4,643,849.

[30] Foreign Application Priority Data

Nov. 12, 1982 [JP] Japan .................... 57-198434
Nov. 4, 1983 [JP] Japan .................... 58-205925

[51] Int. Cl.⁵ .................... A61K 31/445; C07D 409/00
[52] U.S. Cl. .................... 514/326; 514/331; 514/336; 514/343; 514/355; 514/422; 514/438; 514/459; 514/461; 546/212; 546/213; 546/214; 546/231; 546/315; 546/162; 546/14; 548/517; 548/527; 548/566; 548/567; 549/75; 549/76; 549/414; 549/419; 549/494
[58] Field of Search .................... 549/75, 76, 494, 4; 546/162, 246, 247, 315, 14, 212, 214, 229; 564/17, 32; 548/517, 527, 566, 567; 514/326, 331, 422, 438, 459, 461, 536, 343, 355

[56] References Cited

U.S. PATENT DOCUMENTS

4,233,302 11/1980 Martin-Smith .................... 546/212
4,304,780 12/1981 Martin-Smith .................... 546/212
4,500,529 2/1985 Shanklin et al. .................... 564/17

Primary Examiner—C. Warren Ivy
Assistant Examiner—Celia Chang
Attorney, Agent, or Firm—Oblon, Spivak, McClelland, Maier & Neustadt

[57] ABSTRACT

This invention relates to amine derivatives and salts thereof. These compounds have an anti-ulcer activity which is effective to human beings and animals. This disclosure relates to such compound, a process for the preparation thereof and an anti-ulcer agent containing the same.

18 Claims, No Drawings

AMINE DERIVATIVES, SALTS THEREOF, PROCESS FOR PREPARING THE SAME AND AN ANTI-ULCER AGENT CONTAINING THE SAME

This application is a divisional of application Ser. No. 06/919,716 filed Oct. 16, 1986 now U.S. Pat. No. 4,923,882 which in turn is a divisional of application Ser. No. 06/550,933 filed Nov. 14, 1983, now U.S. Pat. No. 4,643,849.

This invention relates to a novel amine derivative, a salt thereof, a process for preparing the same and an anti-ulcer agent containing the same.

The compounds of this invention have excellent inhibitory activity on gastric acid secretion, antiulcer activity and improving activity of gastric mucosal blood flow. They have a long duration of the activity and exhibit the effects at a low dose. Therefore safety margins of them are very wide.

It has heretofore been known that compounds having a histamine $H_2$-blocking effect are useful for treating peptic ulcer. The present inventors have devoted themselves to research on compounds which block a histamine $H_2$ recepter, and have consequently found that amine derivatives represented by the hereinafter described general formula (I) and salts thereof have an excellent anti-ulcer activity.

The compounds of this invention are characterized by having

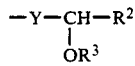

in the molecule.

An object of this invention is to provide a novel amine derivative having

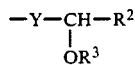

in the molecule and a salt thereof.

Another object of this invention is to provide a novel amine derivative and a salt thereof which have an anti-ulcer activity.

A further object of this invention is to provide a process for producing a novel amine derivative or a salt thereof.

A still further object of this invention is to provide a pharmaceutical composition containing a novel amine derivative or a salt thereof as an active ingredient.

A still further object of this invention is to provide a method for treating peptic ulcer.

Other objects and advantages of this invention will become apparent from the following description.

The compounds of this invention are amine derivatives represented by the following formula (I) and salts thereof:

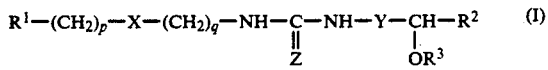

wherein each of $R^1$ and $R^2$, which may be the same or different, is a substituted or unsubstituted aryl or heterocyclic group; p is 0, 1, 2 or 3; X is an oxygen or sulfur atom; q is 2, 3 or 4; Z is an oxygen or sulfur atom, $NR^4$ ($R^4$ is a hydrogen atom, a cyano group, a hydroxyl group, a nitro group, an alkyl group, an alkenyl group, an alkoxy group, a substituted or unsubstituted acyl group, a substituted or unsubstituted aryl group, a carbamoyl group, a sulfamoyl group, an alkoxycarbonyl group, an alkylsulfonyl group, a substituted or unsubstituted arylsulfonyl group, a substituted or unsubstituted aryloxy group, a substituted or unsubstituted acylamino group, an alkoxycarbonylamino group, or a carboxyalkylamino group), or $CHR^5$ ($R^5$ is a nitro group, a substituted or unsubstituted acyl group, a substituted or unsubstituted aryl group, an alkylsulfonyl group or a substituted or unsubstituted arylsulfonyl group); Y is an alkylene group, and $R^3$ is a hydrogen atom or a hydroxylprotecting group.

In the present specification unless otherwise specified, the term "alkyl group" means a $C_{1-8}$alkyl group such as methyl, ethyl, n-propyl, isopropyl, n-butyl, isobutyl, sec-butyl, pentyl, hexyl, octyl or the like; the term "alkenyl group" means a $C_{2-4}$alkenyl group such as vinyl, allyl, isopropenyl, butenyl or the like; the term "cycloalkyl group" means a $C_{3-7}$cycloalkyl group such as cyclopropyl, cyclobutyl, cyclopentyl, cyclohexyl, cycloheptyl or the like; the term "alkoxy group" means a $C_{1-4}$alkoxy group such as methoxy, ethoxy, n-propoxy, isopropoxy, n-butoxy or the like; the term "alkenyloxy group" means a $C_{2-4}$alkenyloxy group such as vinyloxy, alloyloxy, isopropenyloxy, butenyloxy or the like; the term "alkylthio group" means a $C_{1-4}$alkylthio group such as methylthio, ethylthio, n-propylthio, isopropylthio, n-butylthio or the like; the term "alkylsulfinyl group" means a $C_{1-4}$alkylsulfinyl group such as methylsulfinyl, ethylsulfinyl or the like; the term "hydroxyalkyl group" means a hydroxy-$C_{1-4}$alkyl group such as hydroxymethyl, 1-hydroxyethyl, 2-hydroxyethyl, 3-hydroxypropyl, 4-hydroxybutyl or the like; the term "alkoxyalkyl group" means a $C_{1-4}$alkoxy-$C_{1-4}$alkyl group such as methoxymethyl, ethoxymethyl, 2-methoxyethyl, 3-methoxypropyl or the like; the term "halogenoalkyl group" means a halogeno-$C_{1-4}$-alkyl group such as chloromethyl, bromomethyl, dichloromethyl, dibromomethyl, trifluoromethyl or the like; the term "alkylamino group" means a $C_{1-4}$alkylamino group such as methylamino, ethylamino, n-propylamino, n-butylamino or the like; the term "dialkylamino group" means a di-$C_{1-4}$alkylamino group such as dimethylamino, ethylmethylamino, diethylamino, di-n-butylamino or the like; the term "acyl group" means a formyl group, a $C_{2-5}$-alkanoyl group such as acetyl, propionyl, isovaleryl, pivaloyl or the like, a $C_{5-8}$cycloalkanecarbonyl group such as cyclopentylcarbonyl, cyclohexylcarbonyl or the like, an aroyl group such as benzoyl, toluoyl, 2-naphthoyl or the like, and a heterocyclic carbonyl group such as 2-thenoyl, 3-furoyl, nicotinoyl or the like; the term "acyloxy group" means the above-mentioned acyl group bonded to an oxygen atom; the term "aryl group" means a group derived from an aromatic hydrocarbon such as phenyl, naphthyl, indanyl or the like; the term "aralkyl group" means an ar-$C_{1-4}$alkyl group such as benzyl, phenethyl, naphthylmethyl or the like; the term "acyloxyalkyl group" means the above-mentioned acyl group bonded to the abovementioned hydroxyalkyl group; the term "carbamoyl group" means $NH_2CO-$, a $C_{1-4}$alkylaminocarbonyl group such as methylaminocarbonyl, ethylaminocarbonyl, propylaminocarbonyl or the like, and a di-$C_{1-4}$alkylaminocarbonyl group such as dimethylaminocarbonyl, diethylaminocarbonyl or the like;

the term "sulfamoyl group" means NH₂SO₂—, a C₁₋₄alkylaminosulfonyl group such as methylaminosulfonyl, ethylaminosulfonyl, propylaminosulfonyl or the like, and a di-C₁₋₄alkylaminosulfonyl group such as dimethylaminosulfonyl, diethylaminosulfonyl or the like; the term "alkylsulfonyl group" means a C₁₋₄alkylsulfonyl group such as methanesulfonyl, ethanesulfonyl or the like; the term "arylsulfonyl group" means an arylsulfonyl group such as benzenesulfonyl, naphthalenesulfonyl or the like; the term "acylamino group" means an acylamino group in which the acyl group is the same as mentioned above; the term "aryloxy group" means phenyloxy, naphthyloxy or the like; and the term "halogen atom" means fluoro, chloro, bromo, iodo, or the like.

Each of $R^1$ and $R^2$ in the general formula (I), which may be the same or different, represent a substituted or unsubstituted aryl or heterocyclic group, and the heterocyclic group includes, for example, heterocyclic groups containing at least one hetero atom selected from nitrogen, sulfur and oxygen atoms in the ring such as thienyl, furyl, pyrrolyl, imidazolyl, pyrazolyl, thiazolyl, isothiazolyl, oxazolyl, isoxazolyl, thiazolidinyl, oxazolidinyl, 1,3,4-thiadiazolyl, 1,2,4-triazolyl, pyridyl, pyrimidinyl, pyrazinyl, pyridazinyl, benzofuranyl, benzothienyl, benzoimidazolyl, 1,4-benzodioxanyl and the like. The aryl and heterocyclic groups for $R^1$ and $R^2$ may be substituted by at least one substituent such as a halogen atom; a hydroxyl group; a nitro group; an oxo group; a cyano group; a carboxyl group; a carbamoyl group; a mercapto group; an amino group; an alkyl group; an alkenyl group; an alkoxy group; an alkylthio group; an alkylsulfinyl group; an alkylsulfonyl group; an alkylthioalkyl group such as methylthiomethyl, ethylthiomethyl, methylthioethyl or the like; a S-oxide derivative of the alkylthioalkyl group; a hydroxyalkyl group; an alkenyloxy group; an alkoxyalkyl group; a hydroxyalkyloxy group such as 2-hydroxyethoxy, 3-hydroxypropoxy or the like; a halogenoalkyl group; an alkylamino group; a dialkylamino group; an acyl group; an acyloxy group; an acyloxyalkyl group; an alkylenedioxy group in which the oxygen atoms are linked to the adjacent carbon atoms such as methylenedioxy, ethylenedioxy, trimethylenedioxy or the like; a cycloalkyl group; an aryl group; an aralkyl group; an acylamino group; the formula

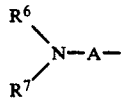

($R^6$ and $R^7$, which may be the same or different, represent hydrogen atoms, alkyl groups, cycloalkyl groups, alkenyl groups, aralkyl groups, hydroxyl groups, halogenoalkyl groups, hydroxyalkyl groups, alkoxyalkyl groups, amino-C₁₋₄alkyl groups such as 2-aminoethyl, 3-aminopropyl or the like, C₁₋₄alkylamino-C₁₋₄alkyl groups such as methylaminomethyl, 2-methylaminoethyl or the like, or di-C₁₋₄alkylamino-C₁₋₄alkyl groups such as dimethylaminomethyl, 2-dimethylaminoethyl or the like, or $R^6$ and $R^7$, when taken with the nitrogen atom to which they are bonded, form a saturated heterocyclic group; and A is an alkylene group such as methylene, ethylene, propylene, trimethylene, tetramethylene or the like), or the formula

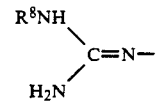

($R^8$ is a hydrogen atom, an alkyl group, a halogenoalkyl group or an acyl group).

Among these substituents, the saturated heterocyclic group which $R^6$ and $R^7$ form when taken with the nitrogen atom to which they are bonded, includes, for example, nitrogen-containing saturated heterocyclic groups which may further contain a hetero atom selected from nitrogen, sulfur and oxygen atoms in the ring such as 1-pyrrolidinyl, piperidino, morpholino, thiomorpholino, 1-hexamethyleneimino, 1-piperazinyl, 4-methyl-1-piperazinyl, 3-hydroxy-1-pyrrolidinyl, 3-hydroxymethyl-1-pyrrolidinyl, 2-hydroxymethyl-1-pyrrolidinyl, 3-hydroxy-1-piperidinyl, 4-hydroxy-1-p-piperidinyl, 3-hydroxymethyl-1-piperidinyl, 4-hydroxymethyl-1-piperidinyl and the like.

Z represents an oxygen atom, a sulfur atom, $NR^4$ or $CHR^5$, in which $R^4$ represents a hydrogen atom; a cyano group; a hydroxyl group; a nitro group; an alkyl group; an alkenyl group; an alkoxy group; a substituted or unsubstituted acyl group; a substituted or unsubstituted aryl group; a carbamoyl group; a sulfamoyl group; an alkoxycarbonyl group, for example, a C₁₋₄alkoxycarbonyl group such as methoxycarbonyl, ethoxycarbonyl, propoxycarbonyl or the like; an alkylsulfonyl group; a substituted or unsubstituted arylsulfonyl group; a substituted or unsubstituted aryloxy group; a substituted or unsubstituted acylamino group; an alkoxycarbonylamino group, for example, a C₁₋₄alkoxycarbonylamino group such as methoxycarbonylamino, ethoxycarbonylamino, n-butoxycarbonylamino or the like; a carboxyalkylamino group, for example, a carboxy-C₁₋₄alkylamino group such as carboxymethylamino, 2-carboxyethylamino or the like, and $R^5$ represents a nitro group, a substituted or unsubstituted acyl group; a substituted or unsubstituted aryl group; an alkylsulfonyl group or a substituted or unsubstituted arylsulfonyl group.

The substituents for $R^4$ and $R^5$ include alkyl groups, halogenoalkyl groups, alkoxy groups, halogen atoms and the like.

Y is an alkylene group, which includes, for example, C₁₋₄alkylene groups such as methylene, ethylene, propylene, trimethylene, tetramethylene and the like.

$R^3$ represents a hydrogen atom or a hydroxylprotecting group. The hydroxyl-protecting group includes, for example, acyl groups; a substituted or unsubstituted alkoxycarbonyl groups such as 1,1-dimethylpropoxycarbonyl, tert.-butoxycarbonyl, isopropoxycarbonyl, 2,2,2-trichloroethoxycarbonyl, ethoxycarbonyl, 2,2,2-tribromoethoxycarbonyl and the like; a substituted or unsubstituted aralkyloxycarbonyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)-benzyloxycarbonyl, 4-(4-methoxyphenylazo)benzyloxycarbonyl and the like; halogenoalkanoyl groups such as monochloroacetyl, trifluoroacetyl and the like; 2-furyloxycarbonyl group; 1-adamantyloxycarbonyl group; 8-quinolyloxycarbonyl group; benzyl group; diphenylmethyl group; trityl group; alkyl groups; methoxymethyl group; tetrahydrofuryl group; tetrahydropyranyl group; 2-nitrophenylthio group; 2,4-dinitrophenylthio group; organic silyl-containing groups such as trimethylsilyl, tert.-butyldimethylsilyl and the like; etc.

The salts of the compound represented by the general formula (I) include, for example, salts with inorganic acids such as hydrochloric acid, hydrobromic acid, sulfuric acid, phosphoric acid and the like; salts with organic acids such as acetic acid, propionic acid, oxalic acid, citric acid, lactic acid, maleic acid, succinic acid, tartaric acid, mandelic acid, p-toluenesulfonic acid, picric acid, sulfamic acid and the like; salts with alkali metals such as sodium, potassium and the like; salts with alkaline earth metals such as calcium, magnesium and the like; and salts with nitrogencontaining organic bases such as procaine, N-benzyl-$\beta$-phenethylamine, 1-ephenamine, N,N-dibenzylethylenediamine, triethylemine, N-methylpiperidine and the like.

The amine derivatives of the general formula (I) and their salts of this invention include their isomers such as geometrical isomers, tautomers, optical isomers, and racemic isomers, and further include all of their crystal forms and hydrates.

Preferable compounds among the above-mentioned amine derivatives of the general formula (I) and their salts of this invention are, for example, compounds in which $R^1$ and $R^2$ are independently groups selected from substituted or unsubstituted phenyl, indanyl, thienyl, furyl, pyridyl, thiazolyl and imidazolyl groups and compounds in which Z is an oxygen atom, a nitromethylene group, an alkylsulfonylimino group, or a substituted or unsubstituted arylsulfonylimino group, a cyanoimino group, or a sulfamoylimino group.

More preferably, there are exemplified compounds represented by the following formulas (Ia), (Ib) and (Ic) and salts thereof:

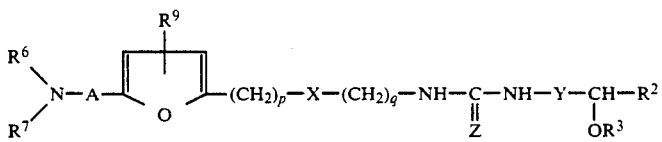
(Ia)

wherein $R^9$ is a hydrogen atom or an alkyl group, and $R^2$, $R^3$, $R^6$, $R^7$, A, p, q, X, Y and Z have the same meanings as defined above,

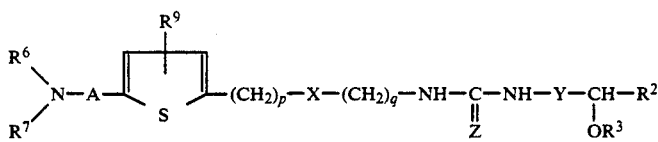
(Ib)

wherein $R^2$, $R^3$, $R^6$, $R^7$, $R^9$, A, p, q, X, Y and Z have the same meanings as defined above,

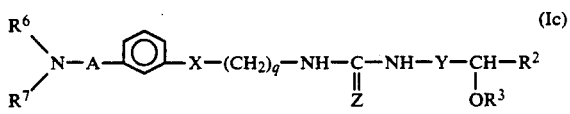
(Ic)

wherein $R^2$, $R^3$, $R^6$, $R^7$, A, q, X, Y and Z have the same meanings as defined above.

Among these compounds of the formulas (Ia) to (Ic), more preferable are those compounds in which $R^6$ and $R^7$ are independently alkyl groups, or $R^6$ and $R^7$ form a saturated heterocyclic group when taken with the nitrogen atom to which they are bonded; those compounds in which p is 1 and q is 2 or 3; those compounds in which Z is $NR^{4a}$ ($R^{4a}$ is a cyano group or an alkylsulfonyl group) or a nitromethylene group ($CHNO_2$); and those compounds in which Y is methylene and $R^2$ is a substituted or unsubstituted phenyl, indanyl, thienyl, furyl or pyridyl group.

According to this invention, there can be obtained a highly safe compound which exhibits an excellent inhibitory activity on gastric acid secretion, an excellent anti-ulcer activity and improving activity of gastric mucosal blood flow when administered orally or parenterally, and retains these activities for a long time.

Next, the pharmacological effects of typical compounds of the amine derivative of the formula (I) and the salt thereof are described below.

[I] Inhibitory effect on gastric acid secretion i) Perfused stomach preparation of anesthetized rat [according to M. N. Ghosh and H. O. Schild: Brit. J. Pharmacol. 13, 54 (1958)]

Wistar strain rats (male, 200 to 250 g) starved for 18 hours were anesthetized with urethane and then subjected to laparotomy, after which the forestomach region of the stomach of each rat was incised. The whole interior of the stomach was sufficiently washed with physiological saline, and the cut edges were sutured. A silicon tube was inserted into the stomach to a length of about 5 mm from the duodenum side and fixed. Subsequently, the stomach was perfused with physiological saline adjusted to a pH of about 10 with an aqueous sodium hydroxide solution at a constant rate (1 ml/min) through an oral sonde, and the change in pH of the perfusate which had flowed out through the silicone tube was continuously recorded. During the perfusion, histamine (30 $\mu$g/kg/min) was continuously injected, as an agent for stimulating gastric acid secretion, through the femoral vein at a rate of 0.3 ml/min. Each drug was intravenously administered when the acid secretion became almost constant (pH 3.3$\pm$0.2), and cumulatively administered when the inhibition of acid secretion at each dose reached a plateau.

A period from the time at which the acid secretion was almost completely inhibited by the cumulative administration of the drug and the pH of the perfusate which had flowed out became about the same as that before the histamine administration to the time at which the pH became 4 was defined as duration of the activity. The number of experiments was three for each dose.

The results are shown in Table 1.

TABLE 1

| Drug No. | Dose for complete inhibition (mg/kg) | Duration (min) |
| --- | --- | --- |
| 1 | 0.30 | >210 |

TABLE 1-continued

|   |   |   |
|---|---|---|
| 2 | 0.10 | >160 |
| 3 | 0.10 | 155 |
| 4 | 0.04 | 220 |
| 5 | 0.10 | 192 |
| 6 | 0.10 | 132 |
| 7 | 0.10 | 227 |
| 8 | 0.30 | 200 |
| 9 | 0.20 | 190 |
| 10 | 0.18 | 175 |
| 11 | 0.05 | 123 |
| 12 | 0.15 | >240 |
| 13 | 0.10 | >240 |
| 14 | 0.15 | 158 |
| 15 | 0.06 | 180 |
| 16 | 0.10 | 304 |
| 17 | 0.15 | >280 |
| 18 | 0.30 | 247 |
| 19 | 0.10 | 164 |
| 20 | 0.20 | >210 |
| 21 | 0.10 | >240 |
| 22 | 0.04 | 136 |
| 23 | 0.15 | 242 |
| 24 | 0.20 | >240 |
| 25 | 0.10 | >240 |
| 26 | 0.30 | >240 |
| 27 | 0.30 | >210 |
| 28 | 0.10 | 205 |
| 29 | 0.30 | >177 |
| 30 | 0.15 | >240 |
| 31 | 0.30 | 226 |
| 32 | 0.30 | >220 |
| 33 | 0.30 | >240 |
| Cimetidine | 3.00 | 16 |
| Ranitidine | 0.50 | 92 |

Drugs:
1. N-cyano-N'-{2-[(2-guanidino-4-thiazolyl)-methylthio]ethyl}-N''-(β-hydroxyphenethyl)guanidine
2. N-{2[2-guanidino-4-thiazolyl)methylthio]-ethyl}-N'-(β-hydroxyphenethyl)-2-nitro-1,1-ethenediamine
3. N-{2-[[5-(dimethylamino)methyl-2-furyl]methyl-thio]ethyl}-N'-[2-hydroxy-2-(4-hydroxyphenyl)ethyl]-2-nitro-1,1-ethenediamine
4. N-{2-[[5-(dimethylamino)methyl-2-furyl]methyl-thio]ethyl}-N'-[2-(2-fluorophenyl)-2-hydroxyethyl]-2-nitro-1,1-ethenediamine
5. N-[2-(4-chlorophenyl)-2-hydroxyethyl]-N'-{2-[[5-(dimethylamino)methyl-2-furyl]methylthio]ethyl}-2-nitro-1,1-ethenediamine
6. N-{2-[[5-dimethylamino)methyl-2-furyl]methyl-thio]ethyl}-N'-[2-hydroxy-2-(2-thienyl)ethyl]-2-nitro-1,1-ethenediamine
7. N-{2-[[5-(dimethylamino)methyl-2-furyl]methyl-thio]ethyl}-N'-[2-hydroxy-2-(3-methyl-2-thienyl)ethyl]-2-nitro-1,1-ethenediamine
8. N-{2-[[5-(dimethylamino)methyl-2-furyl]methyl-thio]ethyl}-N'-[2-hydroxy-2-(3-pyridyl)ethyl]-2-nitro-1,1-ethenediamine
9. N-{2-[[5-(dimethylamino)methyl-4-methyl-2-thienyl]methylthio]ethyl}-N'-[2-hydroxy-2-(3-methoxyphenyl)ethyl]-2-nitro-1,1-ethenediamine
10. N-{2-[[5-(dimethylamino)methyl-4-methyl-2-thienyl]methylthio]ethyl}-N'-[2-hydroxy-2-(4-hydroxyphenyl)ethyl]-2-nitro-1,1-ethenediamine
11. N-(β-hydroxyphenethyl)-2-nitro-N'-[3-(3-piperidinomethylphenoxy)propyl]-1,1-ethenediamine
12. N-[2-hydroxy-2-(4-hydroxyphenyl)ethyl]-2-nitro-N'-[3-(3-piperidinomethylphenoxy)propyl]-1,1-ethenediamine
13. N-[2-hydroxy-2-(3-hydroxyphenyl)ethyl]-2-nitro-N'-[3-(3-piperidinomethylphenoxy)propyl]-1,1-ethenediamine
14. N-[2-hydroxy-2-(4-methoxyphenyl)ethyl]-2-nitro-N'-[3-(3-piperidinomethylphenoxy)propyl]-1,1-ethenediamine
15. N-[2-(4-fluorophenyl)-2-hydroxyethyl]-2-nitro-N'-[3-(3-piperidinomethylphenoxy)propyl]-1,1-ethenediamine
16. N-[2-(4-chlorophenyl)-2-hydroxyethyl]-2-nitro-N'-[3-(3-piperidinomethylphenoxy)propyl]-1,1-ethenediamine
17. N-[2-hydroxy-2-(3,4-methylenedioxyphenyl)-ethyl]-2-nitro-N'-[3-(3-piperidinomethylphenoxy)propyl]-1,1-ethenediamine
18. N-[2-hydroxy-2-(3-methyl-2-thienyl)ethyl]-2-nitro-N'-[3-(3-piperidinomethylphenoxy)propyl]-1,1-ethenediamine
19. N-[2-hydroxy-2-(3-pyridyl)ethyl]-2-nitro-N'-[3-(3-piperidinomethylphenoxy)propyl]-1,1-ethenediamine
20. N-[2-hydroxy-2-(4-nitrophenyl)ethyl]-2-nitro-N'-[3-(3-piperidinomethylphenoxy)propyl]-1,1-ethenediamine
21. N-(β-hydroxyphenethyl)-N'-methanesulfonyl-N''-[3-(3-piperidinomethylphenoxy)propyl]guanidine
22. N-{2-[[5-(dimethylamino)methyl-2-furyl]methyl-thio]ethyl}-N'-[S(+)-2-hydroxy-2-(4-hydroxyphenyl)ethyl]-2-nitro-1,1-ethenediamine
23. N-{2-[[5-(dimethylamino)methyl-2-furyl]methyl-thio]ethyl}-N'-[2-hydroxy-2-(3-methoxyphenyl)ethyl]-2-nitro-1,1-ethenediamine
24. N-{2-[[5-(dimethylamino)methyl-2-furyl]methyl-thio]ethyl}-N'-[2-hydroxy-2-(4-methylthiophenyl)ethyl]-2-nitro-1,1-ethenediamine
25. N-{2-[[5-(dimethylamino)methyl-2-furyl]methyl-thio]ethyl}-N'-[2-(3,4-difluorophenyl)-2-hydroxyethyl]-2-nitro-1,1-ethenediamine
26. N-[2-hydroxy-2-(4-methylthiophenyl)ethyl]-2-nitro-N'-[3-(3-piperidinomethylphenoxy)propyl]-1,1-ethenediamine
27. N-[2-hydroxy-2-(3-trifluoromethylphenyl)-ethyl]-2-nitro-N'-[3-(3-piperidinomethylphenoxy)propyl]-1,1-ethenediamine
28. N-[2-(3-chlorophenyl)-2-hydroxyethyl]-N'-{2-[[5-(dimethylamino)methyl-4-methyl-2-thienyl]methyl-thio]ethyl}-2-nitro-1,1-ethenediamine
29. N-{2-[[5-(dimethylamino)methyl-4-methyl-2-thienyl]methylthio]ethyl}-N'-[2-hydroxy-2-(3-methyl-phenyl)ethyl]-2-nitro-1,1-ethenediamine
30. N-[2-(3,4-difluorophenyl)-2-hydroxyethyl]-2-nitro-N'-[3-(3-piperidinomethylphenoxy)propyl]-1,1-ethenediamine
31. N-{2-[[5-(dimethylamino)methyl-4-methyl-2-thienyl]methylthio]ethyl}-N'-[2-(3-ethylphenyl)-2-hydroxyethyl]-2-nitro-1,1-ethenediamine
32. N-[2-(3-bromophenyl)-2-hydroxyethyl]-N'-{2-[[5-(dimethylamino)methyl-4-methyl-2-thienyl]methylthio]-ethyl}-2-nitro-1.1-ethenediamine
33. N-{2-[[5-(dimethylamino)methyl-4-methyl-2-thienyl]methylthio]ethyl}-N'-[2-(3-trifluoro-methylphenyl)ethyl]-2-nitro-1,1-ethenediamine Cimetidine: 1-Cyano-2-methyl-3-{2-(5-methyl-4-imidazolyl)-methylthioethyl}guanidine
Ranitidine: N-{2-[5-(dimethylamino)methyl-2-furyl]-methylthioethyl}-N'-methyl-2-nitro-1,1-ethenediamine ii) Pylorus ligation method
[according to H. Shay et al: Gastroenterology, 5, 43 (1945)]

Five to six Wistar strain rats (male, 190 to 230 g) per group were starved for 35 hours, after which each drug was orally administered, and after 2 hours, the pylorus of each rat was ligated under ether anesthesia. Subsequently, the abdominal wall was sutured, immediately after which histamine was administered subcutaneously on the back at a dose of 25 mg/kg. After 3 hours, each rat was killed, after which the cardiac portion was ligated, and the atomach was removed. After 1 ml of distilled water was injected into the stomach, the gastric juice was collected by centrifugation and its volume was measured. The acidity of the gastric juice was measured by titrating 1 ml of the gastric juice with a 0.1 N aqueous sodium hydroxide solution, taking pH 7.0 as the end-point. Physiological saline was administered to a control group.

The inhibition percentage of gastric acid secretion was determined from the following equation:

Inhigition percentage of gastric acid secretion (%) =

-continued $$\frac{\left(\begin{array}{c}\text{Acid output of}\\ \text{control group}\end{array}\right) - \left(\begin{array}{c}\text{Acid output of}\\ \text{drug-treated group}\end{array}\right)}{\text{Acid output of control group}} \times 100$$

The results are shown in Table 2.

TABLE 2

| Drug No. | Dose (mg/kg) | Inhibition percentage (%) |
|---|---|---|
| 3 | 3 | 82** |
|   | 1 | 75* |
| 4 | 3 | 75** |
| 5 | 3 | 80* |
| 6 | 10 | 93** |
|   | 3 | 67* |
| 7 | 3 | 88* |
| 9 | 1 | 75* |
| 11 | 10 | 81** |
|   | 3 | 79** |
| 12 | 3 | 87** |
| 13 | 1 | 51* |
| 14 | 1 | 61* |
| 15 | 1 | 77* |
| 16 | 3 | 89* |
| 17 | 3 | 70** |
| 18 | 3 | 87** |
| 29 | 1 | 56* |
| 32 | 1.5 | 60* |
| 33 | 1 | 55** |
| 34 | 3 | 71* |
| 35 | 1 | 47* |
| 36 | 3 | 85* |
| 37 | 3 | 77* |
| 38 | 1 | 41* |
| 39 | 3 | 90** |
| 40 | 10 | 85** |
|   | 3 | 75* |
| 41 | 1 | 65* |
| 42 | 1 | 57* |
| 43 | 1 | 51* |
| 44 | 1 | 75* |
| 45 | 1 | 65** |
| Cimetidine | 90 | 97** |
|   | 30 | 60* |
|   | 10 | 39 |
| Ranitidine | 30 | 91** |
|   | 10 | 56* |
|   | 3 | 17 |

Note:
*$p < 0.05$
**$p < 0.01$
Drugs:
34. N-{2-[[5-(dimethylamino)methyl-4-methyl-2-thienyl]methylthio]ethyl}-N'-[2-(2,6-difluorophenyl)-2-hydroxyethyl]-2-nitro-1,1-ethenediamine
35. N-{2-[[5-(dimethylamino)methyl-4-methyl-2-thienyl]methylthio]ethyl}-N'-[2-(2,4-difluorophenyl)-2-hydroxyethyl]-2-nitro-1,1-ethenediamine
36. N-[2-(2-fluorophenyl)-2-hydroxyethyl]-2-nitro-N'-[3-(3-piperidinomethylphenoxy)propyl]-1,1-ethenediamine
37. N-{2-[[5-(dimethylamino)methyl-2-furyl]-methylthio]ethyl}-N'-[2-hydroxy-2-(4-methoxyphenyl)-ethyl]-2-nitro-1,1-ethenediamine
38. N-{2-[[5-(dimethylamino)methyl-2-furyl]-methylthio]ethyl}-N'-[2-(4-fluorophenyl)-2-hydroxy-ethyl]-2-nitro-1,1-ethenediamine
39. N-{2-[[5-(dimethylamino)methyl-2-furyl]methyl-thio]ethyl}-N'-[2-hydroxy-2-(2-methylphenyl)ethyl]-2-nitro-1,1-ethenediamine
40. N-{2-[[5-(dimethylamino)methyl-4-methyl-2-thienyl]methylthio]ethyl}-N'-(β-hydroxyphenethyl)-2-nitro-1,1-ethenediamine
41. N-{2-[[5-(dimethylamino)methyl-4-methyl-2-thienyl]methylthio]ethyl}-N'-[2-(4-fluorophenyl)-2-hydroxyethyl]-2-nitro-1,1-ethenediamine
42. N-{2-[[5-(dimethylamino)methyl-4-methyl-2-thienyl]methylthio]ethyl}-N'-[2-(4-ethylphenyl)-2-hydroxyethyl]-2-nitro-1,1-ethenediamine
43. N-[2-(3-fluorophenyl)-2-hydroxyethyl]-2-nitro-N'-[3-(3-piperidinomethylphenoxy)propyl]-1,1-ethenediamine
44. N-[2-hydroxy-2-(2-methylphenyl)ethyl]-2-nitro-N'-[3-(3-piperidinomethylphenoxy)propyl]-1,1-ethenediamine
45. N-[2-(4-aminophenyl)-2-hydroxyethyl]-2-nitro-N'-[3-(3-piperidinomethylphenoxy)propyl]-1,1-ethenediamine

[II] Effect on isolated guinea pig atrium

Hartley guinea pig (male, 300 to 400 g) was killed by blood-letting, immediately after which the heart was isolated, and the right atrium was separated in a Krebs-Henseleit solution and used as a preparation. The preparation was suspended (load: 1 g) in a Magnus tube containing Krebs-Henseleit solution (30° C.) through which a mixed gas of 95% of $O_2$ and 5% of $CO_2$ had been bubbled, and its motion was isometrically recorded on polygraph. The preparation was trained in a bath fluid, and after the heart rate became constant, $5 \times 10^{-6}$ M of histamine was administered. After the heart rate became constant, each drug was administered cumulatively.

The inhibition percentage was determined from the following equation:

$$\text{Inhibition percentage (\%)} = \frac{HR_{max} - HR_x}{HR_{max} - HR_{min}} \times 100$$

$HR_{min}$: heart rate before the administration of histamine
$HR_{max}$: heart rate after the administration of histamine
$HR_x$: heart rate at the time of the administration of each drug.

The doses and the inhibition percentages were plotted on a logarithmic probability paper, and the 50% inhibition dose ($ID_{50}$) was determined. The number of experiments were five for each dose.

The results are shown in Table 3.

TABLE 3

| Drug No. | $ID_{50}$ (M) | Potency ratio |
|---|---|---|
| 3 | $2.28 \times 10^{-7}$ | 14.7 |
| 4 | $2.25 \times 10^{-7}$ | 14.9 |
| 9 | $2.45 \times 10^{-7}$ | 13.7 |
| 15 | $2.18 \times 10^{-7}$ | 15.4 |
| 17 | $2.18 \times 10^{-7}$ | 15.4 |
| 42 | $2.37 \times 10^{-7}$ | 14.1 |
| Cimetidine | $3.35 \times 10^{-6}$ | 1 |

[III] Anti-ulcer activity (i) Indomethacin ulcer

Six Wistar strain rats (male, 200 to 250 g) per group were starved for 24 hours, after which each drug was orally administered, and after 30 minutes, Indomethacin was injected subcutaneously at a dose of 30 mg/kg. After 5 hours, each rat was killed, and the stomach was removed and fixed with 3% formalin, after which the lengths of ulcers formed in the stomach was measured under the binocular stereoscopic microscope (10×), and the sum total of the lengths was taken as the ulcer index. To a control group was administered 0.5% Tween 80 physiological saline. The inhibition percentage was determined from the following equation:

Inhibition percentage (%) =

-continued $$\frac{\left(\begin{array}{c}\text{Ulcer index}\\\text{of control group}\end{array}\right) - \left(\begin{array}{c}\text{Ulcer index of}\\\text{drug-treated group}\end{array}\right)}{\text{Ulcer index of control group}} \times 100$$

The results are shown in Table 4.

TABLE 4

| Drug No. | Dose (mg/kg) | Inhibition percentage (%) | $ID_{50}$ (mg/kg) | Potency ratio |
|---|---|---|---|---|
| 3 | 10 | 71* | 3.40 | 8.1 |
|   | 3 | 51* | | |
|   | 1 | 20 | | |
| 9 | 10 | 97** | 0.70 | 39.3 |
|   | 3 | 85** | | |
|   | 1 | 70** | | |
|   | 0.3 | 6 | | |
| 15 | 10 | 98** | 0.40 | 68.8 |
|   | 3 | 92** | | |
|   | 1 | 88** | | |
|   | 0.3 | 37 | | |
| 29 | 1 | 57* | 0.88 | 31.3 |
|   | 0.3 | 8 | | |
| 32 | 3 | 72* | 1.81 | 15.2 |
|   | 1 | 24 | | |
| 40 | 3 | 82* | 1.30 | 21.2 |
|   | 1 | 40 | | |
| Cimetidine | 100 | 97** | 27.5 | 1 |
|   | 30 | 50 | | |
|   | 10 | 18 | | |
| Ranitidine | 30 | 98** | 15.5 | 1.8 |
|   | 10 | 18 | | |

Note:
*p < 0.05
**p < 0.01

(ii) Mepirizole-induced duodenal ulcer

A test was carried out according to the method of Okabe et al. [S. Okabe et al., Gastroenterology, 80, 1241 (1981)].

Six Wistar strain rats (male, 200 to 250 g) per group were starved for 24 hours, after which each drug was orally administered, and after 30 minutes, mepirizole was injected subcutaneously at a dose of 200 mg/kg. After 18 hours, the stomach and duodenum were removed and fixed with 3% formalin, after which the areas and depths of the ulcers formed in the duodenum were measured under the binocular stereoscopic microscope (10×). The scores were given in 7 grades depending on the areas and depths of the ulcers, and the sum total of the scores was taken as the ulcer index. The scores were given as follows:

That is to say, the score is 0 at an ulcer area of 0 to 0.2 mm², 1 at 0.2 to 1.0 mm², 2 at 1 to 3 mm², 3 at 3 to 6 mm², 4 at 6 to 10 mm², and 5 at 10 mm² or more, the ulcer in the condition immediately before perforation is scored as 6, and the ulcer which had caused perforation is scored as 7.

To a control group was administered 0.5% Tween 80 physiological saline. The inhibition percentage was determined from the following equation:

Inhibition percentage (%) =

$$\frac{\left(\begin{array}{c}\text{Ulcer index}\\\text{of control group}\end{array}\right) - \left(\begin{array}{c}\text{Ulcer index of}\\\text{drug-treated group}\end{array}\right)}{\text{Ulcer index of control group}} \times 100$$

The results are shown in Table 5.

TABLE 5

| Drug No. | Dose (mg/kg) | Inhibition percentage (%) | $ID_{50}$ (mg/kg) | Potency ratio |
|---|---|---|---|---|
| 3 | 10 | 97** | 2.9 | 55.9 |
|   | 3 | 49** | | |
|   | 1 | 12 | | |
| 9 | 10 | 93** | 4.3 | 37.7 |
|   | 3 | 33* | | |
|   | 1 | −8 | | |
| 15 | 10 | 93** | 4.5 | 36.0 |
|   | 3 | 29* | | |
|   | 1 | 2 | | |
| Cimetidine | 300$^{a)}$ | 59** | 162 | 1 |
|   | 100$^{b)}$ | 43* | | |
| Ranitidine | 100 | 78** | 32 | 5.1 |
|   | 30 | 49* | | |

Note:
$^{a)}$Four of six rats died.
$^{b)}$Two of six rats died.
*p < 0.05
**p < 0.01

(iii) Stress ulcer induced by water-immersion

An experiment was carried out according to the method of Takagi et al. [K. Takagi et al., Jap. J. Pharmacol., 18, 9 (1968)].

Six Wistar strain rats (male, 230 to 280 g) per group were starved for 24 hours, after which each drug was orally administered. After 30 minutes, the rats were placed in stress cage, immersed in water at 23° C. to the depth of xiphoid, and allowed to stand therein for 15 hours. Thereafter, the stomach of each rat was removed and then fixed with 3% formalin, after which the areas of the ulcers formed were measured under the binocular stereoscopic microscope (10×), and the sum total of the areas was taken as the ulcer index. To a control group was administered 0.5% Tween 80 physiological saline.

The inhibition percentage was determined from the following equation:

Inhibition percentage (%) =

$$\frac{\left(\begin{array}{c}\text{Ulcer index}\\\text{of control group}\end{array}\right) - \left(\begin{array}{c}\text{Ulcer index of}\\\text{drug-treated group}\end{array}\right)}{\text{Ulcer index of control group}} \times 100$$

The results are shown in Table 6.

TABLE 6

| Drug No. | Dose (mg/kg) | Inhibition percentage (%) | $ID_{50}$ (mg/kg) | Potency ratio |
|---|---|---|---|---|
| 3 | 10 | 83** | 1.72 | 9.0 |
|   | 3 | 73* | | |
|   | 1 | 12 | | |
| 9 | 10 | 86** | 1.70 | 9.1 |
|   | 3 | 66* | | |
|   | 1 | 33 | | |
| 15 | 10 | 83** | 1.35 | 11.5 |
|   | 3 | 69* | | |
|   | 1 | 42 | | |
| 29 | 3 | 78* | 1.40 | 11.1 |
|   | 1 | 37 | | |
| 33 | 3 | 75* | 1.58 | 9.8 |
|   | 1 | 32 | | |
| Cimetidine | 30 | 94** | 15.5 | 1 |
|   | 10 | 22 | | |
| Ranitidine | 10 | 80** | 6.4 | 2.4 |
|   | 3 | 7 | | |

Note:
*p < 0.05
**p < 0.01

(iv) Reserpine ulcer

An experiment was carried our according to the method of Adami et al. [E. Adami et al., Arch. int. Pharmacodyn., 147, 113 (1964)].

Ten Wistar strain rats (male, 180 to 200 g) per group were starved for 30 hours, after which each drug was orally administered, and after 1 hour, reserpine was injected subcutaneously at a dose of 10 mg/kg. After 18 hours, the stomach was removed and fixed with 3% formalin, and thereafter the lengths of the ulcers formed in the stomach were measured with callipers. The measured values were converted to the scores described below, and the sum total of the scores was taken as the ulcer index.

That is to say, 1 to 5 pin point ulcers are scored as 1, 6 or more pin point ulcers are scored as 2, ulcers of 1 mm or less in length are scored as 1, ulcers of 1 to 2 mm in length are scored as 2, ulcers of 2 to 4 mm in length are scored as 4, and ulcers of 4 mm or more in length are scored as 8.

To a control group was administered 0.5% Tween 80 physiological saline. The inhibition percentage was determined from the following equation:

Inhibition percentage (%) =

$$\frac{\left(\begin{array}{c}\text{Ulcer index}\\\text{of control group}\end{array}\right) - \left(\begin{array}{c}\text{Ulcer index of}\\\text{drug-treated group}\end{array}\right)}{\text{Ulcer index of control group}} \times 100.$$

The results are shown in Table 7.

TABLE 7

| Drug No. | Dose (mg/kg) | Inhibition percentage (%) | $ID_{50}$ (mg/kg) |
|---|---|---|---|
| 9 | 3 | 69** | 1.8 |
|  | 1 | 29 |  |
| 29 | 3 | 41** | 4.7 |
|  | 1 | 21 |  |

TABLE 7-continued

| Drug No. | Dose (mg/kg) | Inhibition percentage (%) | $ID_{50}$ (mg/kg) |
|---|---|---|---|
| 32 | 3 | 55** | 2.15 |
|  | 1 | 38 |  |
| 33 | 3 | 68* | 1.4 |
|  | 1 | 42 |  |
| 40 | 3 | 50** | 3.0 |
|  | 1 | 36* |  |
| Cimetidine | 100 | 9.7 |  |
| Ranitidine | 100 | 40 |  |
|  | 30 | 33 |  |

Note:
*p < 0.05
**p < 0.01

[IV] Acute toxicity

Each of 45 drugs was orally administered to ICR strain mice (male, 20 to 25 g), and the mice were observed until after 1 week.

The results are shown in Table 8.

TABLE 8

| Drug No. | Dose (mg/kg) | Number of died animals/ Number of animals used |
|---|---|---|
| 1–45 | 1000 | 0/5 |

From Tables 1 to 8, it is evident that the amine derivatives of the general formula (I) and the salts thereof have a potant inhibitory activity on gastric acid secretion and a long duration of the activity, have a potent anti-ulcer activity, have a low toxicity and therefore have a wide safety margin.

The process for producing an amine derivative of the general formula (I) or a salt thereof is described below.

The amine derivative of the general formula (I) or the salt thereof are produced by the production processes hereinafter described, per se well-known processes and processes according thereto.

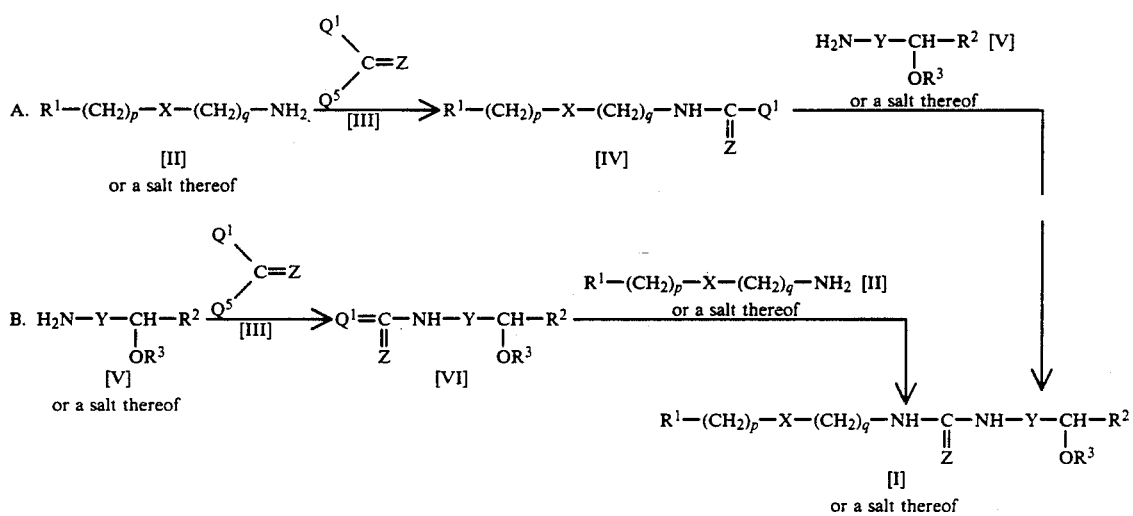

-continued

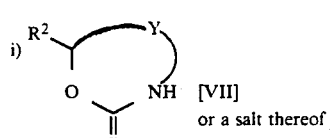

C. $R^1-(CH_2)_p-X-(CH_2)_q-NH_2$ 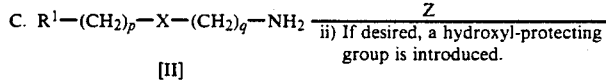

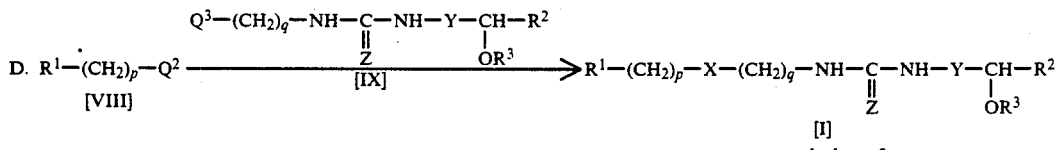

D.

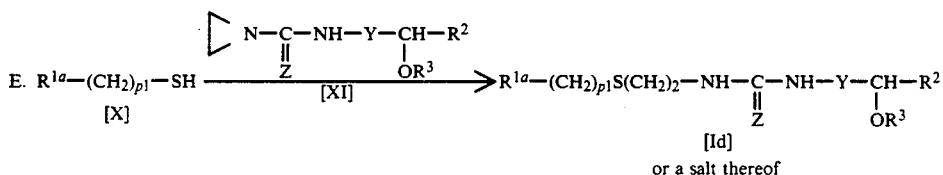

E.

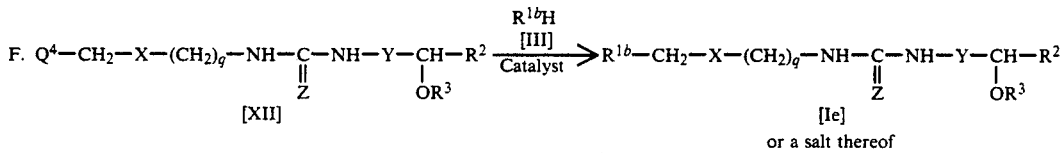

F.

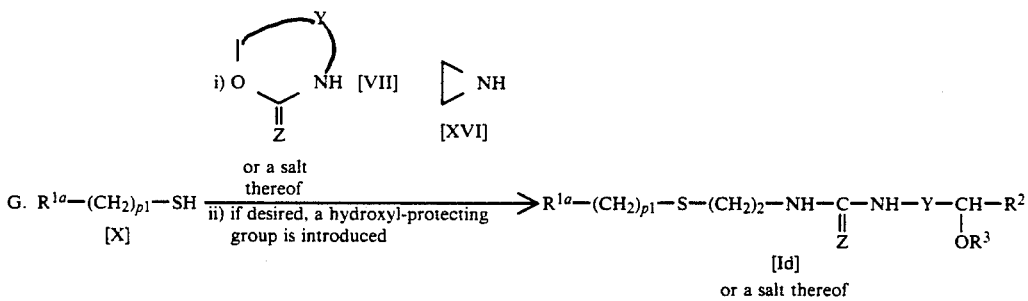

G.

In the formula, $Q^1$ and $Q^5$, which may be the same or different, are removable groups; $Q^2$ is a group which forms an oxy or thio linkage or a removable group; and in the case of p being 0, $Q^2$ is a group which forms an oxy or thio linkage; $Q^3$ is a removable group in the case of $Q^2$ being a group which forms an oxy or thio linkage, and is a group which forms an oxy or thio linkage in the case of $Q^2$ being a removable group, $R^{1a}$ is a substituted or unsubstituted heterocyclic group; $p^1$ is 1, 2 or 3; $R^{1b}$ is a substituted or unsubstituted heterocyclic group; $Q^4$ is a removable group and $R^1$, $R^2$, $R^3$, p, q, X, Y and Z have the same meanings as defined above. As the heterocyclic groups for $R^{1a}$ and $R^{1b}$, there may be used the same heterocyclic groups as described above for $R^1$, and the substituents for them include the same substituents as described for $R^1$.

Each of the production processes is described below in detail.

I) Production Processes A and B

Production Processes A and B can be carried out in substantially the same manner.

a) These production processes can be carried out by reacting a compound represented by the formula [IV] with a compound represented by the formula [V] or a salt thereof, or reacting a compound represented by the formula [VI] with a compound represented by the formula [II] or a salt thereof, in the presence or absence of a solvent.

The removable groups for $Q^1$ in the formulas [IV] and [VI] include conventional removable groups, for example, halogen atoms; alkylthio groups; aklylsulfinyl groups; aralkylthio groups such as benzylthio and the like; alkoxy groups; 1-imidazolyl group; 3,5-dimethylpyrazolyl group; etc.

The salts of the compounds of the formulas [II] and [V] include the salts exemplified in the case of the salts of the amine derivative of the general formula [I]. However, in the case of salts with acid, it is preferable to treat the salts with a suitable base, for example, an alkali metal alkoxide such as sodium methoxide or the like, an alkali hydroxide such as potassium hydroxide, sodium hydroxide or the like, or an alkali carbonate such as potassium carbonate, sodium carbonate or the like and use them in the free state.

As the solvent, any solvent may be used without any particular limitation so long as it has no adverse effect on the reaction, and there may be used alcohols such as methanol, ethanol, isopropanol, ethylene glycol and the like; nitriles such as acetonitrile, propionitrile and the like; ethers such as diethyl ether, diisopropyl ether, 1,2-dimethoxyethane, terrahydrofuran, dioxane and the like; halogenated hydrocarbons such as methylene chloride, chloroform, 1,2-dichloroethane and the like; aromatic hydrocarbons such as benzene, toluene, xylene and the like; amides such as N,N-dimethylformamide, N,N-dimethylacetamide and the like; dimethylsulfoxide; pyridine; water; etc., alone or in admixture of two or more.

Further, in effecting the reaction, it is preferable in some cases to use a base or a heavy metal salt. The base includes inorganic bases, for example, alkali hydroxides such as potassium hydroxide, sodium hydroxide and the like; alkali carbonates such as potassium carbonate, sodium carbonate and the like; and alkali hydrogencarbonates such as potassium hydrogencarbonate, sodium hydrogencarbonate and the like, or organic bases, for example, tertiary amines such as triethylamine, N-methylmorpholine, N-methylpiperidine, pyridine and the like. It is also possible to use an excess of the compound of the formula [II] or [V] to serve as the base. The heavy metal salt includes silver nitrate, lead tetraacetate, mercuric acetate and the like.

These starting compounds have geometrical isomers, tautomers, optical isomers and racemic isomers, and all of them may be used in the aforesaid processes In particular, since the compounds of the formulas [V]and [VI] have an asymmetric carbon atom in the molecule, it is preferable to use optically active forms of the compounds of the formulas [V] and [VI] when producing an optically active form of an amine derivative of the formula [I] or a salt thereof.

The amounts of the compounds of the formulas [II] and [V] or salts thereof used are preferable at least equimolar to those of the compounds of the formulas [VI] and [IV].

Although the reaction temperature and the reaction time are not critical and may properly be varied depending on the reactants and the like, the reaction is conducted preferably at $-5°$ C. to $200°$ C., more preferably $5°$ C. to $120°$ C., for 10 minutes to 48 hours.

b) The compound of the formula [IV] or [VI] can be obtained by reacting the compound of the formulas [II] or [V] or a salt thereof with a compound of the formula [III] in the presence or absence of a solvent.

$Q^1$ and $Q^5$ in the formula [III], which may be the same or different, are removable groups, and the removable group for $Q^5$ includes the same groups as described for $Q^1$ in the above-mentioned formulas [IV] and [VI].

The reaction may be effected under substantially the same conditions as in above a). However, when $R^3$ is a hydrogen atom in the reaction of a compound of the formula [V] or a salt thereof with a compound of the formula [III], it is preferably to effect the reaction at $-30°$ C. to $40°$ C., though the reaction temperature may be varied depending on the reactants.

The amount of the compound of the formula [III] used is preferable at least equimolar to the amount of the compound of the formula [II] or [V] or a salt thereof And, it is possible to use the obtained compound of the formula [IV] or [VI], as the starting compound for the subsequent reaction without isolating the same.

II) Production Process C

This production process is carried out by reacting a compound represented by the formula [II] or a salt thereof with a compound represented by the formula [VII] or a salt thereof in the presence or absence of a solvent, and then, if desired, introducing a hydroxyl-protecting group by a conventional method.

The salt of the compound of the formula [VII] includes salt with alkali metals such as potassium, sodium and the like; salts with alkaline earth metals such as calcium, magnesium and the like; and salts with tertiary amines such as triethylamine and the like.

As the solvent used in the reaction, any solvent may be used without any particular limitation so long as it has no adverse effect on the reaction Specifically, there may be exemplified the same solvents as exemplified in the production processes A and B.

The amount of the compound of the formula [VII] or the salt thereof used is preferable at least equimolar to that of the compound of the formula [II] or the salt thereof.

Although the reaction temperature and the reaction time are not critical and may properly be varied depending on the reactants and the like, the reaction is effected at preferably $-5°$ C. to $200°$ C., more preferably $20°$ C. to $120°$ C., for 10 minutes to 48 hours.

The thus obtained compound is the compound of the formula [I] in which $R^3$ is a hydrogen atom, and therefore, any of the hydroxyl-protecting groups described above may, if desired, be introduced by a conventional method to obtain a compound of the general formula [I] or a salt thereof in which $R^3$ is a hydroxylprotecting group.

III) Production Process D

This production process is carried out by reacting a compound represented by the formula [VIII] with a compound represented by the formula [IX] in the presence or absence of a solvent.

As the groups for $Q^2$ and $Q^3$ in the formulas [VIII] and [IX] which can form an oxy linkage, there may be used, for example, hydroxyl group and the like, and as those which can form a thio linkage, there may be used, for example, mercapto group, amidinothio group and the like. As the removable groups for $Q^2$ and $Q^3$, there may be used, for example, halogen atoms; acyloxy groups such as acetoxy and the like; substituted or unsubstituted arylsulfonyloxy groups, such as benzenesulfonyloxy, 4-methylbenzenesulfonyloxy and the like, etc.

As the solvent used in the reaction, any solvent may be used without any particular limitation so long as it has no adverse effect on the reaction. The solvents may be used alone or in admixture of two or more, and include, for example, slcohols such as methanol, ethanol, isopropanol, ethylene glycol and the like; ethers such as tetrahydrofuran, dioxane and the like; ketones such as acetone and the like; amides such as N,N-dimethylformamide, N,N-dimethylacetamide and the like; water; etc.

The reaction is preferably effected under basic conditions, and the bases which may be used for this purpose include inorganic bases, for example, alkali metal alkoxides such as potassium methoxide, sodium methoxide and the like; alkali hydroxides such as potassium hydroxide, sodium hydroxide and the like; alkali carbonates such as potassium carbonate, sodium carbonate and the like; alkaline earth metal hydroxides such as calcium hydroxide and the like, or organic bases, for example, tertiary amines such as triethylamine and the like; etc.

Further, this reaction is preferably effected in an inert gas atmosphere, for example, in a nitrogen gas atmosphere.

Although the reaction temperature and the reaction time are not critical and may properly be varied depending on the reactants and the like, the reaction may preferably be conducted at −20° C. to 120° C. for 10 minutes to 48 hours.

In addition, the reaction may also be effected in a two-phase system consisting of water and a solvent which is not miscible with water, for example, chloroform or the like, in the presence of a phase transfer catalyst, for example, a quaternary ammonium salt such as benzyltriethylammonium chloride or the like, and any of the above-mentioned bases.

IV) Production Process E

This production process is carried out by reacting a compound of the formula [X] with a compound of the formula [XI] in the presence or absence of a solvent.

As the solvent used in this reaction, any solvent may be used without any particular limitation so long as it has no adverse effect on the reaction, and the solvent includes ethers such as tetrahydrofuran, dioxane and the like; nitriles such as acetonitrile, propionitrile and the like; aromatic hydrocarbons such as benzene, toluene and the like; amides such as N,N-dimethylformamide, N,N-dimethylacetamide and the like; water; alcohols such as methanol, ethanol and the like; etc. which may be used alone or in admixture of two or more.

In effecting the reaction, it is preferable in some cases to use a base, which includes, for example, the bases exemplified in Production Process F.

This reaction is preferably effected in an inert gas atmosphere, for example, in a nitrogen gas atmosphere.

Although the reaction temperature and the reaction time are not critical and may be properly varied depending on the reactants and the like, the reaction is effectad at preferably −10° C. to 150° C., more preferably room temperature to 100° C., for 10 minutes to 24 hours.

And, the reaction is preferably effected for a compound [XI] in which $R^3$ is a hydroxyl-protecting group. The hydroxyl-protecting group of the thus obtained compound can be removed in a conventional manner to obtain a compound in which $R^3$ is a hydrogen atom.

V) Production Process F

This production process is carried out by reacting a compound represented by the formula [XII] with a compound represented by the formula [XIII] in the presence of a catalyst in the presence or absence of a solvent.

The removable group for $Q^4$ in the formula [XII] includes, for example, alkoxy groups, aryloxy groups, acyloxy groups and the like.

As the solvent used in the reaction, any solvent may be used without any particular limitation so long as it has no adverse effect on the reaction, and the solvent includes, for example, carboxylic acids such as acetic acid, butyric acid and the like; halogenated hydrocarbons such as methylene chloride, chloroform, 1,2-dichloroethane and the like; esters such as ethyl acetate, butyl acetate and the like; ethers such as tetrahydrofuran, dioxane and the like; etc.

The catalyst includes Lewis acids such as boron trifluoride and the like; complex compounds of Lewis acids, such as boron trifluoride-acetic acid complex compound and protonic acids such as hydrogen chloride, sulfuric acid, p-toluenesulfonic acid, trifluoroacetic acid and the like. In the present reaction, these compounds may also be used as solvents Although the reaction temperature and the reaction time are not critical and may be properly varied depending on the reactants and the like, the reaction is preferably effected at 0° C. to 50° C., for 30 minutes to 5 hours.

Next, processes for producing the starting compounds in each of the above-mentioned production processes are described below.

Production Process G

This production process is carried out by reacting a compound represented by the formula [X] with a compound represented by the formula [VII] or a salt thereof and ethyleneimine in the presence or absence of a solvent, and then, if desired, protecting the hydroxyl group.

As the solvent, any solvent may be used without any particular limitation so long as it has no adverse effect on the reaction, and there may be used alcohols such as methanol, ethanol, isopropanol, ethylene glycol and the like; nitriles such as acetonitrile, propionitrile and the like; ethers such as tetrahydrofuran, dioxane and the like; halogenated hydrocarbons such as methylene chloride, chloroform, 1,2-dichloroethane and the like; aromatic hydrocarbons such as benzene, toluene, xylene and the like; amides such as N,N-dimethylformamide, N,N-dimethylacetamide and the like; dimethylsulfoxide; water; etc., alone or in admixture of two or more.

And, in effecting the reaction, it is preferable in some cases to use a base. The base includes the same bases as described in the Production Process D.

Further, this reaction is preferably effected in an inert gas atmosphere, for example, in a nitrogen gas atmosphere.

The addition order of a compound represented by the formula [X], a compound represented by the formula [VII] or a salt thereof and ethyleneimine is not critical and may properly be determined.

Although the reaction temperature and the reaction time are not critical and may properly be varied depending on the reactants and the like, the reaction is effected at preferably −10° C. to 200° C. for 10 minutes to 48 hours.

The thus obtained compound is the compound of the formula [Id] in which $R^3$ is a hydrogen atom, and therefore, the hydroxyl-protecting group described above may, if desired, be introduced by a conventional method to obtain a compound of the formula [Id] or a salt thereof in which $R^3$ is a hydroxyl-protecting group.

The starting compounds represented by the formulas [II], [III], [V], [X] and [XIII], though include novel compounds, too, are easily produced in a manner known per se, the methods described in the Examples which appear hereinafter, and methods according thereto.

The starting compounds represented by the formulas [VII], [VIII], [IX], [XI] and [XII] are produced in the following manner:

1) Process for producing the compound of the formula [VII] (route 1)

This process is carried out by reacting a compound represented by the formula [Va] or a salt thereof with a compound represented by the formula [III] in the presence or absence of a solvent.

1.
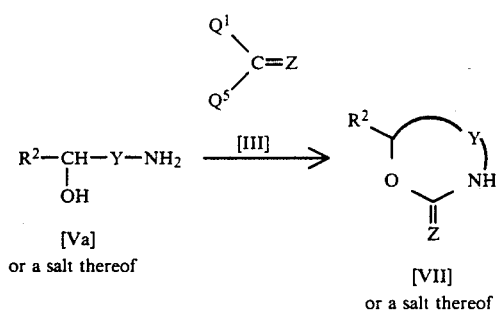
2.
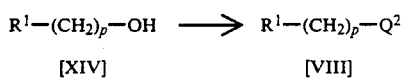
3.
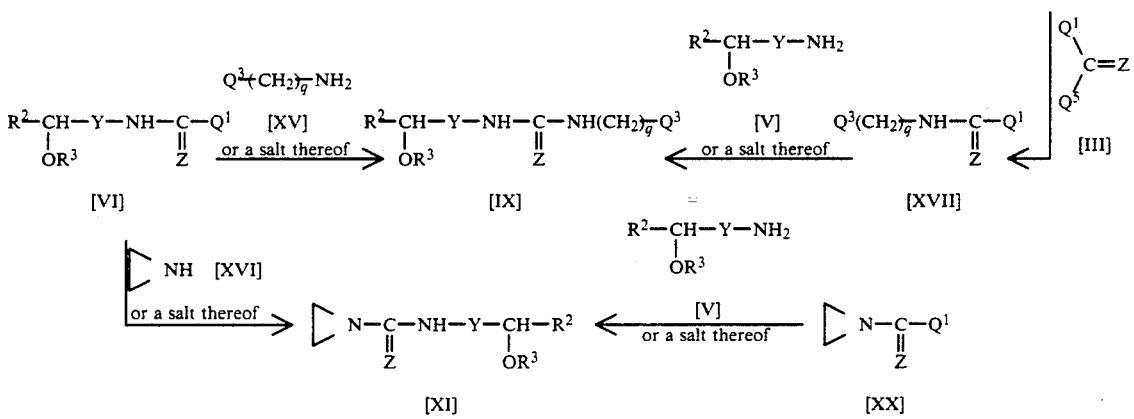
4.
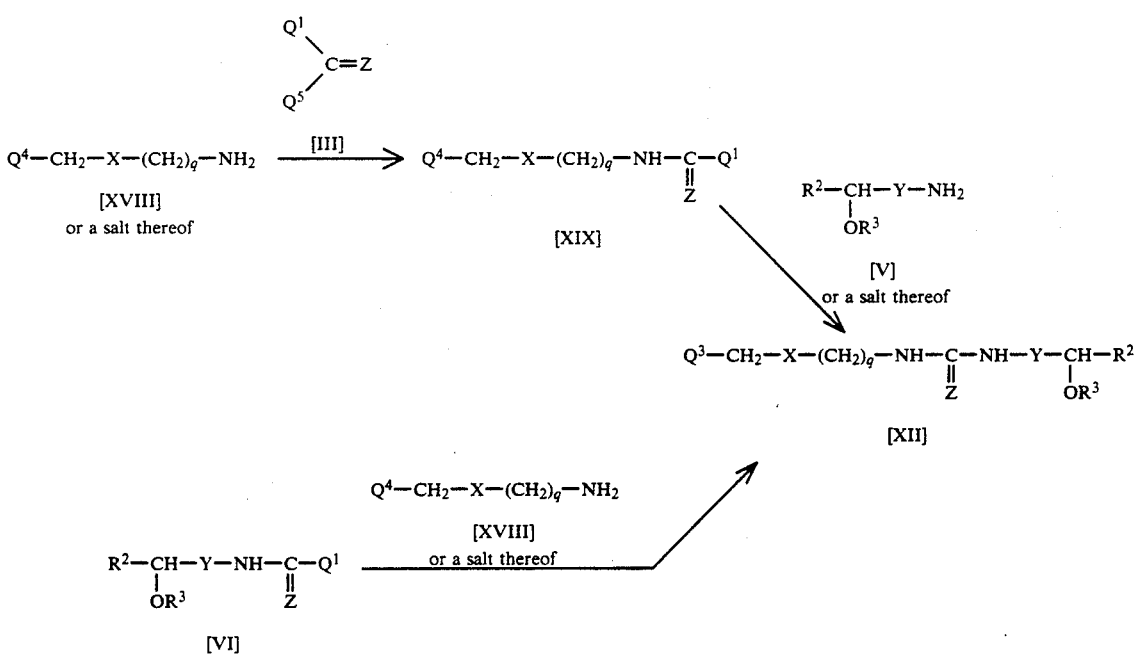
The solvent may be any solvent so long as it has no adverse effect on the reaction, and there is no particular limitation. Specifically, it includes those exemplified above in Production Processes A and B.
The amount of the compound of the formula [III] used is preferably at least equimolar to that of the compound of the formula [Va] or a salt thereof.

Although the reaction temperature and the reaction time are not critical and may be properly varied depending on the reactants and the like, the reaction is effected preferably at 10° C. to 200° C. for 10 minutes to 24 hours.

2) Process for producing the compound of the formula [VIII] (route 2)

This process is carried out by a conventional method, and a compound [VIII] in which $Q^2$ is a halogen atom or an acyloxy group can easily be obtained, respectively, by halogenation or acylation of a compound [XIV], e.g., with thionyl chloride or with acetic unhydride. Further, a compound [VIII] in which $Q^2$ is an amidinothio group can easily be obtained, for example, by reacting a compound [XIV] with thiourea under acidic conditions. And the thus obtained compound [VIII] having amidinothio group for $Q^2$ is hydrolyzed to obtain a compound [VII] having mercapto group for $Q^2$.

3) Process for producing the compound of the formula [IX] (route 3)

This process is carried out by reacting a compound represented by the formula [VI] with a compound represented by the formula [XV] or a salt thereof, or by reacting a compound represented by the formula [V] or a salt thereof with a compound represented by the formula [XVII] produced by reacting a compound represented by the formula [XV] or a salt thereof with a compound represented by the formula [III].

The reaction can be effected in substantially the same manner as in Production Processes A and B. Although the reaction temperature and the reaction time are not critical and may be properly varied depending on the reactants and the like, the reaction is effected at preferably −30° C. to 200° C., more preferably −20° C. to 120° C., for 10 minutes to 48 hours.

In some case, the reaction is preferably effected in an inert gas atmosphere, for example, in a nitrogen atmosphere.

4) Process for producing the compound of the formula [XI] (route 3)

This process is carried out by reacting a compound represented by the formula [VI] with ethyleneimine represented by the formula [XVI] or a salt thereof, or by reacting a compound represented by the formula [XX] with a compound represented by the formula [V] or a salt thereof.

The reaction can be effected in substantially the same manner as in Production Processes A and B.

Further, in this reaction, $R^3$ is preferably a hydroxyl-protecting group, and in this case, the compound obtained may be used as it is as the starting material in Production Process E.

5) Process for producing the compound of the formula [XII] (route 4)

This process is carried out by reacting a compound represented by the formula [V] or a salt thereof with a compound of the formula [XIX] which has been produced by the reaction of a compound represented by the formula [XVIII] or a salt thereof with a compound represented by the formula [III], or by reacting a compound represented by the formula [VI] with a compound represented by the formula [XVIII] or a salt thereof.

This reaction can be effected in substantially the same manner as in Production Processes A and B.

Some of these intermediates are novel compounds, which are included in this invention.

The novel compounds are, for example, those represented by the following formulas:

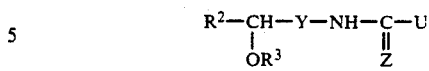

wherein U is any of the removable groups described for Q or an ethyleneimino group, and $R^2$, $R^3$, Y and Z have the same meanings as defined above, and

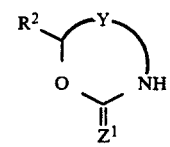

wherein $Z^1$ is nitromethylene group, an alkylsulfonylimino group, a substituted or unsubstituted arylsulfonylimino group, a cyanoimino group, a sulfonoylimino group, or a salt thereof.

In the above-mentioned production processes and the processes for producing the starting compounds, active groups such as hydroxyl group, amino group, carboxyl group or the like can properly be protected with a corresponding protecting group and then subjected to removal thereof in a conventional manner.

The protecting groups for the hydroxyl group include those commonly known as protecting groups for hydroxyl group, for example, those exemplified above as the hydroxyl-protecting group for $R^3$ The protecting groups for the amino group include those commonly known as protecting groups for amino group, for example, formyl group; $C_{2-5}$alkanoyl groups such as acetyl, propionyl, isovaleryl, pivaroyl and the like; aroyl groups such as benzoyl, toluoyl, 2-naphthoyl and the like; alkoxycarbonyl groups such as ethoxycarbonyl, isopropoxycarbonyl, tert-butoxycarbonyl and the like; halogeno-$C_{2-5}$alkanoyl groups such as monochloroacetyl, dichloroacetyl and the like; furoyl group; trityl group; 2-nitrophenylthio; 2,4-dinitrophenylthio; organic silylcontaining groups such as trimethylsilyl, tert-butyldimethylsilyl and the like; etc. The protecting groups for the carboxyl group include those commonly known as protecting groups for carboxyl group, for example, alkyl groups; benzyl group; p-nitrobenzyl group; p-methoxybenzyl group; diphenylmethyl group; trityl group; organic silyl-containing groups such as trimethylsilyl, tert.butyldimethylsilyl and the like; etc.

The thus obtained amine derivative of the formula [I] or a salt thereof can easily be isolated and collected by a conventional procedure, e.g., recrystallization, concentration, extraction, optical resolution, column chromatography or the like. A compound represented by the formula [I] in which $R^3$ is a hydrogen atom can be further converted to a compound represented by the formula [I] in which $R^3$ is a hydroxyl-protecting group by a conventional method, and the compound in which $R^3$ is a hydroxyl-protecting group can be converted to the compound in which $R^3$ is a hydrogen atom by removing the hydroxyl-protecting group by a conventional method For example, a compound represented by the formula [I]in which $R^3$ is a hydrogen atom can be converted to a compound represented by the formula [I] in which $R^3$ is an acyl group, e.g., an acetyl group, by subjecting the former to acylation. When $R^3$ is a hydroxyl-protecting group, e.g., tert.-butyldimethylsilyl group, this group can be removed by hydrolysis by the action of [tetra(n-butyl)]ammonium fluoride. A compound represented by the formula [I] in which $R^1$ or $R^2$ has a substituent, for example, a hydroxyl group was converted by acylation to a desired compound in which $R^1$ or $R^2$ is substituted by an acyloxy group. A compound represented by the formula [I] in which $R^1$ or $R^2$ has a nitro group as the substituent is converted by reduction to a desired compound in which $R^1$ or $R^2$ has an amino group as the substituent.

The amine derivative represented by the formula [I] or a salt thereof can be thus converted to another desired compound in a conventional manner. Further, the salt of the amine derivative of the formula [I] can easily be obtained from the amine derivative in the free state in a conventional manner.

Anti-ulcer agents containing the amine derivative of the general formula [I] or a salt thereof are prepared in a conventional manner in the form of tablets, hard capsules, soft capsules, granules, powder, fine granules, pills, troches, ointments, suppositories, injections, suspensions, emulsions, drops, syrups or the like, and can be administered either orally or parenterally and in particular, oral administration is preferred.

In order to prepare them in various forms suitable for oral or parenteral administration, the preparation may be carried out by using pharmaceutically acceptable additives which are usually used, such as excipients, binders, lubricants, disintegrators, bases for suppositories and the like. Further, if necessary, other additives may also be used such as isotonicities, stabilizers, dispersants, antioxidants, colorants, perfumes, buffers and the like.

Other therapeutically useful medicines may also be incorporated.

The amine derivative of the formula [I] or the salt thereof is usually administered orally or parenterally to an adult in a dosage of 0.001 mg/kg to 10 mg/kg a day in 1 to 4 portions, though the dosage and the administration time may properly be varied depending on the administration route and the symptoms of patients.

Next, this invention is explained below referring to Examples and Preparation Examples, which are not by way of limitation but by way of illustration.

EXAMPLE 1

(1) With 600 ml of ethanol were mixed 153 g of furfuryl alcohol, 128 g of dimethylamine hydrochloride and 70 g of paraformaldehyde, and the resulting mixture was subjected to reaction under reflux for 2 hours. Thereafter, 70 g of paraformaldehyde was further added, and the mixture thus obtained was subjected to reaction under reflux for 18 hours. After completion of the reaction, the solvent was removed by distillation under reduced pressure, and 500 ml of water and 86 g of anhydrous sodium carbonate were added to the resulting residue. The oily substance separated was extracted with three 500-ml portions of diethyl ether, and the extracts were combined and then dried over anhydrous magnesium sulfate, after which the solvent was removed by distillation under reduced pressure. The oily substance thus obtained was distilled under reduced pressure to obtain 105 g (yield 43.4%) of 5-(dimethylamino)methyl-2-furfuryl alcohol having a boiling point of 128°–133° C./15 mmHg.

(2) To a solution of 50.0 g of cysteamine hydrochloride in 180 ml of concentrated hydrochloric acid was added dropwise 68.3 g of the 5-(dimethylamino)methyl-2-furfuryl alcohol obtained in above (1) with stirring at 0° C. to 5° C. After the addition, the resulting mixture was subjected to reaction at 0° C. to 5° C. for 20 hours. Thereto was added 400 ml of water, and the mixture thus obtained was neutralized with sodium carbonate, and then adjusted to a pH of 10 with 10 N aqueous sodium hydroxide solution. The oily substance separated was extracted with 500 ml of chloroform, and the extract was dried over anhydrous magnesium sulfate, after which the solvent was removed by distillation under reduced pressure to obtain 42.5 g (yield 45%) of 2{[5-(dimethylamino)methyl-2-furyl]methylthio}ethylamine having a boiling point of 120°–130° C./1 mmHg.

(3) The 200 ml of dioxane were added 40.0 g of the 2-{[5-(dimethylamino)methyl-2-furyl]methylthio}ethylamine obtained in above (2) and 61.7 g of 1,1-bis(methylthio)-2-nitroethene, and the resulting mixture was subjected to reaction under reflux for 10 minutes. After completion of the reaction, the solvent was removed by distillation under reduced pressure, and 200 ml of ethanol was added to the resulting residue, after which the insolubles were removed by filtration. The solvent was removed by distillation under reduced pressure, and the resulting residue was purified by a column chromatography (Wako Silica Gel C-200, eluent; chloroform:ethanol=30:1 by volume) to obtain 44 g (yield 71.3%) of 1-{2-[[5-(dimethylamino)methyl-2-furyl]methylthio]ethylamino}-1-methylthio-2-nitroethene having a melting point of 71° C. (4) In 6 ml of ethanol were dissolved 1.0 g of the 1-[2-[[5-(dimethylamino)methyl-2-furyl]methylthio]ethylamino}-1-methylthio-2-nitroethene obtained in above (3) and 2.0 g of DL-β-hydroxyphenethylamine, and the resulting solution was subjected to reaction under reflux for 2 hours. After completion of the reaction, the solvent was removed by distillation under reduced pressure, and the resulting residue was purified by a column chromatography (Wako Silica Gel C-200, eluent; chloroform:ethanol =10:1 by volume), and recrystallized form acetonitrile to obtain 0.95 g (yield 71% of N-{2-[[5-(dimethylamino)methyl-2-furyl]methylthio]ethyl}-N'-(β-hydroxyphenethyl)-2-nitro-1,1-ethenediamine having a melting point of 115°–116° C.

Elementary analysis values (for $C_{20}H_{28}N_4O_4S_1$): Calculated (%): C: 57.12, H: 6.71, N: 13.32; Found (%): C: 57.34, H: 6.97, N: 13.23.

The compound listed in Table 9 were obtained in the same manner as described above.

TABLE 9

$$\underset{H_3C}{\overset{H_3C}{>}}NCH_2-\underset{O}{\boxed{\phantom{xx}}}-CH_2SCH_2CH_2NHCNHCH_2^*CHR^2$$
$$\underset{HCNO_2}{\|}\quad\underset{OH}{|}$$

| $R^2$ | Physical properties |
|---|---|
| 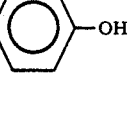 —OH | Melting point: 131° C.<br>Elementary analysis values (for $C_{20}H_{28}N_4O_5S_1$)<br>Calculated (%): C: 55.03, H: 6.46, N: 12.84<br>Found (%): C: 55.27, H: 6.71, N: 13.00 |
| 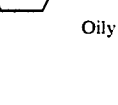 —OH<br>Oily | NMR($d_6$-DMSO) δ values:<br>2.15(6H, s, —CH$_3 \times$2), 2.44–2.89(2H, m, >CH$_2$),<br>3.07–3.65(4H, m, >CH$_2 \times$2), 3.42(2H, s, >CH$_2$),<br>3.94(2H, s, >CH$_2$), 4.75(1H, m, —C$\underline{H}$—),<br>$\quad\quad\quad\quad\quad\quad\quad\quad\quad\quad\quad\quad\quad\quad\quad$ OH<br>6.20(1H, d, furan ring H), 6.29(1H, d, furan ring H), 6.55–7.42 (6H, m, >NH, =CH—, benzene ring H$\times$4), 10.27(1H, bs, >NH) |
| —OCH$_3$<br>Oily | NMR(CDCl$_3$) δ values:<br>2.08(6H, s, —CH$_3\times$2), 2.56–3.02(2H, m, >CH$_2$),<br>3.12–3.70(6H, m, >CH$_2 \times$3), 3.82(2H, s, >CH$_2$),<br>3.85(3H, s, —CH$_3$), 4.90(1H, m, —C$\underline{H}$—), 6.24(2H,<br>$\quad\quad\quad\quad\quad\quad\quad\quad\quad\quad\quad\quad\quad\quad\quad$ OH<br>s, furan ring H$\times$2), 6.68(1H, s, =CH—), 6.98, 7.48 (4H, AA', BB', benzene ring H$\times$4), 7.90–8.40(1H, b, >NH) |
| —OCH$_3$ | Melting point: 130–131° C. |
| OCH$_3$<br>Oily | NMR($d_6$-DMSO) δ values:<br>2.13(6H, s, —CH$_3\times$2), 2.47–2.95(2H, m, >CH$_2$),<br>3.45(2H, s, >CH$_2$), 3.16–3.66(4H, m, >CH$_2 \times$2),<br>3.90(2H, s, >CH$_2$), 3.93(3H, s, —CH$_3$), 5.20(1H, m,<br>—C$\underline{H}$—), 6.34(2H, s, furan ring H$\times$2), 6.54–7.83<br>OH<br>(6H, m, =CH—, >NH, benzene ring H$\times$4), 10.31(1H, bs, >NH) |
| —F | Melting point: 132.5–133.5° C. |
| F | Melting point: 125–126° C. |
| F | Melting point: 102–103° C.<br>NMR(CDCl$_3$) δ values:<br>2.10(6H, s, —CH$_3\times$2), 2.60–2.97(2H, m, >CH$_2$),<br>3.17–3.71(4H, m, >CH$_2\times$2), 3.38(2H, s, >CH$_2$),<br>3.78(2H, s, >CH$_2$), 5.28(1H, m, —C$\underline{H}$—), 6.20(2H,<br>$\quad\quad\quad\quad\quad\quad\quad\quad\quad\quad\quad\quad\quad\quad\quad$ OH<br>s, furan ring H$\times$2), 6.65(1H, s, =CH—), 6.86–7.90 (4H, m, benzene ring H$\times$4),10.30(1H, bs, >NH) |
| —Cl | Melting point: 123–124° C. |
| Cl<br>Oily | NMR(CDCl$_3$) δ values:<br>2.14(6H, s, —CH$_3\times$2), 2.63–3.07(2H, m, >CH$_2$),<br>3.28–3.79(4H, m, >CH$_2\times$2), 3.45(2H, s, >CH$_2$),<br>3.90(2H, s, >CH$_2$), 5.46(1H, m, —C$\underline{H}$—), 6.35(2H,<br>$\quad\quad\quad\quad\quad\quad\quad\quad\quad\quad\quad\quad\quad\quad\quad$ OH<br>s, furan ring H$\times$2), 6.81(1H, s, =CH—),7.23–8.45 (5H, m, >NH, benzene ring H$\times$4), 10.45(1H, bs, >NH) |

TABLE 9-continued $$\underset{H_3C}{\overset{H_3C}{>}}NCH_2-\underset{O}{\langle\text{furan}\rangle}-CH_2SCH_2CH_2NHCNHCH_2CHR^2$$
$$\underset{HCNO_2}{\|}\quad\underset{OH}{|}$$

| R² | Physical properties |
|---|---|
| —⟨benzene⟩—CH₃ (para) | Melting point: 111–113° C. |
| ⟨benzene with CH₃ ortho⟩ Oily | NMR(CDCl₃) δ values:<br>2.08(6H, s, —CH₃×7), 2.36(3H, s, —CH₃), 2.58–3.98 (2H, m, >CH₂), 3.16–3.65(4H, m, >CH₂×2), 3.36(2H, s, >CH₂), 3.79(2H, s, >CH₂), 5.20(1H, m, —C$\underline{H}$—),<br>$\quad\quad\quad\quad\quad\quad\quad\quad\quad\quad\quad\quad\quad$ OH<br>6.22(2H, s, furan ring H×2), 6.65(1H, s, =CH—), 7.10–7.81(4H, m, benzene ring H×4), 10.19(1H, bs, >NH) |
| —⟨benzene⟩—CH₂CH₃ (para) | Melting point: 116–117° C. |
| ⟨benzene with —OCH₂O— fused⟩ | Melting point: 113–114° C.<br>NMR(CDCl₃) δ values:<br>2.01(6H, s, —CH₃×2), 2.64–2.98(2H, m, >CH₂), 3.09–3.65(4H, m, >CH₂×2), 3.29(2H, s, >CH₂), 3.77(2H, s, >CH₂), 4.87(1H, m, —C$\underline{H}$—), 6.00(2H,<br>$\quad\quad\quad\quad\quad\quad\quad\quad\quad\quad\quad\quad\quad$ OH<br>s, —OCH₂O—), 6.11(2H, s, furan ring H×2), 6.55 (1H, s, =CH—), 6.78–7.68(3H, m, benzene ring H×3), 7.71–8.13(1H, b, >NH) |
| ⟨benzene with 2 F⟩ Oily | NMR(CDCl₃) δ values:<br>2.15(6H, s, —CH₃×2), 2.57–2.96(2H, m, >CH₂), 3.10–3.92(4H, m, >CH₂×2), 3.36(2H, s, >CH₂), 3.72(2H, s, >CH₂), 5.29(1H, m, —C$\underline{H}$—), 6.14(2H,<br>$\quad\quad\quad\quad\quad\quad\quad\quad\quad\quad\quad\quad\quad$ OH<br>s, furan ring H×2), 6.59(1H, s, =CH—), 6.44–7.56 (4H, m, benzene ring H×3, >NH), 10.31(1H, bs, >NH) |
| ⟨benzene with 2 F⟩ | Melting point: 114° C. |
| ⟨benzene with 2 F⟩ | Melting point: 94–96° C. |
| ⟨benzene with CH₃ and F⟩ Oily | NMR(CDCl₃) δ values:<br>2.10(6H, s, —CH₃×2), 2.35(3H, s, —CH₃), 2.60–2.98(2H, m, >CH₂), 3.10–3.65(4H, m, >CH₂×2), 3.36(2H, s, >CH₂), 3.78(2H, s, >CH₂), 5.15(1H, m, —C$\underline{H}$—), 5.95(1H, bs, —OH), 6.20(2H, s, furan<br>$\quad\quad$ OH<br>ring H×2), 6.62(1H, s, =CH—), 6.71–7.82(4H, m, >NH, benzene ring H×3), 10.25(1H, bs, >NH) |
| ⟨thiophene⟩ Oily | NMR(d₆-DMSO) δ values:<br>2.06(6H, s, —CH₃×2), 2.37–2.76(2H, m, >CH₂), 3.07–3.58(4H, m, >CH₂×2), 3.35(2H, s, >CH₂), 3.78(2H, s, >CH₂), 4.95(1H, m, —C$\underline{H}$—), 6.06(1H,<br>$\quad\quad\quad\quad\quad\quad\quad\quad\quad\quad\quad\quad\quad$ OH<br>d, furan ring H), 6.14(1H, d, furan ring H), 6.49 (1H, s, =CH—), 6.76–7.03(2H, m, thiophene ring H×2), 7.23–7.42(1H, m, thiophene ring H) |

TABLE 9-continued $$\text{(H}_3\text{C)}_2\text{NCH}_2\text{-[furan]-CH}_2\text{SCH}_2\text{CH}_2\text{NHCNHCH}_2\text{CHR}^2$$
$$\phantom{xxxxxxxxxxxxxxxxxxxxxxxx}\|\phantom{xxxxx}|$$
$$\phantom{xxxxxxxxxxxxxxxxxxxxxxxx}\text{HCNO}_2\phantom{x}\text{OH}$$

| R² | Physical properties |
|---|---|
| 3-methyl-thiophen-2-yl<br>Oily | NMR(CDCl₃) δ values:<br>2.05(6H, s, —CH₃×2), 2.13(3H, s, —CH₃),<br>2.50–2.89(2H, m, >CH₂), 3.08–3.68(4H, m, >CH₂×2), 3.31(2H, s, >CH₂), 3.69(2H, s, >CH₂), 5.14(1H, m, —C<u>H</u>—), 6.08(2H, s, furan ring H×2), 6.51(1H, s,<br>                  OH<br>=CH—), 6.69(1H, d, thiophene ring H), 7.05(1H, d, thiophene ring H), 10.28(1H, bs, >NH) |
| thiophen-2-yl<br>Oily | NMR(CDCl₃) δ values:<br>2.14(6H, s, —CH₃×2), 2.48–3.05(2H, m, >CH₂),<br>3.18–3.68(4H, m, >CH₂×2), 3.40(2H, s, >CH₂),<br>3.78(2H, s, >CH₂), 5.03(1H, m, —C<u>H</u>—), 5.68(1H,<br>                  OH<br>bs, —OH), 6.18(2H, s, furan ring H×2), 6.64(1H, s,<br>=CH—), 6.90–7.98(4H, m, >NH, thiophene ring H× 3), 10.28(1H, bs, >NH) |
| furan-2-yl<br>Oily | NMR(CDCl₃) δ values:<br>2.14(6H, s, —CH₃×2), 2.60–2.92(2H, m, >CH₂),<br>3.14–3.86(4H, m, >CH₂×2), 3.40(2H, s, >CH₂),<br>3.76(2H, s, >CH₂), 4.96(1H, m, —C<u>H</u>—), 5.42(1H,<br>                  OH<br>bs, —OH), 6.19(2H, s, furan ring H×2), 6.38(2H, s, furan ring H×2), 6.63(1H, s, =CH—), 7.41(1H, s, furan ring H), 7.80(1H, bs, >NH), 10.32(1H, bs, >NH) |
| pyridin-4-yl<br>Oily | NMR(CDCl₃) δ values:<br>2.09(6H, s, —CH₃×2), 2.50–2.95(2H, m, >CH₂),<br>3.00–3.90(4H, m, >CH₂×2), 3.30(2H, s, >CH₂),<br>3.67(2H, s, >CH₂), 4.90(1H, m, —C<u>H</u>—), 6.04(2H,<br>                  OH<br>s, furan ring H×2), 6.47(1H, s, =CH—), 7.15(1H, m, pyridine ring H), 7.68(1H, m, pyridine ring H), 8.33(1H, m, pyridine ring H), 8.49(1H, m, pyridine ring H), 10.35(1H, bs, >NH) |
| pyridin-2-yl<br>Oily | NMR(CDCl₃) δ values:<br>2.20(6H, s, —CH₃×2), 2.63–3.08(2H, m, >CH₂),<br>3.19–3.78(4H, m, >CH₂×2), 3.50(2H, s, >CH₂),<br>3.87(2H, s, >CH₂), 5.15(1H, m, —C<u>H</u>—), 6.30(2H,<br>                  OH<br>s, furan ring H×2), 6.76(1H, s, =CH—), 7.28–7.52(1H, m, pyridine ring H), 7.64–8.17(2H, m, pyridine ring H× 2), 8.75(1H, m, pyridine ring H) |
| 4-pyridyl-phenyl<br>Oily | NMR(CDCl₃) δ values:<br>2.13(6H, s, —CH₃×2), 2.62–2.99(2H, m, >CH₂),<br>3.20–3.71(4H, m, >CH₂×2), 3.40(2H, s, >CH₂),<br>3.81(2H, s, >CH₂), 5.00(1H, m, —C<u>H</u>—), 6.26(2H,<br>                  OH<br>s, furan ring H×2), 6.68(1H, s, =CH—), 7.55(2H, d, pyridine ring H×2), 8.67(2H, d, pyridine ring H×2), 10.33(1H, bs, >NH) |
| 4-cyanophenyl<br>Amorphous | IR(KBr)cm⁻¹: $\nu_{C\equiv N}$ 2220<br>NMR(CDCl₃) δ values:<br>2.11(6H, s, —CH₃×2), 2.40–3.05(2H, m, >CH₂),<br>3.05–4.25(6H, m, >CH₂×3), 3.80(2H, s, >CH₂),<br>4.80–5.30(1H, m, —C<u>H</u>—), 6.20(2H, s, furan ring<br>                  OH<br>H×2), 6.65(1H, s, =CH—), 7.68(4H, s, benzene ring H×4), 10.35(1H, bs, >NH) |
| 4-hydroxymethylphenyl<br>Oily | NMR(CDCl₃) δ values:<br>2.08(6H, s, —CH₃×2), 2.55–3.10(2H, m, >CH₂),<br>3.15–3.65(4H, m, >CH₂×2), 3.38(2H, s, >CH₂),<br>3.83(2H, s, >CH₂), 4.74(2H, s, >CH₂), 4.85–5.11(1H, m, —C<u>H</u>—), 6.25(2H, s, furan ring H×2), 6.68(1H, s,<br>                  OH<br>=CH—), 7.48(4H, s, benzene ring H×4) |

TABLE 9-continued $$\underset{H_3C}{\overset{H_3C}{>}}\!\!NCH_2\!\!-\!\!\underset{O}{\boxed{\phantom{xx}}}\!\!-CH_2SCH_2CH_2NHCNHCH_2CHR^2$$
$$\qquad\qquad\qquad\qquad\qquad\underset{HCNO_2}{\overset{\|}{}}\quad\underset{OH}{|}$$

| $R^2$ | Physical properties |
|---|---|
| —⟨benzene⟩—OCH₂CH₃<br>Oily | NMR(CDCl₃) δ values:<br>1.37(3H, t, —CH₃), 2.04(6H, s, —CH₃×2), 2.49–2.98<br>(2H, m, >CH₂), 3.09–3.61(4H, m, >CH₂×2), 3.30(2H,<br>s, >CH₂), 3.72(2H, s, >CH₂), 4.0(2H, q, —OC<u>H</u>₂CH₃),<br>4.84(1H, m, —C<u>H</u>—), 6.11(2H, s, furan ring H×2),<br>     \|<br>     OH<br>6.55(1H, s, =CH—), 6.83, 7.29(4H, AA′, BB′, benzene<br>ring H×4), 10.38(1H, bs, >NH) |
| —⟨benzene⟩—SCH₃<br>Oily | NMR(CDCl₃) δ values:<br>2.06(6H, s, —CH₃×2), 2.50(3H, s, —SCH₃), 2.6–3.0(2H,<br>m, >CH₂), 3.1–3.7(4H, m, >CH₂×2), 3.37(2H, s, >CH₂),<br>3.80(2H, s, >CH₂), 4.9(1H, m, —C<u>H</u>—), 6.23(2H, s, furan<br>            \|<br>            OH<br>ring H×2), 6.68(1H, s, =CH—), 7.39(4H, s, benzene ring<br>H×4), 8.1(1H, bs, >NH) |
| —⟨benzene⟩—S(=O)CH₃<br>Oily | NMR (CDCl₃) δ values:<br>2.09(6H, s, —CH₃×2), 2.7–3.05(2H, m, >CH₂),<br>2.78(3H, s, —SCH₃), 3.1–3.7(4H, m, >CH₂×2),<br>3.37(2H, s, >CH₂), 3.83(2H, s, >CH₂), 5.05(1H, m,<br>—C<u>H</u>—), 6.23(2H, s, furan ring H×2), 6.65(1H, s,<br> \|<br> OH<br>=CH—), 7.71(4H, s, benzene ring H×4), 8.0(1H,<br>bs, >NH)<br>Melting point: 110–112° C. |
| —⟨benzene⟩—CH₂CH₂CH₃ | Melting point: 130–132° C. |
| —⟨benzene⟩—CF₃ | |
| —⟨benzene(OCH₃)(OCH₃)⟩<br>Oily | NMR(CDCl₃) δ values:<br>2.11(6H, s, —CH₃×2), 2.52–2.93(2H, m, >CH₂),<br>3.06–4.02(4H, m >CH₂×2), 3.36(2H, s, >CH₂),<br>3.76(2H, s, >CH₂), 3.85(6H, s, —CH₃×2), 4.93(1H,<br>m, —C<u>H</u>—), 6.20(2H, s, furan ring H×2), 6.67(1H,<br>  \|<br>  OH<br>s, =CH—), 6.94(2H, s, benzene ring H×2), 7.18(1H,<br>s, benzene ring H), 10.30(1H, bs, >NH)<br>Melting point: 138–139° C. |
| —⟨benzene(F)(F)⟩ | |

EXAMPLE 2

(1) In 200 ml of methylene chloride were dissolved 20.8 g of 3-methyl-2-thenyl alcohol and 27.1 ml of triethylamine, and 12.9 ml of thionyl chloride was added thereto dropwise at −15° C. to −10° C. over a period of 30 minutes, after which the resulting solution was further subjected to reaction at the same temperature for 30 minutes. The reaction mixture was poured into ice water, and the organic layer was separated and then dried over anhydrous magnesium sulfate. Subsequently, the dried organic layer was added dropwise with ice-cooling to a solution of 95 g of dimethylamine in 550 ml of ethanol, and the resulting mixture was allowed to stand overnight at room temperature. The solvent was removed by distillation under reduced pressure, after which 100 ml of water was added to the residue, and the resulting mixture was adjusted to pH 10 with potassium carbonate, and then extracted with 200 ml of ethyl acetate. The extract was washed with 50 ml of a saturated aqueous sodium chloride solution and dried over anhydrous potassium carbonate, after which the solvent was removed by distillation under reduced pressure, and the oily substance thus obtained was distilled under reduced pressure to obtain 19.0 g (yield 75%) of 2-(dimethylamino)methyl-3-methylthiophene having a boiling point of 85°–86° C./14 mmHg.

(2) In 70 ml of anhydrous tetrahydrofuran was dissolved 15.5 g of the 2-(dimethylamino)methyl-3-methylthiophene obtained in above (1), and 70 ml of a n-butyllithium-n-hexane solution (15% by weight solution) was added dropwise at −20° C. to −10° C. in a nitrogen atmosphere. After the addition, the temperature of the resulting solution was gradually raised, and the solution was subjected to reaction at room temperature for 4 hours. After completion of the reaction, 3.6 g of paraformaldehyde was added to the solution with-ice-cooling, and the resulting mixture was further subjected to reaction for 2 hours after the generation of heat ceased. After completion of the reaction, the solvent was removed by distillation under reduced pressure, and 20 ml of ice water and 100 ml of chloroform were added to the resulting residue, after which the organic layer was separated. The organic layer was washed successively with 20 ml of water and 10 ml of a saturated aqueous sodium chloride solution, and then dried over anhydrous magnesium sulfate, after which the solvent was removed by distillation under reduced pressure, and the unreacted materials were removed from the oily substance thus obtained by distillation under reduced pressure on an oil bath at 110° C. to 115° C. to obtain 17.0 g (yield 92%) of crude 5-(dimethylamino)-methyl-4-methyl-2-thenyl alcohol.

(3) To a solution of 15.6 g of cysteamine hydrochloride in 115 ml of concentrated hydrochloric acid was added 17.0 g of the crude 5-(dimethylamino)methyl-4-methyl-2-thenyl alcohol obtained in above (2) at 0° C., and the resulting mixture was subjected to reaction at room temperature for 2 days. After completion of the reaction, sodium carbonate was gradually added with ice-cooling until the water disappeared, and the separated oily substance was extracted with 200 ml of ethyl acetate. The extract was dried over anhydrous potassium carbonate, and the solvent was removed by distillation under reduced pressure to obtain 20.4 g (yield 91%) of yellow, oily, crude 2-{[5-dimethylamino)methyl-4-methyl-2-thienyl]methylthio}ethylamine.

(4) With 70 ml of acetonitrile were mixed 14.0 g of the crude 2-{[5-(dimethy[amino)methyl-4-methyl-2-thienyl]methylthio}ethylamine obtained in above (3) and 19.0 g of 1,1-bis(methylthio)-2-nitroethene, and the resulting mixture was subjected to reaction under reflux for 2 hours. After completion of the reaction, the solvent was removed by distillation under reduced pressure, and 30 ml of ethanol was added to the resulting residue, after which the insolubles were removed by filtration. The solvent was removed by distillation under reduced pressure, and the resulting residue was purified by a column chromatography (Wako Silica Gel C-200, eluent; chloroform: methanol=30:1 by volume) to obtain 19.0 g (yield 92%) of 1-{2-[[5-(dimethylamino)methyl-4-methyl-2-thienyl]methylthio]ethylamino}-1-methylthio-2-nitroethene having a melting point of 69°-71° C.

NMR (CDCl$_3$) δ values: 2.13 (3H, s, —CH$_3$), 2.27 (6H, s, —CH$_3$×2), 2.46 (3H, s, —CH$_3$), 2.79 (2H, t, >CH$_2$), 3.45–3.85 (2H, m, >CH$_2$), 3.51 (2H, s, >CH$_2$), 3.91 (2H, s, >CH$_2$), 6.60 (1H, s, =CH—), 6.71 (1H, s, thiophene ring H), 10.6 (1H, bs, >NH)

(5) With 6 ml of ethanol were mixed 0.60 g of the 1-{2-[[5-(dimethylamino)methyl-4-methyl-2-thienyl]-methylthio]ethylamino}-1-methylthio-2-nitroethene obtained in above (4) and 1.10 g of DL-[2-(4-ethylphenyl)-2-hydroxyethyl]amine, and the resulting mixture was subjected to reaction under reflux for 1 hour. After completion of the reaction, the solvent was removed by distillation under reduced pressure, and the resulting residue was purified by a column chromatography (Wako Silica Gel C-200, eluent; chloroform:ethanol=20:1 by volume) and crystallized from isopropanol-diethyl ether solution to obtain 0.55 g (yield 69% of N-{2-[[5-(dimethylamino)methyl-4-methyl-2-thienyl]methylthio]ethyl}-N'-[2-(4-ethylphenyl)-2-hydroxyethyl]-2-nitro-1,1-ethenediamine having a melting point of 112°-115° C.

Elementary analysis values (for C$_{23}$H$_{34}$N$_4$O$_3$S$_2$): Calculated (%): C: 57.71, H: 7.16, N: 11.70; Found (%): C: 57.82, H: 7.19, N: 11.43.

The compounds shown in Table 10 were obtained in the same manner as described above.

TABLE 10

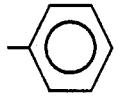

| R$^2$ | Physical properties |
|---|---|
| 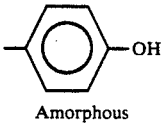 | Melting point: 114–115° C. NMR(CDCl$_3$) δ values: 2.10(9H, s, —CH$_3$×3), 2.5–3.0 (2H, m, >CH$_2$), 3.1–3.7(4H, m, >CH$_2$×2), 3.45(2H, s, >CH$_2$), 3.89(2H, s, >CH$_2$), 4.9(1H, m, —CH— \| OH ), 5.8(1H, bs, —OH), 6.60 (1H, s, =CH—), 6.72(1H, s, thiophene ring H), 7.42(5H, s, benzene ring H×5), 10.3(1H, bs, >NH) |
| 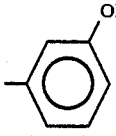  Amorphous | NMR(d$_6$-DMSO) δ values: 2.10(3H, s, —CH$_3$), 2.20(6H, s, —CH$_3$×2), 2.4–2.9(2H, m, >CH$_2$), 3.0–3.75(4H, m, >CH$_2$×2), 3.49 (2H, s, >CH$_2$), 3.98(2H, s, >CH$_2$), —CH— 4.75(1H, m, \| ), 5.75(1H, bs, OH —OH), 6.62(1H, s, =CH—), 6.81 (1H, s, thiophene ring H), 6.83, 7.33(4H, AA', BB', benzene ring H×4) |
| OH on ring; Amorphous | NMR(d$_6$-DMSO) δ values: 2.07(3H, s, —CH$_3$), 2.15(6H, s, —CH$_3$×2), 2.35–2.9(2H, m, >CH$_2$), 3.0–3.75(4H, m, >CH$_2$×2), 3.43 (2H, s, >CH$_2$), 3.92(2H, s, >CH$_2$), —CH— 4.7(1H, m, \| ), 5.7(1H, bs, OH —OH), 6.4–7.35(6H, m, benzene ring H×4, thiophene ring H, =CH—), 10.3(1H, bs, >NH) |
| 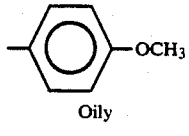  Oily | NMR(CDCl$_3$) δ values: 2.15(9H, s, —CH$_3$×3), 2.55–3.0 (2H, m, >CH$_2$), 3.1–4.1(6H, m, >CH$_2$×3), 3.48(2H, s, >CH$_2$), 3.81(3H, s, —CH$_3$), 4.95(1H, m, —CH— \| ), 6.67(1H, bs, =CH—), OH 6.76(1H, s, thiophene ring H), 6.97, 7.41(4H, AA', BB', benzene ring H×4) |

TABLE 10-continued

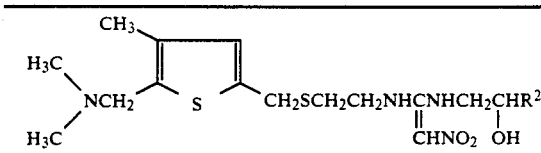

| R² | Physical properties |
|---|---|
| ![4-OCH3-phenyl] Oily | NMR(CDCl₃) δ values: 2.15(9H, s, —CH₃×3), 2.55-2.95 (2H, m, >CH₂), 3.05-3.7(4H, m, >CH₂×2), 3.48(2H, s, >CH₂), 3.85(3H, s, —CH₃), 3.93(2H, s, >CH₂), 4.95(1H, m, —CH(OH)—), 6.66 (1H, s, =CH—), 6.7-7.6(5H, m, thiophene ring H, benzene ring H×4), 10.3(1H, bs, >NH) |
| ![2-OCH3-phenyl] | Melting point: 105-107° C. NMR(CDCl₃) δ values: 2.10(3H, s, —CH₃), 2.13(6H, s, —CH₃×2), 2.5-2.95(2H, m, >CH₂), 2.95-3.65(4H, m, >CH₂×2), 3.41 (2H, s, >CH₂), 3.81(3H, s, —CH₃), 3.83(2H, s, >CH₂), 5.2(1H, m, —CH(OH)—), 6.45-7.65(6H, m, =CH—, benzene ring H×4, thiophene ring H), 10.3(1H, bs, >NH) |
| ![4-F-phenyl] Oily | NMR(CDCl₃) δ values: 2.12(9H, s, —CH₃×3), 2.5-2.95 (2H, m, >CH₂), 3.0-3.7(4H, m, >CH₂×2), 3.44(2H, s, >CH₂), 3.86(2H, s, >CH₂), 4.9(1H, m, —CH(OH)—), 5.6 (1H, bs, —OH), 6.56 (1H, s, =CH—), 6.66(1H, s, thiophene ring H), 6.75-7.6(4H, m, benzene ring H×4), 10.2(1H, bs, >NH) |
| ![3-F-phenyl] Oily | NMR(CDCl₃) δ values: 2.10(3H, s, —CH₃), 2.12(6H, s, —CH₃×2), 2.5-2.95(2H, m, >CH₂), 3.1-3.7(4H, m, >CH₂×2), 3.45 (2H, s, >CH₂), 3.87(2H, s, >CH₂), 4.9(1H, m, —CH(OH)—), 6.59(1H, s, =CH—), 6.68(1H, s, thiophene ring H), 6.75-7.5(4H, m, benzene ring H×4) |
| ![2-F-phenyl] Oily | NMR(CDCl₃) δ values: 2.12(3H, s, —CH₃), 2.16(6H, s, —CH₃×2), 2.5-2.95(2H, m, >CH₂), 3.05-3.75(4H, m, >CH₂×2), 3.46 (2H, s, >CH₂), 3.87(2H, s, >CH₂), 5.25(1H, m, —CH(OH)—), 6.60(1H, s, =CH—), 6.68(1H, s, thiophene ring H), 6.75-7.8(4H, m, benzene ring H×4) |
| ![4-Cl-phenyl] Oily | NMR(CDCl₃) δ values: 2.12(9H, s, —CH₃×3), 2.45-2.95 (2H, m, >CH₂), 3.05-3.7(4H, m, >CH₂×2), 3.45(2H, s, >CH₂), 3.82(2H, s, >CH₂), 4.9(1H, m, —CH(OH)—), 5.5 (1H, bs, —OH), 6.55 (1H, s, =CH—), 6.65(1H, s, thiophene ring H), 7.32(4H, s, benzene ring H×4) |

TABLE 10-continued

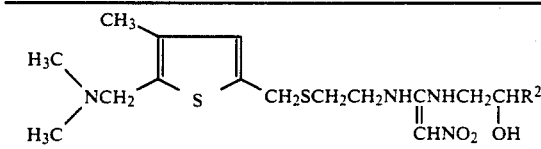

| R² | Physical properties |
|---|---|
| ![4-Cl-phenyl] | Melting point: 97-99° C. NMR(CDCl₃) δ values: 2.13(9H, s, —CH₃×3), 2.4-3.0 (2H, m, >CH₂), 3.0-3.75(4H, m, >CH₂×2), 3.48(2H, s, >CH₂), 3.90(2H, s, >CH₂), 4.95(1H, m, —CH(OH)—), 6.62(1H, s, =CH—), 6.72 (1H, s, thiophene ring H), 7.0-7.6 (4H, m, benzene ring H×4), 10.2 (1H, bs, >NH) |
| ![2-Cl-phenyl] Oily | NMR(CDCl₃) δ values: 2.13(9H, s, —CH₃×3), 2.75(2H, t, >CH₂), 3.05-3.75 (4H, m, >CH₂×2), 3.48(2H, s, >CH₂), 3.90 (2H, s, >CH₂), 5.3(2H, m. —OH, —CH(OH)—), 6.62 (1H, s, =CH—), 6.72 (1H, s, thiophene ring H), 7.1-7.95(4H, m, benzene ring H×4), 10.2(1H, bs, >NH) |
| ![4-CH3-phenyl] Oily | NMR(CDCl₃) δ values: 2.15(9H, s, —CH₃×3), 2.36(3H, s, —CH₃), 2.5-3.0(2H, m, >CH₂), 3.0-3.75(4H, m, >CH₂×2), 3.47 (2H, s, >CH₂), 3.90(2H, s, >CH₂), 4.9(1H, m, —CH(OH)—), 6.64(1H, s, =CH—), 6.73(1H, s, thiophene ring H), 6.95-7.55(4H, m, benzene ring H×4), 10.3(1H, bs, >NH) |
| ![2-CH3-phenyl] Oily | NMR(CDCl₃) δ values: 2.12(9H, s, —CH₃×3), 2.34(3H, s, —CH₃), 2.55-3.05(2H, m, >CH₂), 3.05-3.75(4H, m, >CH₂×2), 3.48 (2H, s, >CH₂), 3.94(2H, s, >CH₂), 5.0-5.7(2H, m, —OH, —CH(OH)—), 6.66 (1H, s, =CH—), 6.78(1H, s, thiophene ring H), 7.05-7.8(4H, m, benzene ring H×4) |
| ![3,4-methylenedioxyphenyl] Oily | NMR(CDCl₃) δ values: 2.14(9H, s, —CH₃×3), 2.55-2.95 (2H, m, >CH₂), 3.1-3.75(4H, m, >CH₂×2), 3.50(2H, s, >CH₂), 3.94(2H, s, >CH₂), 4.9(1H, m, —CH(OH)—), 5.4(1H, bs, —OH), 6.03 (2H, s, —OCH₂O—), 6.68(1H, s, =CH—), 6.78(1H, s, thiophene ring H), 6.85-7.1(3H, m, benzene ring H×3), 7.1-8.1(1H, b, >NH), 10.3(1H, bs, >NH) |
| ![2,4-diF-phenyl] | Melting point: 137-139° C. (recrystallized from ethanol) |

TABLE 10-continued

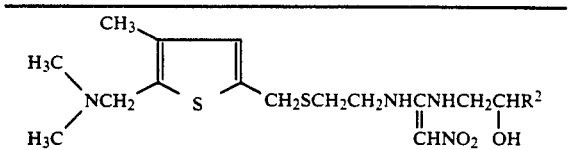

| $R^2$ | Physical properties |
|---|---|
| ![2,4-difluorophenyl] | Melting point: 133–135° C. (recrystallized from ethanol/diethyl ether) |
| ![4-fluoro-2-methylphenyl] | Melting point: 92–95° C. (recrystallized from isopropanol/diethyl ether) |
| ![thiophene] Oily | NMR(CDCl$_3$) δ values: 2.15(9H, s, —CH$_3$×3), 2.5–2.95 (2H, m, >CH$_2$), 3.05–3.75(4H, m, >CH$_2$×2), 3.48(2H, s, >CH$_2$), 3.87(2H, s, >CH$_2$), 5.2(1H, m, —CH(OH)—), 6.45–7.5 (5H, m, =CH—, thiophene ring H×4), 10.3(1H, bs, >NH) |
| ![furan] Oily | NMR(CDCl$_3$) δ values: 2.12(3H, s, —CH$_3$), 2.17(6H, s, —CH$_3$×2), 2.45–2.95(2H, m, >CH$_2$), 3.0–3.75(4H, m, >CH$_2$×2), 3.41(2H, s, >CH$_2$), 3.80(2H, s, >CH$_2$), 4.9(1H, m, —CH(OH)—), 6.27 (2H, bs, furan ring H×2), 6.51(1H, s, =CH—), 6.60(1H, s, thiophene ring H), 7.15–7.45(1H, m, furan ring H) |
| ![2-methylthiophene] Oily | NMR(CDCl$_3$) δ values: 2.10(3H, s, —CH$_3$), 2.15(6H, s, —CH$_3$×2), 2.25 (3H, s, —CH$_3$), 2.4–2.85(2H, m, >CH$_2$), 3.0–3.65 (4H, m, >CH$_2$×2), 3.45(2H, s, >CH$_2$), 3.75(2H, s, >CH$_2$), 5.1 (1H, m, —CH(OH)—), 5.6(1H, bs, —OH), 6.3–7.05(4H, m, =CH—, thiophene ring H×3), 10.3(1H, bs, >NH) |
| ![pyridine] Oily | NMR(CDCl$_3$) δ values: 2.12(3H, s, —CH$_3$), 2.17(6H, s, —CH$_3$×2), 2.55–3.0(2H, m, >CH$_2$), 3.05–3.75(4H, m, >CH$_2$×2), 3.49 (2H, s, >CH$_2$), 3.90(2H, s, >CH$_2$), 5.05(1H, m, —CH(OH)—), 5.9(1H, bs, —OH), 6.66(1H, s, =CH—), 6.75 (1H, s, thiophene ring H), 7.2–7.55, 7.7–8.1(2H, m, pyridine ring H×2), 8.45–8.8(2H, m, pyridine ring H×2), 10.4(1H, bs, >NH) |
| ![2-cyanophenyl] | Melting point: 108–111° C. (Recrystallized from isopropanol) |

TABLE 10-continued

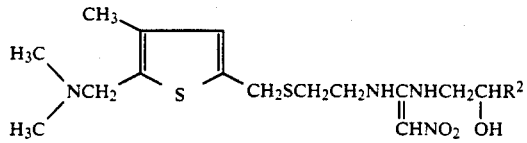

| $R^2$ | Physical properties |
|---|---|
| ![4-methylphenyl] | Melting point: 88–89° C. NMR(CDCl$_3$) δ values: 2.12(9H, s, —CH$_3$×3), 2.34 (3H, s, —CH$_3$), 2.54–2.98(2H, m, >CH$_2$), 3.12–3.75(4H, m, >CH$_2$×2), 3.48(2H, s, >CH$_2$), 3.91(2H, s, >CH$_2$), 4.72–5.08(1H, m, —CH(OH)—), 6.67(1H, s, =CH—), 6.77(1H, s, thiophene ring H), 7.02–7.49(4H, m, benzene ring H×4), 10.28 (1H, bs, >NH) |
| ![4-ethylphenyl] Oily | NMR(CDCl$_3$) δ values: 1.38(3H, t, —CH$_3$), 2.16(9H, s, —CH$_3$×3), 2.40–3.00(4H, m, >CH$_2$×2), 3.10–3.75(4H, m, >CH$_2$×2), 3.49(2H, s, >CH$_2$), 3.91(2H, s, >CH$_2$), 4.95(1H, m, —CH(OH)—), 6.65(1H, s, =CH—), 6.75 (1H, s, thiophene ring H), 7.10–7.41(4H, m, benzene ring H×4), 10.5(1H, bs, >NH) |
| ![3-trifluoromethylphenyl] | Melting point: 109–112° C. |
| ![3-nitrophenyl] | Melting point: 116–118° C. |
| ![4-dimethylaminophenyl] Oily | NMR(CDCl$_3$) δ values: 2.09(9H, s, —CH$_3$×3), 2.40–3.10 (2H, m, >CH$_2$), 2.93 (6H, s, —CH$_3$×2), 3.10–3.75(4H, m, >CH$_2$×2), 3.43(2H, s, >CH$_2$), 3.90(2H, s, >CH$_2$), 4.65–5.00(1H, m, —CH(OH)—), 5.55(1H, bs, —OH), 6.59(1H, s, =CH—), 6.69(1H, s, thiophene ring H), 6.72, 7.27(4H, AA', BB', benzene ring H×4), 10.25(1H, bs, >NH) |
| ![4-propylphenyl]—CH$_2$CH$_2$CH$_3$ Oily | NMR(CDCl$_3$) δ values: 0.90(3H, t, —CH$_3$), 1.20–2.85(2H, m, >CH$_2$), 2.10(9H, s, —CH$_3$×3), 2.30–3.90(4H, m, >CH$_2$×2), 3.10–3.70(4H, m, >CH$_2$×2), 3.41(2H, s, >CH$_2$), 3.85(2H, s, >CH$_2$), 4.85(1H, m, —CH(OH)—), 5.40 (1H, bs, —OH), 6.60(1H, s, =CH—), 6.67(1H, s, thiophene ring H) 7.0–7.50(4H, m, benzene ring H×4) |

TABLE 10-continued

Structure (left column):

CH₃ on thiophene; (CH₃)₂NCH₂– at position 2; –CH₂SCH₂CH₂NHC(=CHNO₂)NHCH₂CHR² with OH on the CHR² carbon at position 5.

| R² | Physical properties |
|---|---|
| 4-CH₃S–C₆H₄– | Melting point: 108–110° C. |
| 4-CH₃S(=O)–C₆H₄– (Oily) | NMR(CDCl₃) δ values: 2.13(3H, s, —CH₃), 2.16(6H, s, —CH₃×2), 2.5–2.95(2H, m, >CH₂), 2.72(3H, s, —SCH₃), 3.1–3.75 (4H, m, >CH₂×2), 3.49(2H, s, >CH₂), 3.81(2H, s, >CH₂), 5.0(1H, m, —CH(OH)—), 6.62(1H, s, =CH—), 6.73(1H, s, thiophene ring H), 7.66(4H, s, benzene ring H×4) |
| 3,4-(OCH₃)₂–C₆H₃– (Oily) | NMR(CDCl₃) δ values: 2.09(9H, s, —CH₃×3), 2.40–2.95 (2H, m, >CH₂), 2.40–4.30(6H, m, >CH₂×3), 3.85(8H, s, —CH₃×2, >CH₂), 4.65–5.10(1H, m, —CH(OH)—), 5.3(1H, bs, —OH), 6.55(1H, s, =CH—), 6.62(1H, s, thiophene ring H), 6.40–7.40(3H, m, benzene ring H×3), 7.60(1H, bs, >NH), 10.35(1H, bs, >NH) |
| 2,3-(OCH₃)₂–C₆H₃– (Oily) | NMR(CDCl₃) δ values: 2.18(9H, s, —CH₃×3), 2.48–2.92 (2H, m, >CH₂), 3.12–4.22(8H, m, >CH₂×4), 3.79(3H, s, —CH₃), 4.79(1H, m, —CH(OH)—), 6.12–7.20 (5H, m, benzene ring H×3, thiophene ring H, =CH—), 10.32 (1H, bs, >NH) |
| 2,5-(OCH₃)₂–C₆H₃– (Oily) | NMR(CDCl₃) δ values: 2.10(9H, s, —CH₃×3), 2.49–2.98 (2H, m, >CH₂), 3.11–4.03(6H, m, >CH₂×3), 3.56(2H, s, >CH₂), 3.83(6H, s, —CH₃×2), 4.93 (1H, bs, —CH(OH)—), 6.53(1H, s, =CH—), 6.55–6.85(4H, m, benzene ring H×3, thiophene ring H), 10.33 (1H, bs, >NH) |
| 2,4,5-(OCH₃)₃–C₆H₂– (Oily) | NMR(CDCl₃) δ values: 2.15(9H, s, —CH₃×3), 2.45–2.96(2H, m, >CH₂), 3.02–4.15 (6H, m, >CH₂×3), 3.48(2H, s, >CH₂), 3.86(9H, s, —CH₃×3), 4.91 (1H, m, —CH(OH)—), 6.33–6.94(4H, m, =CH—, benzene ring H×2, thiophene ring H), 10.26(1H, bs, >NH) |
| 4-CH₃CH₂O–C₆H₄– (Oily) | NMR(CDCl₃) δ values: 1.49(3H, t, —CH₃), 2.09(9H, s, —CH₃×3), 2.49–2.95(2H, m, >CH₂), 3.12–3.70(4H, m, >CH₂×2), 3.46(2H, s, >CH₂), 3.89(2H, s, >CH₂), 4.07(2H, q, —OCH₂CH₃), 4.90(1H, m, —CH(OH)—), 6.63(1H, s, =CH—), 6.74(1H, s, thiophene ring H), 6.89–7.44(4H, m, benzene ring H×4), 10.30(1H, bs, >NH) |
| 4-CH₃S(O)₂–C₆H₄– | Melting point: 119–122° C. |
| 4-Br–C₆H₄– | Melting point: 104–106° C. NMR(CDCl₃) δ values: 2.13(9H, s, —CH₃×3), 2.6–3.0 (2H, m, >CH₂), 3.15–3.7(4H, m, >CH₂×2), 3.49(2H, s, >CH₂), 3.94(2H, s, >CH₂), 5.0(1H, m, —CH(OH)—), 6.67(1H, s, =CH—), 6.79(1H, s, thiophene ring H), 7.25–7.85(4H, m, benzene ring ×4) |

EXAMPLE 3

(1) In a mixture of 60 ml of ethanol and 200 ml of xylene was dissolved 40 g of DL-β-hydroxyphenethylamine, and the resulting solution was added dropwise to a solution of 57.8 g of 1,1-bis(methylthio)-2-nitroethene in 600 ml of xylene under reflux over a period of 1.5 hours to effect reaction. During the reaction, the low-boiling fractions were gradually removed by distillation and the reaction temperature was maintained at 130° C. to 140° C. After completion of the reaction, crystals were deposited with stirring under ice-cooling. The crystals deposited were collected by filtration, dried, and then mixed with 200 ml of a 5% (by weight) aqueous sodium hydroxide solution. After a slight amount of insolubles were removed by filtration, the filtrate was adjusted to pH 6 with a 10% (by weight) aqueous acetic acid solution, and the crystals deposited were collected by filtration and dried to obtain 34 g of 2-nitromethylene-5-phenyloxazolidine having a melting point of 139°–141° C.

On the other hand, the filtrate after the reaction was concentrated, and 50 ml of ethanol was added to the resulting residue, after which the crystals formed were collected by filtration. The crystals obtained were mixed with 25 ml of a 5% (by weight) aqueous sodium hydroxide solution, and the insolubles were removed by filtration. The filtrate was adjusted to pH 6 with 10% by weight aqueous acetic acid solution, and the crystals deposited were collected by filtration and dried to obtain 4.8 g (total yield: 64.5%) of 2-nitromethylene-5-phenyloxazolidine.

NMR (d$_6$-DMSO) δ values: 3.65–4.52 (2H, m, >CH$_2$), 6.05

(1H, t, $\diagdown$CH$\diagup$), 6.80 (1H, s, =CH—), 7.54 (5H, s, benzene ring H×5), 10.1 (1H, bs, >NH)

The following compounds were obtained in the same manner as described above:

5-(3-Methylphenyl)-2-nitromethyleneoxazolidine
Melting point: 96°–97° C.
NMR (CDCl$_3$) δ values: 2.37 (3H, s, —CH$_3$), 3.69–4.50 (2H, m, >CH$_2$), 5.79

(1H, t, $\diagdown$CH$\diagup$), 6.72 (1H, s, =CH—), 6.807–7.55 (4H, m, benzene ring H×4), 9.2 (1H, bs, >NH)

5-(3-Methoxyphenyl)-2-nitromethyleneoxazolidine
Melting point: 105°–107° C.
NMR (d$_6$-DMSO) δ values: 3.64–4.55 (2H, m, >CH$_2$), 3.87 (3H, s, —OCH$_3$), 6.02

(1H, t, $\diagdown$CH$\diagup$), 6.79 (1H, s, =CH—), 6.9–7.65 (4H, m, benzene ring H×4)

5-(4-Fluorophenyl)-2-nitromethyleneoxazolidine
Melting point: 116°–118.5° C.
NMR (d -DMSO) δ values: 3.48–4.56 (2H, m, >CH$_2$), 6.10

(1H, dd, $\diagdown$CH$\diagup$), 6.80 (1H, s, =CH—), 7.20–7.85 (4H, m, benzene ring H×4), 10.06 (1H, bs, >NH)

2-[(Dimethylamino)sulfonyl]imino-5-phenyloxazolidine
Melting point: 95°–98° C.
NMR (d$_6$-DMSO) δ values: 2.71 (6H, s, —CH$_3$×2), 3.48–4.34 (2H, m, >CH$_2$), 5.95

(1H, t, $\diagdown$CH$\diagup$), 7.52 (5H, s, benzene ring H×5), 8.67 (1H, s, >NH)
2-(Methanesulfonyl)imino-5-phenyloxazolidine
Melting point: 120°–122° C.
NMR (d$_6$-DMSO) δ values: 2.95 (3H, s, —CH$_3$), 3.43–4.31 (2H, m, >CH$_2$), 5.98

(1H, t, $\diagdown$CH$\diagup$).

7.53 (5H, s, benzene ring H×5), 8.85 (1H, s, >NH)
2-Cyanoimino-5-phenyloxazolidine
Melting point: 117°–119° C.
NMR (d$_6$-DMSO) δ values: 3.59–4.38 (2H, m, >CH$_2$), 6.08

(1H, t, $\diagdown$CH$\diagup$), 7.58 (5H, s, benzene ring H×5), 9.50 (1H, bs, >NH)
5-(3-Bromophenyl)-2-nitromethylenexozolidine
Melting point: 120°–121° C.
NMR (CDCl ) δ values: 3.76–4.60 (2H, m, >CH$_2$), 5.93

(1H, t, $\diagdown$CH$\diagup$), 6.85 (1H, s, =CH—), 7.39–7.69 (4H, m, benzene ring H×4), 9.30 (1H, bs, >NH)

(2) In 3 ml of ethanol were dissolved 1.5 g of 2-[[5-(dimethlamino)methyl-4-methyl-2-thienyl]methylthio]ethylamine and 1.6 g of 5-(3-methylphenyl)-2-nitromethyleneoxazolidine obtained in above (1), and the resulting solution was subjected to reaction at room temperature for 18 hours. After completion of the reaction, the solvent was removed by distillation under reduced pressure, and the resulting residue was dissolved in 50 ml of ethyl acetate. The resulting solution was washed successively with 30 ml of 1 N aqueous sodium hydroxide solution and 30 ml of a saturated aqueous sodium chloride solution, and dried over anhydrous magnesium sulfate, after which the solvent was removed by distillation under reduced pressure. The resulting residue was purified by a column chromatography (Wako Silica Gel C-200, eluent; chloroform:ethanol=20:1 by volume) to obtain 2.0 g (yield 70%) of N-{2-[[5-(dimethylamino)methyl-4-methyl-2-thienyl]-methylthio]ethyl}-N'-[2-hydroxy-2-(3-methylphenyl)ethyl]-2-nitro-1,1-ethenediamine having a melting point of 88°–89° C.

The physical property (NMR) of this product was identical with that in Example 2.

The following compounds were obtained in the same manner as described above.

N-{2-[[5-(dimethylamino)methyl-4-methyl-2-thienyl]-methylthio]ethyl}-N'-[2-(4-fluorophenyl)-2-hydroxyethyl]-2-nitro-1,1-ethenediamine N-{2-[[5-dimethylamino)methyl-4-methyl-2-thienyl]-methylthio]ethyl}-N'-(8-hydroxyphenethyl)-2-nitro-1,1-ethenediamine N-{2-[[5-(dimethylamino)methyl-4-methyl-2-thienyl]-methylthio]ethyl}-N'-[2-hydroxy-2-(3-methoxyphenyl)ethyl]-2-nitro-1,1-ethenediamine N-[2-(3-bromophenyl)-2-hydroxyethyl]-N'-{2-[[5-dimethylamino)methyl-4-methyl-2-thienyl]methylthio]ethyl}-2-nitro-1,1-ethenediamine N-[2-[[5-(dimethylamino)methyl-4-methyl-2-thienyl]-methylthio]ethyl}-N'-[2-hydroxy-2-(3-trifluoromethylphenyl)ethyl]-2-nitro-1,1-ethenediamine N-[2-(3-chlorophenyl)-2-hydroxyethyl]-N'-{2-[[5-(dimethylamino)methyl-4-methyl-2-thienyl]methylthio]ethyl}-2-nitro-1,1-ethenediamine The physical properties of these compounds were identical with those in Example 2.

EXAMPLE 4

(1) In 35 ml of 21% (by weight) hydrochloric acidisopropanol solution was suspended 2.1 g of thiourea, and 5 g of 5-(dimethylamino)methyl-4-methyl-2-thenyl alcohol was added thereto, after which the resulting mixture was subjected to reaction under reflux for 15 hours. After the mixture was allowed to stand at room temperature, the crystals deposited were collected by filtration to obtain 7 g (yield 82%) of 2-amidinothiomethyl-5-(dimethylamino)methyl-4-methylthiophene dihydrochloride having a melting point of 212°–214° C. (decomp.).

NMR ($d_6$-DMSO) $\delta$ values: 2.31 (3H, s, —CH$_3$), 2.82 (6H, s, —CH×2), 4.58 (2H, s, >CH$_2$), 5.04 (2H, s, >CH$_2$), 7.16 (1H, s, thiophene ring H), 9.76

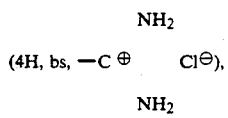

(4H, bs, —C⊕    Cl⊖), 11.01 (1H, bs, HCl)

(2) In 5 ml of water was dissolved 10 g of 2-amidinothiomethyl-5-(dimethylamino)methyl-4-methylthiophene dihydrochloride, and 2.52 g of sodium hydroxide was added thereto, and the resulting mixture was subjected to reaction under reflux for 2.5 hours in a nitrogen atmosphere. The reaction mixture was cooled to room temperature, and then extracted with 100 ml of methylene chloride, and the extract was dried over anhydrous magnesium sulfate, after which the solvent was removed by distillation under reduced pressure. The oily substance thus obtained was distilled under reduced pressure in a nitrogen atmosphere to obtain 5.3 g (yield 83%) of 5-(dimethylamino)methyl-2-mercaptomethyl-4-methylthiophene having a boiling point of 102°–105° C./3 mmHg.

NMR (CDCl$_3$) $\delta$ values: 2.14 (3H, s, —CH$_3$), 2.28 (6H, s, —CH$_3$×2), 3.48 (2H, s, >CH$_2$), 3.85 (2H, s, >CH$_2$), 6.65 (1H, s, thiophene ring H)

(3) In 1 ml of chloroform were dissolved 0.29 g of 1-aziridino-1-methylthio-2-nitroethene and 0.33 g of 5-(dimethylamino)methyl-2-mercaptomethyl-4-methylthiophene obtained in above (2), and the resulting solution was subjected to reaction at room temperature for 4 hours in a nitrogen atmosphere. After completion of the reaction, the solvent was removed by distillation under reduced pressure, and the resulting residue was purified by a column chromatography (Wako Silica Gel C-200, eluent; chloroform:methanol=40:1 by volume) to obtain 0.44 g (yield 64%) of 1-{2-[[5-(dimethylamino)methyl-4-methyl-2-thienyl]methylthio]ethylamino}-1-methylthio-2-nitroethene having a melting point of 69°–71° C.

(4) With 7.5 ml of ethanol were mixed 4.5 g of 1-{2-[[5-(dimethylamino)methyl-4-methyl-2-thienyl]methylthio]ethylamino}-1-methylthio-2-nitroethene and 3.5 g of DL-[2-(3-bromophenyl)-2-hydroxyethyl]amine, and the resulting mixture was subjected to reaction at room temperature for 30 hours. Thereto were added 5 ml of isopropanol and 30 ml of diethyl ether, and the mixture thus obtained was stirred, after which the crystals formed were collected by filtration. The crystals were recrystallized from 40 ml of isopropanol to obtain 4.3 g (yield 65%) of N-[2-(3-bromophenyl)-2-hydroxyethyl]-N'-{2-[[5-dimethylamino)methyl- 4-methyl-2-thienyl]-methylthio]ethyl}-2-nitro-1,1-ethenediamine having a melting point of 104°–106° C.

NMR (CDCl ) $\delta$ values: 2.13 (9H, s, —CH$_3$×3), 2.6–3.0 (2H, m, >CH$_2$), 3.15–3.7 (4H, m, >CH$_2$×2), 3.49 (2H, s, >CH$_2$), 3.94 (2H, s, >CH$_2$), 5.0

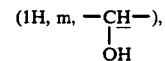

(1H, m, —CH—),
          |
         OH 6.67 (1H, s, =CH—), 6.79 (1H, s, thiophene ring H), 7.25–7.85 (4H, m, benzene ring H×4)

EXAMPLE 5

(1) With 10 ml of ethanol was mixed 1.6 g of 1-methylsulfinyl-1-methylthio-2-nitroethene, and 1.2 g of 2-chloroethylamine hydrochloride was then added thereto, after which 1.0 g of triethylamine was added dropwise at −20° C. in a nitrogen atmosphere. After they were subjected to reaction at the same temperature for 2 hours and then gradually heated to room temperature. After completion of the reaction, the solvent was removed by distillation under reduced pressure, and 20 ml of ethyl acetate was added to the resulting residue, after which the resulting mixture was washed with water and dried over anhydrous magnesium sulfate, and the solvent was removed by distillation under reduced pressure to obtain 1.0 g (yield 54.8%) of 1-(2-chloroethyl)amino-1-methylthio-2-nitroethene having a melting point of 115°–117° C.

(2) In 5 ml of methanol was dissolved 0.5 g of 1-(2-chloroethyl)amino-1-methylthio-2-nitroethene obtained in above (1), and 0.55 g of DL-[2-hydroxy-2-(3-methoxyphenylethyl]amine was added thereto, after which the resulting mixture was allowed to stand at room temperature for 24 hours. The mixture was concentrated under reduced pressure, and 20 ml of ethyl acetate was added to the resulting residue, after which the thus obtained mixture was washed with 5% (by weight) hydrochloric acid and dried over anhydrous magnesium sulfate. Thereafter, the solvent was removed by distillation. The residue thus obtained was purified by a column chromatography (Wako Silica Gel C-200, eluent; chloroform:ethanol=20:1 by volume) to obtain 0.448 g (yield 52%) of N-(2-chloroethyl)-N'-[2-hydroxy-2-(3-methoxyphenyl)ethyl]-2-nitro-1,1-ethenediamine having a melting point of 127°–130° C.

NMR (CDCl$_3$) $\delta$ values: 3.0–4.0 (6H, m, >CH$_2$×3), 3.77 (3H, s, —CH$_3$), 4.6–5.2

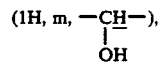

(1H, m, —CH—),
          |
         OH 6.60 (1H, s, =CH—), 6.4–7.8 (4H, m, benzene ring H×4)

The following compound was obtained in the same manner as described above.

N-(2-chloroethyl)-N'-($\beta$-hydroxyphenyl)-2-nitro-1,1-ethenediamine

Melting point: 130°-131° C.

NMR (d<sub>6</sub>DMSO) δ values: 2.98-3.88 (6H, m, >CH<sub>2</sub>×3), 4.71

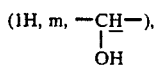
(1H, m, —CH—),
            |
           OH 5.82 (1H, bs, —OH), 6.59 (1H, s, =CH—), 7.36 (5H, s, benzene ring H×5), 10.34 (1H, bs, >NH)

(3) In a mixture of 1.2 ml of ethanol and 1.2 ml of water was dissolved 0.3 g of 2-amidinothiomethyl-5-(dimethylamino)methyl-4-methylthiophene dihydrochloride, and 0.3 g of N-(2-chloroethyl)-N'-2-hydroxy-2-(3-methoxyphenyl)ethyl]-2-nitro-1,1-ethenediamine obtained in above (2) was added at one time at −10° C. in a nitrogen atmosphere, after which 1 ml of a 12% (by weight) aqueous sodium hydroxide solution was added dropwise. After the addition, the resulting mixture was subjected to reaction at room temperature for 1 hour. After completion of the reaction, the solvent was removed by distillation under reduced pressure, and 5 ml of ethanol was added to the resulting residue. The mixture thus obtained was stirred, after which the insolubles were removed by filtration. The solvent was removed by distillation under reduced pressure, and the resulting residue was purified by a column chromatography (basic alumina, eluent: chloroform) to obtain 0.01 g (yield 2%) of oily N-{2-[[5-(dimethylamino)methyl-4-methyl-2-thienyl]methylthio]ethyl}-N'-[ 2-hydroxy-2-(3-methoxyphenyl)ethyl]-2-nitro-1,1-ethenediamine.

The physical property (NMR) of this compound was identical with that in Example 2.

(4) In 5 ml of methanol was dissolved 0.14 g of 5-(dimethylamino)methyl-2-mercaptomethyl-4-methyl-thiophene, and 0.2 ml of a 3.57 N sodium methoxidemethanol solution was added at room temperature in a nitrogen atmosphere, after which 0.2 g of N-(2-chloroethyl)-N'-(β-hydroxyphenethyl)-2-nitro-1,1-ethenediamine was added at one time, after which the reaction mixture was allowed to stand at room temperature for 24 hours, and the deposited substance was removed by filtration, after which the solvent was removed by distillation under reduced pressure. Chloroform was added to the resulting residue, and the insolubles were removed by filtration, after which the solvent was removed by distillation under reduced pressure, and the residue thus obtained was purified by a column chromatography (basic alumina, eluent; chloroform:methanol = 10:1 by volume) to obtain 0.033 g (yield 11%) of N-{2-[[5-(dimethylamino)methyl-4-methyl-2-thienyl-methylthio]ethyl}-N'-(3-hydroxyphenethyl)-2-nitro-1,1-ethenediamine having a melting point of 114°-115° C.

The following compounds were obtained in the same manner as described above.

N-{2-[[5-(dimethylamino)methyl-4-methyl-2-thienyl]-methylthio]ethyl}-N'-2-(4-fluorophenyl)-2-hydroxyethyl-2-nitro-1,1-ethenediamine N-{2-[[5-(dimethylamino)methyl-4-methyl-2-thienyl]-methylthio]ethyl}-N'-[2-hydroxy-2-(3-methylphenyl)ethyl]-2-nitro-1,1-ethenediamine N-[2-(3-bromophenyl)-2-hydroxyethyl]-N'-{2-[[5-(dimethylamino)methyl-4-methyl-2-thienyl]methyl-thio]ethyl}-2-nitro-1,1-ethenediamine N-{2-[[5-(dimethylamino)methyl-4-methyl-2-thienyl]-methylthio]ethyl}-N'-[2-hydroxy-2-(3-trifluoromethylphenyl)ethyl]-2-nitro-1,1-ethenediamine N-[2-(3-chlorophenyl)-2-hydroxyethyl]-N'-{2-[[5-(dimethylamino)methyl-4-methyl-2-thienyl]methyl-thio]ethyl}-2-nitro-1,1-ethenediamine The physical properties of these compounds were identical with those in Example 2.

EXAMPLE 6

(1) In 50 ml of anhydrous ethanol was suspended 9.3 g of 1-methylsulfinyl-1-methylthio-2-nitroethene, and the resulting suspension was stirred. A solution of 9.3 g of DL-[2-hydroxy-2-(3-methylphenyl)ethyl]amine in 5 ml of ethanol was added thereto dropwise at −10° C. to 0° C. over a period of 30 minutes in a nitrogen atmosphere. After the addition, the resulting mixture was stirred at the same temperature for 1.5 hours, and the crystals deposited were collected by filtration, washed with 10 ml of ethanol, and then dried to obtain 7.0 g (yield 50.8%) of 1-{[2-hydroxy-2-(3-methylphenyl)ethyl]amino}-1-methylthio-2-nitroethene having a melting point of 99°-101° C.

NMR (CDCl<sub>3</sub>) δ values: 2.38 (6H, s, —CH<sub>3</sub>×2), 3.2-3.9 (2H, m, >CH<sub>2</sub>), 4.3 (1H, bs, —OH), 5.02

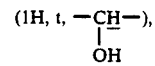
(1H, t, —CH—),
            |
           OH 6.62 (1H, s, =CH—), 7.27 (4H, s, benzene ring H×4), 10.7 (1H, bs, >NH)

The following compounds were obtained in the same manner as described above.

1-{[2-(4-Fluorophenyl)-2-hydroxyethyl]amino}-1-methylthio-2-nitroethene
Melting point: 152°-154° C.

1-{[2-Hydroxy-2-(3-methoxyphenyl)ethylamino}-1-methylthio-2-nitroethene
Melting point: 148°-149.5° C.

(2) In 1 ml of dioxane were suspended 0.5 g of 2-{[5-dimethylamino)methyl-4-methyl-2-thienyl]methylthi-o}ethylamine and 0.5 g of 1-{[2-hydroxy-2-(3-methylphenyl)ethyl]amino}-1-methylthio-2-nitroethene obtained in above (1), and the resulting suspension was subjected to reaction at room temperature for 3 hours. After completion of the reaction, the solvent was removed by distillation under reduced pressure, and the obtained oily substance was purified by a column chromatography (Wako Silica Gel C-200, eluent; chloroform:methanol=20:1 by volume) to obtain 0.7 g (yield 80%) of N-{2-[[5-(dimethylamino)methyl-4-methyl-2-thienylmethylthio]ethyl}-N'-[2-hydroxy-2-(3-methylphenyl)ethyl]-2-nitro-1,1-ethenediamine having a melting point of 88°-89° C.

The physical property (NMR) of this product was identical with that in Example 2.

The following compounds were obtained in the same manner as described above.

N-{2-[[5-(dimethylamino)methyl-4-methyl-2-thienyl]-methylthio]ethyl}-N'-[2-(4-fluorophenyl)-2-hydroxyethyl]-2-nitro-1,1-ethenediamine N-{2-[[5-(dimethylamino)methyl-4-methyl-2-thienyl]-methylthio]ethyl}-N'-(3-hydroxyphenethyl)-2- nitro-1,1-ethenediamine N-{2-[[5-(dimethylamino)methyl-4-methyl-2-thienyl]-methylthio]ethyl}-N'-[2-hydroxy-2-(3-methoxyphenyl)ethyl]-2-nitro-1,1-ethenediamine N-[2-(3-bromophenyl)-2-hydroxyethyl]-N'-{2-[[5-(dimethylamino)methyl-4-methyl-2-thienyl]methyl-thio]ethyl}-2-nitro-1,1-ethenediamine N-[2-[[5-(dimethylamino)methyl-4-methyl-2-thienyl]-methylthio]ethyl}-N'-[2-hydroxy-2-(3-trifluoromethylphenyl)ethyl]-2-nitro-1,1-ethenediamine N-[2-(3-chlorophenyl)-2-hydroxyethyl]-N'-{2-[[5-(dimethylamino)methyl-4-methyl-2-thienyl]methylthio]ethyl}-2-nitro-1,1-ethenediamine The physical properties of these compounds were identical with those in Example 2.

EXAMPLE 7

(1) In 16 ml of N,N-dimethylformamide were dissolved 6.5 g of 1-{[2-hydroxy-2-(3-methylphenyl)ethyl]amino}-1-methylthio- 2-nitroethene, 5.1 g of (tert.-butyl)dimethylsilyl chloride and 2.3 g of imidazole, and the resulting solution was subjected to reaction at room temperature for 20 hours. After completion of the reaction, 100 ml of chloroform and 50 ml of water were added thereto, and the organic layer was separated. The organic layer was washed with 50 ml of a saturated aqueous sodium chloride solution and dried over anhydrous magnesium sulfate, after which the solvent was removed by distillation under reduced pressure to obtain 9.0 g (yield 97%) of oily 1-[2-(tert.-butyl)dimethylsilyoxy-2-(3-methylphenyl)ethyl]amino-1-methylthio-2-nitroethene.

NMR (CDCl$_3$) δ values:
−0.11 (3H, s, —CH$_3$), 0.09 (3H, s, —CH$_3$), 0.91 (9H, s, —CH$_3$×3), 2.38 (3H, s, —CH$_3$), 2.42 (3H, s, —CH$_3$), 3.64 (2H, dd, >CH$_2$), 4.95

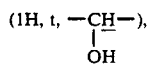

6.67 (1H, s, =CH—), 7.30 (4H, s, benzene ring H×4), 10.69 (1H, bs, >NH)

The following compound was obtained in the same manner as described above.

1-{[2-(Tert.-butyl)dimethylsilyoxy-2-(4-fluorophenyl)ethyl]amino}-1-methylthio-2-nitroethene Melting point: 111°–113° C.

(2) In 10 ml of water was dissolved 4.4 g of silver nitrate, and 26 ml of a 1 N aqueous sodium hydroxide solution was added with stirring, followed by adding thereto 1.2 g of ethyleneimine. A solution of 7.69 g of 1-{[2-(tert.-butyl)dimethylsilyloxy-2-(3-methylphenyl)ethyl]amino}-1-methylthio-2-nitroethene in 30 ml of chloroform was added dropwise at 25° C. to 30° C. over a period of 10 minutes. The resulting mixture was stirred at the same temperature for 2 hours, after which the insolubles were removed by filtration, and the organic layer was separated. The organic layer was dried over anhydrous magnesium sulfate and concentrated, after which 25 ml of n-hexane was added to the resulting residue, and the resulting mixture was stirred. The crystals deposited were collected by filtration and dried to obtain 5.45 g (yield 81.3%) of 1-aziridino-1-{[2-(tert.-butyl)dimethylsilyloxy-2-(3-methylphenyl)ethyl]amino:-2-nitroethene having a melting point of 96°–98° C.

NMR (CDCl$_3$) δ values: −0.11 (3H, s, —CH$_3$), 0.10 (3H, s, —CH$_3$), 0.94 (9H, s, —CH$_3$×3), 2.19 (4H, s, >CH$_2$×2), 2.38 (3H, s, —CH$_3$), 3.68 (2H, dd, >CH$_2$), 4.94

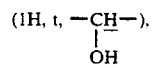

6.56 (1H, s, =CH—), 7.27 (4H, s, benzene ring H×4), 10.3 (1H, bs, >NH)

The following compound was obtained in the same manner as described above.

1-Aziridino-1-{[2-(tert.-butyl)dimethylsilyloxy-2-(4-fluorophenyl)ethyl]amino}-2-nitroethene Melting point: 97°–99° C.

(3) A solution of 1.0 g of 5-(dimethylamino)methyl-2-mercaptomethyl-4-methylthiophene in 10 ml of methanol was added to 20 ml of methanol in a nitrogen atmosphere, and a solution of 1.74 g of 1-aziridino-1-{[2-(tert.-butyl)dimethylsilyloxy-2-(3-methylphenyl)ethyl]amino}-2-nitroethene obtained in above (2) in 10 ml of methanol was then added dropwise at room temperature over a period of 10 minutes. The resulting solution was subjected to reaction with stirring at the same temperature for 1 hour. After completion of the reaction, the reaction mixture was concentrated under reduced pressure, and the resulting residue was purified by a column chromatography (Wako Silica Gel C-200, eluent; chloroform:ethanol=30:1 by volume) to obtain 2.24 g (yield 85.4%) of oily N-[2-(tert.-butyl)dimethylsilyloxy-2-(3-methylphenyl)ethyl]-N'-{2-[[5-(dimethylamino)methyl-4-methyl-2-thienyl]methylthio]ethyl}-2-nitro-1,1-ethenediamine.

NMR (CDCl$_3$) δ values: −0.10 (3H, s, —CH$_3$), 0.04 (3H, s, —CH$_3$), 0.99 (9H, s, —CH$_3$×3), 2.13 (3H, s, —CH$_3$), 2.24 (6H, s, —CH$_3$×2), 2.35 (3H, s, —CH$_3$), 2.74 (2H, t, >CH$_2$), 3.0–3.8 (4H, m, >CH$_2$×2), 3.51 (2H, s, >CH$_2$), 3.89 (2H, s, >CH$_2$), 4.93

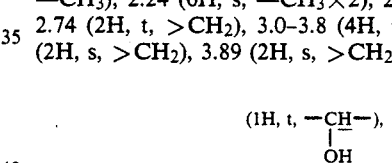

6.67 (1H, s, =CH—), 6.73 (1H, s, thiophene ring H), 7.24 (4H, s, benzene ring H×4), 10.4 (1H, bs, >NH)

(4) In 10 ml of tetrahydrofuran was dissolved 0.93 g of N-[2-(tert.-butyl)dimethylsilyloxy-2-[3-methylphenylethyl]-N'-{2-[[5-(dimethylamino)methyl-4-methyl-2-thienyl]methylthio]ethyl}-2-nitro-1,1-ethenediamine, obtained in above (3), and 0.84 g of tetra(n-butyl)ammonium fluoride was added at 0° C. to 5° C., after which the resulting mixture was subjected to reaction at the same temperature for 5 minutes and then at room temperature for 15 minutes. After completion of the reaction, the solvent was removed by distillation under reduced pressure, and 10 ml of water and 10 ml of ethyl acetate were added to the resulting residue, after which the organic layer was separated. The organic layer was washed with 10 ml of a saturated aqueous sodium chloride solution and dried over anhydrous magnesium sulfate, after which the solvent was removed by distillation under reduced pressure. The thus obtained residue was purified by a column chromatography (Wako Silica Gel C-200, eluent; chloroform ethanol =20:1 by volume) to obtain 0.58 g (yield 78%) of N-{2-[[5-(dimethylamino)methyl-4-methyl-2-thienyl]methylthio]ethyl}-N'-[2-hydroxy-2-(3-methylphenyl)ethyl]-2-nitro-1,1-ethenediamine having a melting point of 88°–89° C.

The physical property (NMR) of this product was identical with that in Example 2.

The following compounds were obtained in the same manner as described above.

N-{2-[[5-(dimethylamino)methyl-4-methyl-2-thienyl]-methylthio]ethyl}-N'-[2-(4-fluorophenyl)-2-hydroxyethyl]-2-nitro-1,1-ethenediamine N-{2-[[5-(dimethylamino)methyl-4-methyl-2-thienyl]-methylthio]ethyl}-N'-(β-hydroxyphenethyl)-2-nitro-1,1-ethenediamine N-{2-[[5-(dimethylamino)methyl-4-methyl-2-thienyl]-methylthio]ethyl}-N'-{2-hydroxy-2-(3-methoxyphenyl)ethyl]-2-nitro-1,1-ethenediamine N-[2-(3-bromophenyl)-2-hydroxyethyl]-N'-{2-[[5-(dimethylamino)methyl-4-methyl-2-thienyl]methylthio]ethyl}-2-nitro-1,1-ethenediamine N-{2-[[5-dimethylamino)methyl-4-methyl-2-thienyl]-methylthio]ethyl}-N'-[2-hydroxy-2-(3-trifluoromethylphenyl)ethyl]-2-nitro-1,1-ethenediamine N-[2-(3-chlorophenyl)-2-hydroxyethyl]-N'-{2-[[5-(dimethylamino)methyl-4-methyl-2-thienyl]methylthio]ethyl}-2-nitro-1,1-ethenediamine The physical properties of these compounds were identical with those in Example 2.

EXAMPLE 8

(1) In a nitrogen stream, 4.6 g of sodium hydride (52% purity) was suspended in 50 ml of N,N-dimethylformamide, and 7.7 g of cysteamine was added in small portions with stirring under ice-cooling. After the addition, the resulting mixture was subjected to reaction at room temperature for 1 hour. To reaction mixture thus obtained was added dropwise 7.58 ml of chloromethyl methyl ether with ice-cooling, and after the addition, the resulting mixture was stirred at the same temperature for 1 hour and then at room temperature for 30 minutes. The insolubles were removed by filtration and the thus obtained N,N-dimethylformamide solution containing 2-(methoxymethylthio)ethylamine was added dropwise to a solution of 25.0 g of 1,1-bis(methylthio)-2-nitroethene in 100 ml of acetonitrile under reflux over a period of 45 minutes. After the addition, the resulting mixture was refluxed for 30 minutes, and the solvent was removed by distillation under reduced pressure, after which 50 ml of ethanol was added to the resulting residue, and the thus obtained mixture was stirred. The insolubles were removed by filtration and the solvent was removed by distillation under reduced pressure, after, which the resulting residue was purified by a column chromatography (Wako Silica Gel C-200, eluent; benzene:ethyl acetate = 10:1 by volume), and the crystals thus obtained were washed with 30 ml of diisopropyl ether and then dried to obtain 11.5 g (yield 48%) of 1-methylthio-1-[(2-methoxymethylthio)ethylamino]-2-nitroethene having a melting point of 54°-58° C.

NMR (CDCl₃) δ values: 2.50 (3H, s, —CH₃), 2.92 (2H, t, >CH₂), 3.43 (3H, s, —OCH₃), 3.77 (2H, m, >CH₂), 4.74 (2H, s, >CH₂), 6.70 (1H, s, =CH—), 10.7 (1H, bs, >NH)

(2) With 15 ml of ethanol were mixed 7.5 g of the 1-methylthio-1-[(2-methoxymethylthio)ethylamino]-2-nitroethene and 5.6 g of DL-β-hydroxyphenethylamine, and the resulting mixture was stirred at room temperature for 8 hours, and then allowed to stand overnight at room temperature. The solvent was removed by distillation under reduced pressure, and the crystals thus obtained were washed with 15 ml of isopropanol and then dried to obtain 7.3 g (yield 71%) of N-(β-hydroxyphenethyl)-N'-[2-methoxymethylthio)ethyl]-2-nitro-1,1-ethenediamine having a melting point of 107°-109.5° C.

NMR (CDCl₃) δ values: 2.76 (2H, t, >CH₂), 3.1-3.7 (4H, m, >CH₂×2), 3.30 (3H, s, —OCH₂), 4.59 (2H, s, >CH₂), 4.9

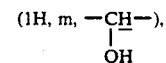

(1H, m, —CH—),
       |
      OH 6.60 (1H, s, =CH—), 7.38 (5H, s, benzene ring H×5)

(3) With 5 ml of anhydrous methylene chloride was mixed 1.45 ml of a boron trifluoride-acetic acid complex compound [containing about 40% (by weight) of boron trifluoride], and a solution of 0.46 g of 2-(dimethylamino)methyl- 3-methylthiophene and 1.2 g of the N-(β-hydroxyphenethyl)-N'-[2-(methoxymethylthio)ethyl]-2-nitro-1,1-ethenediamine obtained in above (2) in 10 ml of anhydrous methylene chloride was added dropwise thereto at 10° to 13° C. over a period of 30 minutes. After the addition, the resulting mixture was stirred at room temperature for 40 minutes, and the solution thus obtained was added to 10 ml of ice water, followed by adding thereto 20 ml of chloroform. The resulting mixture was adjusted to pH 9 to 10 with anhydrous potassium carbonate, and the insolubles were removed by filtration. The organic layer was separated and then extracted with 18 ml of 0.5 N hydrochloric acid, after which the extract was adjusted to pH 9 to 10 with anhydrous potassium carbonate, and extracted with 30 ml of chloroform. The thus obtained organic layer was washed with 10 ml of a saturated aqueous sodium chloride solution, and the solvent was removed by distillation under reduced pressure, after which the resulting residue was purified by a column chromatography (Wako Silica Gel C-200, eluent; chloroform:ethanol = 20:1 by volume), and crystallized from an isopropanol-diethyl ether solution to obtain 0.14 g (yield 10%) of N-{2-[[5-(dimethylamino)methyl-4-methyl-2-thienyl]methylthio]ethyl}-N'-(β-hydroxyphenethyl)-2-nitro-1,1-ethenediamine having a melting point of 114°-115° C.

The physical property (NMR) of this product was identical with that in Example 2.

The following compounds were obtained in the same manner as described above.

N-{2-[[5-(dimethylamino)methyl-4-methyl-2-thienyl]-methylthio]ethyl}-N'-[2-(4-fluorophenyl)-2-hydroxyethyl]-2-nitro-1,1-ethenediamine N-{2-[[5-(dimethylamino)methyl-4-methyl-2-thienyl]-methylthio]ethyl}-N'-[2-hydroxy-2-(3-methoxyphenylethyl]-2-nitro-1,1-ethenediamine N-{2-[[5-(dimethylamino)methyl-4-methyl-2-thienyl]-methylthio]ethyl}-N'-[2-hydroxy-2-(3-methylphenyl)ethyl]-2-nitro-1,1-ethenediamine N-[2-(3-bromophenyl)-2-hydroxyethyl]-N'-{2-[[5-(dimethylamino)methyl-4-methyl-2-thienyl]-methylthio]ethyl}-2-nitro-1,1-ethenediamine N-{2-[[5-(dimethylamino)methyl-4-methyl-2-thienyl]-methylthio]ethyl}-N'-[2-hydroxy-2-(3-trifluoromethylphenyl)ethyl]-2-nitro-1,1-ethenediamine N-[2-(3-chlorophenyl)-2-hydroxyethyl]-N'-{2-[[5-(dimethylamino)methyl-4-methyl-2-thienyl]methylthio]ethyl}-2-nitro-1,1-ethenediamine The physical properties of these compounds were identical with those in Example 2.

EXAMPLE 9

In a mixed solvent of 20 ml of methylene chloride and 10 ml of methanol was dissolved 2.4 g of 5-(3-methoxyphenyl)-2-nitromethyleneoxazolidine at room temperature, and a solution of 2.0 g of 5-(dimethylamino) methyl-2-mercaptomethyl-4-methylthiophene in 5 ml of methanol was added thereto in a nitrogen atmosphere. Then, the solution of 0.5 g of ethyleneimine in 5 ml of methanol was added dropwise at the same temperature over a period of 10 minutes. After addition, the resulting solution was subjected to reaction with stirring for 5 hours. After the completion of the reaction, the solvent was removed by distillation under reduced pressure, and the residue obtained was purified by a column chromatography (Wako Silica Gel C-200, eluent; chloroform : ethanol=30:1 by volume) to obtain 4.0 g (yield 83.5%) of oily N-{2-[[5-(dimethylamino)methyl-4-methyl-2-thienyl]methylthio]ethyl'-N'-[2-(3-methoxyphenyl)-2-hydroxyethyl]-2-nitro-1,1-ethenediamine.

The physical property (NMR) of this product was identical with that in Example 2.

The following compounds were obtained in the same manner as described above.

N-{2-[[5-(dimethylamino)methyl-4-methyl-2-thienyl]-methylthio]ethyl}-N'-[2-(4-fluorophenyl)-2-hydroxyethyl]-2-nitro-1,1-ethenediamine N-{2-[[5-(dimethylamino)methyl-4-methyl-2-thienyl]-methylthio]ethyl}-N'-(8-hydroxyphenethyl)-2-nitro-1,1-ethenediamine N-{2-[[5-(dimethylamino)methyl-4-methyl-2-thienyl]-methylthio]ethyl}-N'-[2-hydroxy-2-(3-methylphenylethyl]-2-nitro-1,1-ethenediamine N-[2-(3-bromophenyl)-2-hydroxyethyl]-N'-{2-[[5-(dimethylamino)methyl-4-methyl-2-thienyl]methylthio]ethyl}-2-nitro-1,1-ethenediamine N-{2-[[5-(dimethylamino)methyl-4-methyl-2-thienyl]-methylthio]ethyl}-N'-[2-hydroxy-2-(3-trifluoromethylphenylethyl]-2-nitro-1,1-ethenediamine N-[2-(3-chlorophenyl)-2-hydroxyethyl]-N'-2-[[5-(dimethylamino)methyl-4-methyl-2-thienyl]-methylthio]ethyl}-2-nitro-1,1-ethenediamine The physical properties of these compounds were identical with those in Example 2.

EXAMPLE 10

(1) In 150 ml of N,N-dimethylformamide was suspended 4.8 g of sodium hydride (52% purity), and 20.0 g of 3-piperidinomethylphenol was added in small portions with stirring under ice-cooling. After the addition, the resulting mixture was subjected to reaction at room temperature for 1 hour. To the reaction mixture thus obtained was added 28.0 g of N-(3-bromopropyl)phthalimide, and the resulting mixture was subjected to reaction for 24 hours. After completion of the reaction, the solvent was removed by distillation under reduced pressure, and 300 ml of water and 300 ml of chloroform were added to the resulting residue to dissolve the same. The organic layer was separated and then dried over anhydrous magnesium sulfate, after which the solvent was removed by distillation under reduced pressure to obtain 35.0 g (yield 88.5%) of oily N-[3-(3-piperidinomethylphenoxy)propyl]phthalimide.

(2) In 200 ml of ethanol was dissolved 29.3 g of the N-[3-(3-piperidinomethylphenoxy)propyl]phthalimide obtained in above (1), and 23.1 ml of hydrazine hydrate was added with stirring at room temperature, after which the resulting mixture was subjected to reaction at the same temperature for 24 hours. After completion of the reaction, the solvent was removed by distillation under reduced pressure, and 300 ml of toluene was added to the resulting residue, after which azeotropic dehydration was carried out. Thereafter, 500 ml of chloroform was added, and the insolubles were removed by filtration. The solvent was removed by distillation under reduced pressure to obtain 16.1 g (yield 84%) of oily 3-(3-piperidinomethylphenoxy)propylamine.

(3) With 100 ml of acetonitrile were mixed 16.0 g of the 3-(3-piperidinomethylphenoxy)propylamine obtained in above (2) and 21.3 g of 1,1-bis(methylthio)-2-nitroethene, and the resulting mixture was subjected to reaction under reflux for 2 hours. After completion of the reaction, the solvent was removed by distillation under reduced pressure, and 100 ml of ethanol was added to the resulting residue, after which the insolubles were removed by filtration. The solvent was removed by distillation under reduced pressure, and the resulting residue was purified by a column chromatography (Wako Silica Gel C-200, eluent chloroform:methanol=20:1 by volume) to obtain 18.0 g (yield 76.3%) of 1-methylthio-2-nitro-1-[3-(3-piperidinomethylphenoxy)propylamino]ethene having a melting point of 68°-69.5° C.

NMR (CDCl$_3$) δ values: 1.16–1.83 (6H, m, >CH$_2$×3), 1.89–2.53 (6H, m, >CH$_2$×3), 2.42 (3H, s, —SCH$_3$), 3.47 (2H, s, >CH$_2$), 3.69 (2H, td, >CH$_2$), 4.11 (2H, t, >CH$_2$), 6.62 (1H, s, =CH—), 6.75–7.43 (4H, m, benzene ring H×4), 10.61 (1H, bs, >NH)

(4) In 43 ml of ethanol were dissolved 8.5 g of the 1-methylthio-2-nitro-1-[3-(3-piperidinomethylphenoxy)propylamino]ethene obtained in above (3) and 10.8 g of DL-[2-(4-fluorophenyl)-2-hydroxyethyl]amine, and the resulting solution was subjected to reaction under reflux for 2 hours. After completion of the reaction, the solvent was removed by distillation under reduced pressure, and the resulting residue was purified by a column chromatography (Wako Silica Gel C-200, eluent; chloroform:methanol=10:1 by volume) to obtain 8.03 g (yield 73%) of N-[2-(4-fluorophenyl)-2-hydroxyethyl]-2-nitro-N'-[3-(3-piperidinomethylphenoxy)propyl]-1,1-ethenediamine having a melting point of 135°-136° C.

Elementary analysis values (for C$_{25}$H$_{33}$FN$_4$O$_4$): Calculated (%): C; 63.54, H; 7.04, N; 11.86 Found (%): C; 63.80, H; 7.33, N; 11.78

The compounds listed in Table 11 were obtained in the same manner as described above.

TABLE 11

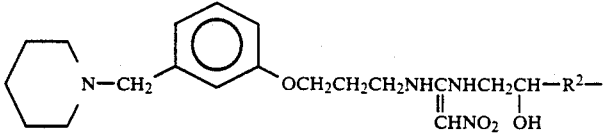

| R² | Physical properties |
|---|---|
| 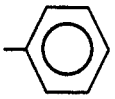<br>Oily | NMR (d₆-DMSO) δ values: 1.07–1.68 (6H, m, >CH₂ × 3), 1.68–2.48 (6H, m, >CH₂ × 3), 3.08–3.64 (6H, m, >CH₂ × 3), 4.07 (3H, m, >CH₂, —OH), 4.88 (1H, m, —C$\underline{H}$—), 5.93 (1H, bs, >NH),<br>                   OH<br>6.68 (1H, s, =CH—), 6.8–7.7 (9H, m, benzene ring H × 9), 10.42 (1H, bs, >NH) |
| 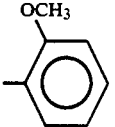<br>Oily | NMR (CDCl₃) δ values: 1.05–1.76 (6H, m, >CH₂ × 3), 1.76–2.54 (6H, m, >CH₂ × 3), 3.05–3.71 (6H, m, >CH₂ × 3), 3.88 (3H, s, —CH₃), 4.11 (2H, m, >CH₂), 5.25 (2H, m, —OH, —C$\underline{H}$—),<br>                   OH<br>6.62–7.75 (9H, m, =CH—, benzene ring H × 8), 10.35 (1H, bs, >NH) |
| 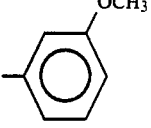<br>Oily | NMR (CDCl₃) δ values: 1.06–1.75 (6H, m, >CH₂ × 3), 1.76–2.51 (6H, m, >CH₂ × 3), 3.08–3.65 (6H, m, >CH₂ × 3), 3.76 (3H, s, —CH₃), 4.06 (2H, m, >CH₂), 4.86 (1H, m, —C$\underline{H}$—), 6.62<br>                   OH<br>(1H, s, =CH—), 6.69–7.45 (8H, m, benzene ring H × 8), 10.38 (1H, bs, >NH) |
| 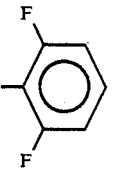<br>Oily | NMR (CDCl₃) δ values: 1.10–1.71 (6H, m, >CH₂ × 3), 1.80–2.50 (6H, m, >CH₂ × 3), 3.00–3.80 (6H, m, >CH₂ × 3), 4.08 (2H, m, >CH₂), 5.35 (1H, m, —C$\underline{H}$—), 6.58 (1H, s, =CH—),<br>                   OH<br>6.66–7.85 (7H, m, benzene ring H × 7) |
| 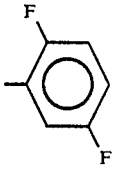 | Melting point: 163–164° C. |
| 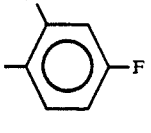 | Melting point: 135–139° C. |
| 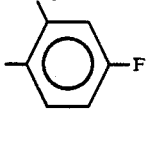 | Melting point: 133–134° C. |
| 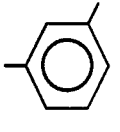<br>Oily | NMR (CDCl₃) δ values: 1.03–1.59 (6H, m, >CH₂ × 3), 1.74–2.54 (6H, m, >CH₂ × 3), 3.05–3.77 (6H, m, >CH₂ × 3), 4.04 (2H, m, >CH₂), 4.84 (1H, m, —C$\underline{H}$—), 6.55 (1H, s, =CH—),<br>                   OH<br>6.64–7.34 (8H, m, benzene ring H × 8), 10.32 (1H, bs, >NH) |

TABLE 11-continued

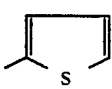

| $R^2$ | Physical properties |
|---|---|
| 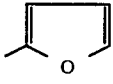<br>Oily | NMR (CDCl$_3$) δ values: 1.15-1.77 (6H, m, >CH$_2$ × 3), 1.77-2.52 (6H, m, >CH$_2$ × 3), 3.00-3.71 (6H, m, >CH$_2$ × 3), 4.09 (2H, m, >CH$_2$), 5.19 (1H, m, —C$\underline{H}$—), 6.65 (1H, s, =CH—),<br>               OH<br>6.7-7.4 (7H, m, benzene ring H × 4, thiophene ring H × 3) |
| 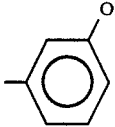<br>Oily | NMR (CDCl$_3$) δ values: 1.05-1.64 (6H, m, >CH$_2$ × 3), 1.73-2.50 (6H, m, >CH$_2$ × 3), 3.05-3.74 (6H, m, >CH$_2$ × 3), 4.02 (2H, m, >CH$_2$), 4.86 (1H, m, —C$\underline{H}$—), 6.35 (2H, s, furan ring<br>               OH<br>H × 2), 6.58 (1H, s, =CH—), 6.65-7.74 (5H, m, benzene ring H × 4, furan ring H), 10.38 (1H, bs, >NH) |
| 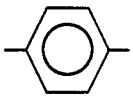<br>Oily | NMR (d$_6$-DMSO) δ values: 1.08-1.77 (6H, m, >CH$_2$ × 3), 1.80-2.68 (6H, m, >CH$_2$ × 3), 3.08-3.78 (6H, m, >CH$_2$ × 3), 4.09 (2H, m, >CH$_2$), 4.78 (1H, m, —C$\underline{H}$—), 6.70 (1H, s, =CH—),<br>               OH<br>6.80-7.58 (8H, m, benzene ring H × 8), 10.27 (1H, bs, >NH) |
| <br>Oily | NMR (CDCl$_3$) δ values: 1.06-1.77 (6H, m, >CH$_2$ × 3), 1.79-2.52 (6H, m, >CH$_2$ × 3), 3.05-3.65 (6H, m, >CH$_2$ × 3), 3.80 (3H, s, —CH$_3$), 4.10 (2H, m, >CH$_2$), 4.91 (1H, m, —C$\underline{H}$—), 5.20<br>               OH<br>(1H, bs, —OH), 6.70 (1H, s, =CH—), 6.75-7.58 (8H, m, benzene ring H × 8), 10.19 (1H, bs, >NH) |
| <br>Oily | NMR (CDCl$_3$) δ values: 1.10-1.71 (6H, m, >CH$_2$ × 3), 1.30-2.42 (6H, m, >CH$_2$ × 3), 2.35 (3H, s, —CH$_3$), 3.04-3.71 (6H, m, >CH$_2$ × 3), 4.11 (2H, m, >CH$_2$), 4.89 (1H, m, —C$\underline{H}$—), 6.67 (1H,<br>               OH<br>s, =CH—), 6.72-7.48 (8H, m, benzene ring H × 8), 10.45 (1H, bs, >NH) |
| 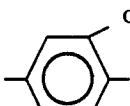<br>Oily | NMR (CDCl$_3$) δ values: 1.10-1.70 (6H, m, >CH$_2$ × 3), 1.72-2.50 (8H, m, >CH$_2$ × 4), 2.60-3.00 (4H, m, >CH$_2$ × 2), 3.05-3.80 (6H, m, >CH$_2$ × 3), 4.04 (2H, m, >CH$_2$), 4.60 (1H, m, —C$\underline{H}$—), 6.53 (1H, s, =CH—), 6.60-7.30 (7H, m,<br>        OH<br>benzene ring H × 7) |
| 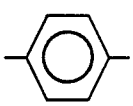<br>Oily | NMR (CDCl$_3$) δ values: 1.02-1.69 (6H, m, >CH$_2$ × 3), 1.76-2.49 (6H, m, >CH$_2$ × 3), 3.09-3.74 (6H, m, >CH$_2$ × 3), 4.1 (2H, m, >CH$_2$), 4.8 (2H, m, —OH, —C$\underline{H}$—), 5.91 (2H, s,<br>                     OH<br>—OCH$_2$O—), 6.60 (1H, s, =CH—), 6.65-7.42 (7H, m, benzene ring H × 7), 9.90-10.40 (1H, b, >NH) |
| <br>Oily | NMR (CDCl$_3$) δ values: 1.00-1.70 (9H, m, —CH$_3$, >CH$_2$ × 3), 1.79-2.81 (8H, m, >CH$_2$ × 4), 3.00-3.70 (6H, m, >CH$_2$ × 3), 4.13 (2H, m, >CH$_2$), 4.91 (2H, m, —C$\underline{H}$—, —OH), 6.68 (1H, s, =CH—),<br>         OH<br>6.70-7.52 (8H, m, benzene ring H × 8) |

TABLE 11-continued

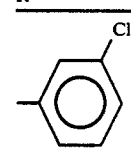

| R² | | Physical properties |
|---|---|---|
| 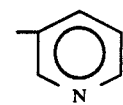 Oily | | NMR (CDCl₃) δ values: 1.10-1.70 (6H, m, —CH₂ × 3), 1.81-2.52 (6H, m, >CH₂ × 3), 3.10-3.68 (6H, m, >CH₂ × 3), 4.11 (2H, m, >CH₂), 4.92 (1H, m, —CH—), 6.66 (1H, s, $\underset{\mathrm{OH}}{\vert}$ =CH—), 6.78-7.51 (8H, m, benzene ring H × 8) |
| 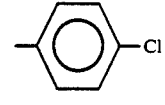 Oily | | NMR (CDCl₃) δ values: 1.11-1.71 (6H, m, >CH₂ × 3), 1.82-2.58 (6H, m, >CH₂ × 3), 3.11-3.80 (6H, m, >CH₂ × 3), 4.09 (2H, m, >CH₂), 5.01 (1H, m, —CH—), 6.69 (1H, s, =CH—), $\underset{\mathrm{OH}}{\vert}$ 6.81-7.47 (5H, m, benzene ring H × 4, pyridine ring H), 7.60-8.01 (1H, m, pyridine ring H), 8.31-8.71 (2H, m, pyridine ring H × 2), 10.29 (1H, bs, >NH) |
| 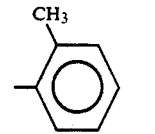 Oily | | NMR (CDCl₃) δ values: 1.05-1.75 (6H, m, >CH₂ × 3), 1.88-2.51 (6H, m, >CH₂ × 3), 3.00-3.75 (6H, m, >CH₂ × 3), 4.10 (2H, m, >CH₂), 4.91 (1H, m, —CH—), 6.69 (1H, s, =CH—), $\underset{\mathrm{OH}}{\vert}$ 6.73-7.47 (8H, m, benzene ring H × 8) |
| 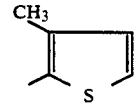 Oily | | NMR (CDCl₃) δ values: 1.15-1.70 (6H, m, >CH₂ × 3), 1.8-2.55 (6H, m, >CH₂ × 3), 2.30 (3H, s, —CH₃), 3.10-3.70 (6H, m, >CH₂ × 3), 4.15 (2H, m, >CH₂), 5.15 (1H, m, —CH—), 6.68 (1H, s, $\underset{\mathrm{OH}}{\vert}$ =CH—), 6.75-7.76 (8H, m, benzene ring H × 8) |
| 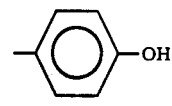 Oily | | NMR (CDCl₃) δ values: 1.10-1.80 (6H, m, >CH₂ × 3), 1.82-2.55 (6H, m, >CH₂ × 3), 2.17 (3H, s, —CH₃), 3.03-3.83 (6H, m, >CH₂ × 3), 4.15 (2H, m, >CH₂), 5.30 (1H, m, —CH—), $\underset{\mathrm{OH}}{\vert}$ 6.69 (1H, s, =CH—), 6.75-7.50 (6H, m, benzene ring H × 4, thiophene ring H × 2) |
| 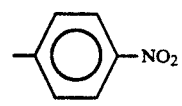 Oily | | NMR (d₆-DMSO) δ values: 1.30-1.75 (6H, m, >CH₂ × 3), 2.30-2.70 (6H, m, >CH₂ × 3), 3.09-3.78 (6H, m, >CH₂ × 3), 3.78-4.46 (3H, m, >CH₂, —OH), 4.78 (1H, m, —CH—), 5.82 (1H, bs, $\underset{\mathrm{OH}}{\vert}$ —OH), 6.68 (1H, s, =CH—), 6.75-7.46 (8H, m, benzene ring H × 8) |
| 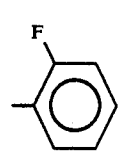 Oily | | NMR (CDCl₃) δ values: 1.10-1.80 (6H, m, >CH₂ × 3), 1.80-2.55 (6H, m, >CH₂ × 3), 3.05-3.70 (6H, m, >CH₂ × 3), 4.06 (2H, m, >CH₂), 5.05 (1H, m, —CH—), 6.60 (1H, s, =CH—), $\underset{\mathrm{OH}}{\vert}$ 6.70-8.31 (8H, m, benzene ring H × 8) |
|  Oily | | NMR (CDCl₃) δ values: 1.15-1.65 (6H, m, >CH₂ × 3), 1.78-2.58 (6H, m, >CH₂ × 3), 3.15-3.75 (6H, m, >CH₂ × 3), 4.15 (2H, m, >CH₂), 5.32 (2H, m, —OH, —CH—), 6.75 (1H, s, =CH—), $\underset{\mathrm{OH}}{\vert}$ 6.85-7.85 (8H, m, benzene ring H × 8) |

TABLE 11-continued

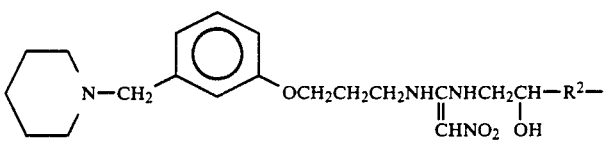

| $R^2$ | Physical properties |
|---|---|
| 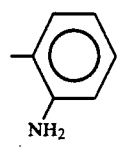<br>Oily | NMR (CDCl₃) δ values: 1.15–1.65 (6H, m, >CH₂ × 3), 1.77–2.50 (6H, m, >CH₂ × 3), 3.15–3.65 (6H, m, >CH₂ × 3), 4.01 (2H, m, >CH₂), 4.26–5.15 (4H, m, —NH₂, —C$\underline{H}$—, —OH), 6.54–7.45<br>$\quad\quad\quad\quad\quad\quad\quad\quad\quad$ OH<br>(9H, m, =CH—, benzene ring H × 8) |
| 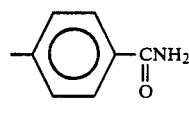<br>Amorphous | NMR (d₆-DMSO) δ values: 1.20–2.26 (8H, m, >CH₂ × 4), 2.65–3.70 (8H, m, >CH₂ × 4), 3.80–4.30 (4H, m, >CH₂ × 2), 4.40–5.10 (2H, m, —OH, —C$\underline{H}$—), 6.00 (1H, bs, >NH), 6.53 (1H, s,<br>$\quad\quad\quad\quad\quad\quad\quad$ OH<br>=CH—), 6.80–8.20 (10H, m, benzene ring H × 8, —NH₂), 10.40 (1H, bs, >NH) |
| 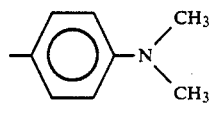<br>Amorphous | NMR (CDCl₃) δ values: 1.00–1.80 (6H, m, >CH₂ × 3), 1.80–2.60 (6H, m, >CH₂ × 3), 2.95 (6H, s, —CH₃ × 2), 3.00–3.80 (6H, m, >CH₂ × 3), 3.90–4.35 (2H, m, >CH₂), 4.50–5.20 (2H, m, —OH, —C$\underline{H}$—), 6.69 (1H, s,<br>$\quad\quad\quad\quad\quad\quad\quad\quad$ OH<br>=CH—), 6.40–7.70 (8H, m, benzene ring H × 8) |
| 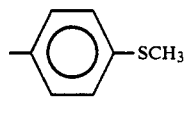<br>Oily | NMR (CDCl₃) δ values: 1.1–1.7 (6H, m, >CH₂ × 3), 1.75–2.65 (6H, m, >CH₂ × 3), 2.42 (3H, s, —SCH₃), 3.0–3.8 (6H, m, >CH₂ × 3), 4.05 (2H, m, >CH₂), 4.9 (1H, m, —C$\underline{H}$—), 6.65<br>$\quad\quad\quad\quad\quad\quad\quad\quad\quad\quad\quad$ OH<br>(1H, s, =CH—), 6.75–7.60 (8H, m, benzene ring H × 8), 10.35 (1H, bs, >NH) |
| 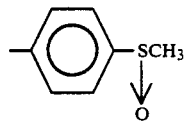<br>Amorphous | NMR (CDCl₃) δ values: 1.1–1.8 (6H, m, >CH₂ × 3), 1.85–2.6 (6H, m, >CH₂ × 3), 2.68 (3H, s, —SCH₃), 3.05–3.85 (6H, m, >CH₂ × 3), 4.1 (2H, m, >CH₂), 5.0 (1H, m, —C$\underline{H}$—),<br>$\quad\quad\quad\quad\quad\quad\quad\quad\quad\quad$ OH<br>6.65 (1H, s, =CH—), 6.75–7.80 (8H, m, benzene ring H × 8), 10.3 (1H, bs, >NH) |
| 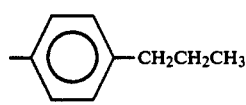 | Melting point 111–112.5° C. |
| 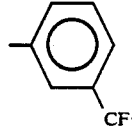<br>Oily | NMR (CDCl₃) δ values: 1.1–1.75 (6H, m, >CH₂ × 3), 1.8–2.55 (6H, m, >CH₂ × 3), 3.05–3.85 (6H, m, >CH₂ × 3), 4.12 (2H, m, >CH₂), 5.0 (1H, m, —C$\underline{H}$—), 6.70 (1H, s, =CH—),<br>$\quad\quad\quad\quad\quad\quad$ OH<br>6.75–7.85 (8H, m, benzene ring H × 8), 10.35 (1H, bs, >NH) |

TABLE 11-continued

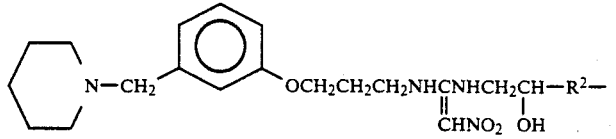

| R² | Physical properties |
|---|---|
| 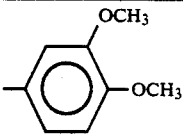<br>Amorphous | NMR (CDCl₃) δ values: 1.10–1.80 (6H, m, >CH₂ × 3), 1.80–2.55 (6H, m, >CH₂ × 3), 2.90–3.70 (6H, m, >CH₂ × 3), 3.81 (6H, s, —OCH₃ × 2), 3.95–4.30 (2H, m, >CH₂), 4.45–5.10 (2H, m, —OH, —C$\underline{H}$—), 6.58 (1H, s,<br>$\quad\quad\quad\quad\quad\quad\quad$ OH<br>=CH—), 6.40–7.50 (7H, m, benzene ring H × 7), 10.30 (1H, bs, >NH) |
| 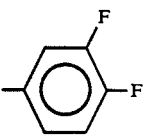<br>Oily | NMR (CDCl₃) δ values: 1.04–1.75 (6H, m, >CH₂ × 3), 1.85–2.63 (6H, m, >CH₂ × 3), 2.94–3.74 (6H, m, >CH₂ × 3), 3.88–4.34 (2H, m, >CH₂), 4.88 (1H, m, —C$\underline{H}$—), 5.90 (1H, b, —OH),<br>$\quad\quad\quad\quad\quad\quad\quad$ OH<br>6.65 (1H, s, =CH—), 6.74–7.45 (7H, m, benzene ring H × 7), 10.25 (1H, bs, >NH) |

EXAMPLE 11

In 10 ml of methylene chloride was dissolved 0.68 g of N,N'-carbonyldiimidazole, and 5 ml of a methylene chloride solution containing 1.0 g of 3-(3-piperidinomethylphenoxy)propylamine was added dropwise at 0° C. to 5° C., after which the resulting mixture was subjected to reaction at the same temperature for 1 hour and then at room temperature for 1 hour. Subsequently, 0.6 g of DL-β-hydroxyphenethylamine was added at 0° C., and the mixture thus obtained was subjected to reaction with ice-cooling for 1 hour and then at room temperature for 1 hour. After completion of the reaction, 10 ml of water was added, and the organic layer was separated. The organic layer was dried over anhydrous magnesium sulfate, after which the solvent was removed by distillation under reduced pressure, and the resulting residue was purified by a column chromatography (Wako Silica Gel C-200, eluent; chloroform: ethanol=20:1 by volume) to obtain 0.75 g (yield 45.6%) of oily N-(β-hydroxyphenethyl)-N'-[3-(3-piperidinomethylphenoxy)propyl]urea.

NMR (CDCl₃) δ values: 1.28–1.68 (6H, m, >CH₂×3), 1.69–2.54 (6H, m, >CH₂×3), 2.96–3.54 (6H, m, >CH₂×3), 3.97 (2H, m, >CH₂), 4.74

(1H, m, —C$\underline{H}$—),
$\quad\quad\quad$ OH 4.20–5.30 (1H, b, —OH), 6.00 (2H, bs, >NH×2), 6.63–7.68 (9H, m, benzene ring H×9)

EXAMPLE 12

(1) In 900 ml of methanol were dissolved 30 g of 2-[(2-guanidino-4-thiazolyl)methylthio]ethylamine dihydrochloride and 27.4 ml of triethylamine, and 15.1 g of dimethylcyanoimide dithiocarbonate was added at room temperature, and the resulting mixture was subjected to reaction overnight at the same temperature. After completion of the reaction, the solvent was removed by distillation under reduced pressure, and 400 ml of ethyl acetate and 300 ml of water were added to the resulting residue, after which the white crystals deposited were collected by filtration and dried to obtain 27 g (yield 83%) of N-cyano-N'-}2-[(2-guanidino-4-thiazolyl)methylthio]ethyl}-S-methylisothiourea having a melting point of 127°–134° C.

IR (KBr) cm⁻¹: $\nu_{C\equiv N}$2160

NMR (d₆DMSO) δ values: 2.50–3.00 (5H, m, —CH₃, >CH₂), 3.10–4.10 (4H, m, >CH₂×2), 6.86 (1H, s, thiazole ring H), 7.70 (4H, bs, —NH₂×2)

(2) With 5 ml of ethanol were mixed 1.5 g of the N-cyano-N'}2-[(2-guanidino-4-thiazolyl)methylthio]ethyl}-S-methylisothiourea obtained in above (1) and 3.1 g of DL-β-hydroxyphenethylamine, and the resulting mixture was subjected to reaction under reflux for 4 hours. After completion of the reaction, the solvent was removed by distillation under reduced pressure, and the resulting residue was washed with two 20-ml portions of diethyl ether. The residue was then dissolved in 5 ml of acetone, and a solution of 1.5 g of maleic acid in 8 ml of acetone was added at room temperature. Subsequently, 10 ml of diethyl ether was added dropwise, after which the crystals deposited were collected by filtration and recrystallized from isopropanol to obtain 1.73 g (yield 71%) of maleic acid salt (1:1 adduct) of N-cyano-N'-{2-[(2-guanidino-4-thiazolyl)methylthio]ethyl}-N''-(β-hydroxyphenethyl)guanidine having a melting point of 100°–103° C.

IR (KBr) cm⁻¹: $\nu_{C\equiv N}$2160

The following compound was obtained in the same manner as described above.

Maleic acid salt (1:1 adduct) of N-cyano-N'-{2-[(2-guanidino-4-thiazolyl)methylthio]ethyl}-N''-(2-methoxy-2-phenylethyl)guanidine Melting point: 136°–138° C.

IR (KBr) cm⁻¹: $\nu_{C\equiv N}$2170

EXAMPLE 13

With 5 ml of ethanol were mixed 1.0 g of N-cyano-N'-{2-[(2-guanidino-4-thiazolyl)methylthio]ethyl}-S-methylisothiourea, 1.38 g of DL-(2-hydroxy-1-methyl-2-phenylethyl)amine and 0.57 g of silver nitrate, and the resulting mixture was subjected to reaction under reflux for 2 hours and 20 minutes. After completion of the reaction, the insolubles were removed by filtration, and the solvent was removed by distillation under reduced pressure. The resulting residue was purified by a column chromatography (Florisil, eluent; chloroform:ethanol =9:1 by volume). The amorphous solid thus obtained was dissolved in 4 ml of acetone, and a solution of 1 g of maleic acid in 8 ml of acetone was added at room temperature. Subsequently, 10 ml of diethyl ether was added dropwise, after which the crystals deposited were collected by filtration and recrystallized from isopropanol to obtain 1.0 g (yield 59%) of maleic acid salt (1:1 adduct) of N-cyano-N'-{2-[(2-guanidino-4-thiazolyl)methylthio]ethyl}-N''-(2-hydroxy-1-methyl-2-phenylethyl)guanidine having a melting point of 125.5°-127° C.

IR (KBr) cm$^{-1}$: $\nu_{C\equiv N}$2160

EXAMPLE 14

With 15 ml of ethanol were mixed 3.0 g of N-cyano-N'-{2-[(2-guanidino-4-thiazolyl)methylthio]ethyl}-S-methylisothiourea, 4.9 g of DL-[2-hydroxy-2-(3-hydroxyphenyl)ethyl]amine and 1.97 g of silver nitrate, and the resulting mixture was subjected to reaction under reflux for 1.5 hours. After completion of the reaction, the insolubles were removed by filtration, and the solvent was removed by distillation under reduced pressure. The resulting residue was purified by a column chromatography (Wako Silica Gel C-200, eluent; chloroform:methanol=5:1 by volume) and crystallized from methanol to obtain 2.5 g (yield 68%) of N-cyano-N'-{2-[(2-guanidino-4-thiazolyl)methylthio]ethyl}-N''-[2-hydroxy-2-(3-hydroxyphenyl)ethyl]guanidine having a melting point of 162°-164° C.

IR (KBr) cm$^{-1}$: $\nu_{C\equiv N}$2160

The following compound was obtained in the same manner as described above.

N-cyano-N'-{2-[(2-guanidino-4-thiazolyl)methylthio]ethyl}-N''-[2-hydroxy-2-(4-nitrophenyl)ethyl]guanidine(amorphous)

IR (KBr) cm$^{-1}$: $\nu_{C\equiv N}$2160

NMR (d$_6$DMSO) δ values: 2.35-2.90 (2H, m, >CH$_2$), 2.95-3.60 (4H, m, >CH$_2$×2), 3.79 (2H, s, >CH$_2$), 4.91

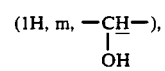

6.54-7.37 (2H, m, >NH×2), 7.07 (1H, s, thiazole ring H), 7.61, 8.17 (4H, AA', BB', benzene ring H×4), 8.29 (4H, bs, —NH$_2$×2)

EXAMPLE 15

(1) In 300 ml of methanol was suspended 20 g of 2-[(2-guanidino-4-thiazolyl)methylthio]ethylamine dihydrochloride, and 7.1 g (99.7% purity) of sodium methoxide was added, after which the crystals deposited were removed by filtration and the solvent was removed by distillation under reduced pressure. With the resulting residue were mixed 150 ml of ethanol, 80 ml of acetonitrile and 23.9 g of 1,1-bis(methylthio)-2-nitroethene, and the resulting mixture was subjected to reaction under reflux for 5 hours. After completion of the reaction, the reaction mixture was cooled with ice, and the crystals deposited were collected by filtration and extracted with 500 ml of methanol with heating. The extract was concentrated to dryness under reduced pressure, and the crystals thus obtained were washed with 100 ml of acetonitrile to obtain 14.8 g (yield 65%) of 1-{2-[(2-guanidino-4-thiazolyl)methylthio]ethylamino}-1-methylthio-2-nirroethene having a melting point of 154°-156° C. (decomp.).

NMR (d$_6$DMSO) δ values: 2.67 (3H, s, —CH$_3$), 2.20-3.15 (2H, m, >CH$_2$), 3.15-4.15 (4H, m, >CH$_2$×2), 6.77 (1H, s, =CH—), 6.87 (1H, s, thiazole ring H), 7.67 (4H, bs, —NH$_2$×2)

(2) With 60 ml of ethanol were mixed 2.0 g of the 1-{2-[(2-guanidino-4-thiazolyl)methylthio]ethylamino}-1-methylthio-2-nitroethene obtained in above (1) and 3.9 g of DL-β-hydroxyphenethylamine, and the resulting mixture was subjected to reaction under reflux for 2 hours. After completion of the reaction, the solvent was removed by distillation under reduced pressure, and the oily substance thus obtained was washed with two 40-ml portions of diethyl ether and then purified by a column chromatography (Wako Silica Gel C-200, eluent; chloroform:methanol=9:1 by volume) to obtain 1.0 g (yield 40%) of amorphous N-{2-[(2-guanidino-4-thiazolyl)methylthio]ethyl}-N'-(β-hydroxyphenethyl)-2-nitro-1,1-ethenediamine.

NMR (d$_6$DMSO) δ values: 2.50-3.00 (2H, m, >CH$_2$), 3.20-3.65 (4H, m, >CH$_2$×2), 3.75 (2H, s, >CH$_2$), 4.91

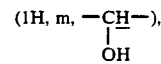

6.69 (1H, s, thiazole ring H), 6.75 (1H, s, =CH—), 7.03 (4H, bs, —NH$_2$×2), 7.65 (5H, s, benzene ring H×5), 7.3-7.8 (2H, m, >NH×2)

The following compounds were obtained in the same manner as described above.

N-[2-(4-chlorophenyl)-2-hydroxyethyl]-N'-{2-[(2-guanidino-4-thiazolyl)methylthio]ethyl}-2-nitro-1,1-ethenediamine Melting point: 146°-150° C. (decomp.)

N-[2-(2-furyl)-2-hydroxyethyl]-N'-{2-[(2-guanidino-4-thiazolyl)methylthio]ethyl}-2-nitro-1,1-ethenediamine Melting point: 171°-173° C. (decomp )

N-{2-[(2-guanidino-4-thiazolyl)methyltio]ethyl}-N'-[2-hydroxy-2-(2-thienyl)ethyl]-2-nitro-1,1-ethenediamine Melting point: 181°-183° C. (decomp.)

N-{2-[(2-guanidino-4-thiazolyl)methylthio]ethyl}-N'-[2-hydroxy-2-(4-hydroxyphenyl)ethyl]-2-nitro-1,1-ethenediamine (amorphous)

NMR (d$_6$DMSO) δ values: 2.50-3.00 (2H, m, >CH$_2$), 3.15-3.95 (4H, m, >CH$_2$×2), 3.75 (2H, bs, >CH$_2$), 4.76

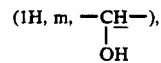

6.66 (1H, s, =CH—), 6.75 (1H, s, thiazole ring H), 6.86, 7.32 (4H, AA', BB', benzene ring H×4), 6.60-7.90 (4H, bs, —NH$_2$×2)

EXAMPLE 16

With 5 ml of ethanol were mixed 1 g of N-cyano-N'-{2-[(5-methyl-4-imidazolyl)methylthio]ethyl}-S-methylisothiourea and 2.6 g of DL-β-hydroxyphenethylamine, and the resulting mixture was subjected to reaction under reflux for 5 hours. After completion of the reaction, the solvent was removed by distillation under reduced pressure, and the oily substance thus obtained was washed with 20 ml of diethyl ether and then purified by a column chromatography (Wako Silica Gel C-200, eluent; chloroform methanol=10:1 by volume) to obtain 0.27 g (yield 20%) of amorphous N-cyano-N'-(β-hydroxyphenethyl)-N''-{2-[(5-methyl-4-imidazolyl)methylthio]ethyl}guanidine.

NMR (d$_6$DMSO) δ values: 2.16 (3H, s, —CH$_3$), 2.40–2.90 (2H, m, >CH$_2$), 3.05–3.95 (4H, m, >CH$_2$×2), 3.67 (2H, bs, >CH$_2$), 4.83

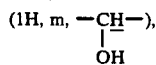

6.79 (3H, bs, >NH×3), 7.38 (5H, bs, benzene ring H×5), 7.52 (1H, s, imidazole ring H)

EXAMPLE 17

In 15 ml of pyridine was dissolved 1.0 g of N-{2-[[5-(dimethylamino)methyl-2-furyl]methylthio]ethyl}-N'-[2-hydroxy-2-(4-hydroxyphenyl)ethyl]-2-nitro-1,1-ethynediamine, and 0.86 ml of acetic anhydride was added with ice-cooling, after which the resulting mixture was subjected to reaction at room temperature for 4 hours. After completion of the reaction, the solvent was removed by distillation under reduced pressure, and 20 ml of chloroform and 10 ml of water were added to the residue to dissolve the same. The aqueous layer was adjusted to pH 10 with a 1 N aqueous sodium hydroxide solution, after which the chloroform layer was separated and then washed with water. After the chloroform layer was dried over anhydrous magnesium sulfate, the solvent was removed by distillation under reduced pressure, and the resulting residue was purified by a column chromatography (Wako Silica Gel C-200, eluent; chloroform:methanol=20:1 by volume to obtain 0.65 g (yield 54.6%) of amorphous N-[2-acetoxy-2-(4-acetoxyphenyl)ethyl]-N'-{2-[[5-(dimethylamino)methyl-2-furyl]methylthio]ethyl}-2-nitro-1,1-ethenediamine.

NMR (CDCl$_3$) δ values: 2.08 (3H, s, —CH$_3$), 2.26 (9H, s, —CH$_3$×3), 2.47–2.92 (2H, m, >CH$_2$), 3.10–3.87 (4H, m, >CH$_2$×2), 3.55 (2H, s, >CH$_2$), 3.73 (2H, s, >CH$_2$), 5.98

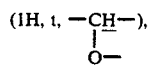

6.20 (2H, s, furan ring H×2), 6.66 (1H, s, =CH—), 7.10, 7.47 (4H, AA', BB', benzene ring H×4), 8.87 (1H, bs, >NH)

EXAMPLE 18

In 2 ml of ethanol was dissolved 0.18 g of N-{2-[[5-(dimethylamino)methyl-4-methyl-2-thienyl]methylthio]ethyl}-N'-[2-hydroxy-2-(3-methoxyphenyl)ethyl]-2-nitro-1,1-ethenediamine, and a solution of 0.052 g of oxalic acid dihydrate in 1 ml of ethanol was added thereto. After deposition of an oxalic acid salt, 2 ml of diethyl ether was added, and the oxalic acid salt was collected by filtration to obtain 0.18 g of the oxalic acid salt of N-{2-[[5-(dimethylamino)methyl-4-methyl-2-thienyl]methylthio]ethyl}-N'-[2-hydroxy-2-(3-methoxyphenyl)ethyl]-2-nitro-1,1-ethenediamine having a melting point of 114°–116° C. (decomp.).

EXAMPLE 19

With 15 ml of ethanol was mixed 0.8 g of N-[2-hydroxy-2-(4-nitrophenyl)ethyl]-2-nitro-N'-[3-(3-piperidinomethylphenoxy)propyl]-1,1-ethenediamine, and hydrogen gas was introduced thereinto in the presence of 0.1 g of 5% (by weight) palladium carbon at ordinary temperature and under atmospheric pressure for 7 hours until the absorption of hydrogen gas ceased. Subsequently, the catalyst was removed by filtration and the solvent was removed by distillation under reduced pressure. The resulting residue was purified by a column chromatography (Wako Silica Gel C-200, eluent; chloroform:methanol=5:1 by volume) to obtain 0.3 g (yield 40%) of amorphous N-[2-(4-aminophenyl)-2-hydroxyethyl]-2-nitro-N'-[3-(3-piperidinomethylphenoxy)propyl] -1,1-ethenediamine.

NMR (CDCl$_3$) δ values: 1.10–1.70 (6H, m, >CH$_2$×3), 1.80–2.60 (6H, m, >CH$_2$×3), 3.10–3.60 (6H, m, >CH$_2$×3), 4.00 (2H, m, >CH$_2$), 4.20–5.00

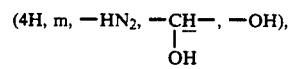

6.40-7.40 (9H, m, =CH—, benzene ring H×8)

EXAMPLE 20

The compounds listed in Tables 12 and 13 were obtained by effecting reaction by use of the corresponding starting materials in the same manner as in Examples 1, 2 and 9. (Unless otherwise specified, as the compounds of the formula (V), their DL-forms were used.)

TABLE 12

R$^1$CH$_2$SCH$_2$CH$_2$NHCNHY—CH—R$^2$
       ‖      |
       Z     OH

| R$^1$ | Z | Y | R$^2$ | Physical properties |
|---|---|---|---|---|
| 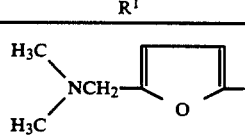 | =NSO$_2$CH$_3$ | —CH$_2$— | 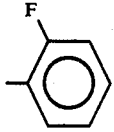 | Amorphous NMR(CDCl$_3$) δ values: 2.08(6H, s, —CH$_3$×2), 2.50–2.89(2H, m, >CH$_2$), 2.81(3H, s, —CH$_3$), 3.08–4.70(4H, m, >CH$_2$×2), 3.34(2H, s, >CH$_2$), 3.72 (2H, s, >CH$_2$), 5.13(2H, m, —CH—, OH), 6.10(2H, s, OH furan ring H×2), 6.66–7.76(6H, m, >NH×2, |

TABLE 12-continued $$R^1CH_2SCH_2CH_2NHCNHY-CH-R^2$$
$$\underset{Z}{\|} \quad \underset{OH}{|}$$

| R¹ | Z | Y | R² | Physical properties |
|---|---|---|---|---|
| H₃C\NCH₂-[furan]- / H₃C | =NSO₂CH₃ | —CH₂— | -[benzene]-OH | Oily<br>NMR(CDCl₃) δ values:<br>2.14(6H, s, —CH₃×2),<br>2.38–3.03(5H, m, >CH₂,<br>—CH₃), 3.08–3.73(4H, m,<br>>CH₂×2), 3.38(2H, s,<br>>CH₂), 3.64(2H, s, >CH₂),<br>4.74(1H, m, —C$\underline{H}$—), 5.95–6.46<br>$\quad\quad\quad\quad\quad\quad\quad$ OH<br>(3H, m, >NH, furan ring<br>H×2), 6.59–7.33(5H, m,<br>>NH, benzene ring H×4) |
| H₃C\NCH₂-[furan]- / H₃C | =NSO₂N(CH₃)(CH₃) | —CH₂— | -[benzene]-OH | Amorphous<br>NMR(d₆-DMSO) δ values:<br>2.10(6H, s, —CH₃×2),<br>2.35–2.9(2H, m, >CH₂),<br>2.62(6H, s, —CH₃×2),<br>3.0–3.8(4H, m, >CH₃×2),<br>3.47(2H, s, >CH₂), 3.62<br>(2H, s, >CH₂), 4.7(1H, m,<br>—C$\underline{H}$—), 6.11(2H, s, furan<br>$\quad$ OH<br>ring H×2), 6.35(2H, bs,<br>>NH×2), 6.72, 7.14(4H,<br>AA′, BB′, benzene ring H×4) |
| H₃C\NCH₂-[furan]- / H₃C | =NCN | —CH₂— | -[benzene]-OH | Amorphous<br>IR(KBr)cm⁻¹: $\nu_{C\equiv N}$ 2160,<br>$\quad\quad\quad\quad\quad \nu_{C=N}$ 1580<br>NMR(d₆-DMSO+D₂O) δ values:<br>2.13(6H, s, —CH₃×2),<br>2.4–2.75(2H, m, >CH₂),<br>3.05–3.5(4H, m, >CH₂×2),<br>3.40(2H, s, >CH₂),<br>3.78(2H, s, >CH₂),<br>4.65(1H, t, —C$\underline{H}$—), 6.22<br>$\quad\quad\quad\quad\quad$ OD<br>(2H, s, furan ring H×2),<br>6.76, 7.22(4H, AA′, BB′,<br>benzene ring H×4) |
| H₃C\NCH₂-[furan]- / H₃C | =CHNO₂ | —CH(CH₃)— | -[benzene] | Amorphous<br>NMR(CDCl₃) δ values:<br>1.12(3H, d, —CH₃),<br>1.99(6H, s, —CH₃×2),<br>2.57–2.98(2H, m, >CH₂),<br>3.10–3.62(3H, m, >CH₂),<br>\—CH), 3.32(2H, s, >CH₂),<br>/<br>3.76(2H, s, >CH₂), 4.76<br>(1H, m, —C$\underline{H}$—), 6.11(2H, s,<br>$\quad\quad\quad\quad$ OH<br>furan ring H×2), 6.55<br>(1H, s, =CH—), 7.23(5H,<br>s, benzene ring H×5),<br>7.86–8.47(1H, b, >NH),<br>9.37–9.86(1H, b, >NH) |
| H₃C\NCH₂-[3-methylfuran]- / H₃C | =CHNO₂ | —CH₂— | -[benzene]-OH | Amorphous<br>NMR(d₆-DMSO) δ values:<br>2.02(3H, s, —CH₃), 2.21<br>(6H, s, —CH₃×2), 2.50–2.95<br>(2H, m, >CH₂), 2.95–3.70<br>(6H, m, >CH₂×3),<br>3.86(2H, s, >CH₂), 4.83 |

TABLE 12-continued $$R^1CH_2SCH_2CH_2NHC(Z)NHY-CH(OH)-R^2$$

| R¹ | Z | Y | R² | Physical properties |
|---|---|---|---|---|
| | | | | (1H, m, —CH(OH)—), 6.32(1H, s, furan ring H), 6.72(1H, s, =CH—), 6.93, 7.41(4H, AA', BB', benzene ring H×4) |
| (H3C)2NCH2-thiophene-2,5-diyl | =CHNO2 | —CH2— | 3-OCH3-phenyl | Oily NMR(CDCl3) δ values: 2.11(6H, s, —CH3×2), 2.72(2H, t, >CH2), 3.0–3.6 (4H, m, >CH2×2), 3.51 (2H, s, >CH2), 3.80(3H, s, —CH3), 3.91(2H, s, >CH2), 4.90(1H, m, —CH(OH)—), 6.56 (1H, s, =CH—), 6.50–7.35 (8H, m, >NH×2, benzene ring H×4, thiophene ring H×2) |
| (H3C)2NCH2-thiophene-2,5-diyl | =CHNO2 | —CH2— | 2-F-phenyl | Oily NMR(CDCl3) δ values: 2.09(6H, s, —CH3×2), 2.66(2H, t, >CH2), 2.95–3.65 (4H, m, >CH2×2), 3.46(2H, s, >CH2), 3.83 (2H, s, >CH2), 5.17(1H, s, —CH(OH)—), 6.51(1H, s, =CH—), 6.30–7.80(6H, m, benzene ring H×4, thiophene ring H×2) |
| (H3C)2NCH2-thiophene-2,5-diyl | =CHNO2 | —CH2— | 4-F-phenyl | Melting point: 115–118° C. |
| (H3C)2NCH2-furan-2,5-diyl | =CHNO2 | —CH2 | 4-OH-phenyl | *1 Melting point: 128–130° C. [α]$_D^{24}$ = −26.9° (C 0.962, 0.1 N—HCl) |
| (H3C)2NCH2-furan-2,5-diyl | =CHNO2 | —CH2 | 4-OH-phenyl | *2 Melting point: 128–130° C. [α]$_D^{23}$ = +26.8° (C 0.99, 0.1 N—HCl) |
| (H3C)2NCH2-(3-CH3-thiophene)-2,5-diyl | =CHNO2 | —CH2 | 3-OH-phenyl | *3 Amorphous [α]$_D^{20}$ = +12.7° (C 0.52, CH3OH) |
| (H3C)2NCH2-(3-CH3-thiophene)-2,5-diyl | =CHNO2 | —CH2 | 3-OH-phenyl | *4 Amorphous [α]$_D^{24}$ = −11.7° (C 0.562, CH3OH) |
| (H3C)2NCH2-(3-CH3-thiophene)-2,5-diyl | =CHNO2 | —CH2 | 3-OCH3-phenyl | *5 Oily [α]$_D^{20}$ = +17.4° (C 0.472, CH3OH) |

TABLE 12-continued $$R^1CH_2SCH_2CH_2NHCNHY-CH-R^2$$
$$\phantom{R^1CH_2SCH_2CH_2NHC}\underset{Z}{\|}\phantom{NHY-}\underset{OH}{|}$$

| R¹ | Z | Y | R² | Physical properties |
|---|---|---|---|---|
| (3-dimethylaminomethyl-thiophene with CH₃) | =CHNO₂ | —CH₂ | (phenyl with OCH₃) | *6 Oily $[\alpha]_D^{24} = -17.7°$ (C 0.514, CH₃OH) |

1) *1: R(—) configuration obtained by using R(—)-[2-hydroxy-2-(4-hydroxyphenyl)-ethyl]amine {$[\alpha]_D^{25} = -49.1°$ (C 1.00, 0.1 N—HCl): 88% optical purity}
2) *2: S(+) configuration obtained by using S(+)-[2-hydroxy-2-(4-hydroxyphenyl)-ethyl]amine {$[\alpha]_D^{23} = +51.5°$ (C 1.01, 0.1 N—HCl): 98% optical purity}
3) *3: R(+) configuration obtained by using hydrochloride salt of R(+)-[2-hydroxy-2-(3-hydroxyphenyl)ethyl]amine {$[\alpha]_D^{22} = +53.4°$ (C 0.494, CH₃ON)}
4) *4: S(—) configuration obtained by using hydrochloride salt of S(—)-[2-hydroxy-2-(3-hydroxyphenyl)ethyl]amine {$[\alpha]_D^{19} = -47.3°$ (C 0.48, CH₃OH)}
5) *5: R(+) configuration obtained by using hydrochloride salt of R(+)-[2-hydroxy-2-(3-methoxyphenyl)ethyl]amine {$[\alpha]_D^{21} = +52.6°$ (C 0.866, CH₃OH)}
6) *6: S(—) configuration obtained by using hydrochloride salt of S(—)-[2-hydroxy-2-(3-methoxyphenyl)ethyl]amine {$[\alpha]_D^{19} = -47.3°$ (C 0.87, CH₃OH)}

TABLE 13

$$R^1OCH_2CH_2CH_2NHCNHCH_2-CH-R^2$$
$$\phantom{R^1OCH_2CH_2CH_2NHC}\underset{Z}{\|}\phantom{NHCH_2-}\underset{OH}{|}$$

| R¹ | Z | R² | Physical properties |
|---|---|---|---|
| (3-piperidinomethyl-phenyl) | =NSO₂CH₃ | (phenyl) | Amorphous NMR(CDCl₃) δ values: 1.11–1.68(6H, m, >CH₂×3), 1.81–2.41(6H, m, >CH₂×3), 2.73(3H, s, —CH₃), 3.06–3.57 (6H, m, >CH₂×3), 4.00(2H, m, >CH₂), 4.35–4.93(2H, m, —C$\underline{H}$—, —OH), 6.31–7.40(6H, m, $\underset{OH}{|}$ >NH×2, benzene ring H×4), 7.20(5H, s, benzene ring H×5) |
| (3-piperidinomethyl-phenyl) | =NSO₂CH₃ | (4-fluorophenyl) | Oily NMR(CDCl₃) δ values: 1.10–1.65(6H, m, >CH₂×3), 1.75–2.50(6H, m, >CH₂×3), 2.80(3H, s, —CH₃), 3.09–3.64 (6H, m, >CH₂×3), 4.04 (2H, m, >CH₂), 4.74(2H, m, —C$\underline{H}$), —OH), $\underset{OH}{|}$ 6.41–7.60(10H, m, >NH×2, benzene ring H×8) |
| (3-piperidinomethyl-phenyl) | =NSO₂—(4-methylphenyl)—CH₃ | (4-hydroxyphenyl) | Melting point: 143–144° C. NMR(d₆-DMSO) δ values: 1.25–1.65(6H, m, >CH₂×3), 1.68–2.60(6H, m, >CH₂×3), 2.33(3H, s, —CH₃), 3.03–3.62 (6H, m, >CH₂×3), 3.87(2H, m, >CH₂), 4.60(1H, m, —C$\underline{H}$—), $\underset{OH}{|}$ 5.63(1H, bs, —OH), 6.50–7.82 (14H, m, >NH×2, benzene ring H×12), 8.77–9.85 (1H, b, —OH) |
| (3-piperidinomethyl-phenyl) | =NCN | (4-fluorophenyl) | Oily IR(film)cm⁻¹: $\nu_{C=N}$ 2160, $\nu_{C=N}$ 1590 NMR(CDCl₃) δ values: 1.1–1.7(6H, m, >CH₂×3), 1.75–2.5(6H, m, >CH₂×3), 3.1–3.6(4H, m, >CH₂×2), 3.38(2H, s, >CH₂), 4.05(2H, m, >CH₂), 4.6–5.1(2H, m, —OH, —C$\underline{H}$—), 6.2(1H, bs, >NH), $\underset{OH}{|}$ 6.6–7.5(8H, m, benzene ring H×8) |

TABLE 13-continued $$R^1OCH_2CH_2CH_2NHCNHCH_2-CH-R^2$$
$$\quad\quad\quad\quad\quad\quad\quad\quad \|\quad\quad\quad |$$
$$\quad\quad\quad\quad\quad\quad\quad\quad Z\quad\quad OH$$

| R¹ | Z | R² | Physical properties |
|---|---|---|---|
| 3-(3-hydroxypiperidin-1-ylmethyl)phenyl | =CHNO₂ | 2-methyl-thiophen-3-yl (CH₃, S) | Oily<br>NMR(d₆-DMSO) δ values:<br>0.65–3.00(11H, m, >CH₂×5,<br>>CH), 2.18(3H, s, —CH₃),<br>3.05–3.75(6H, m, >CH₂×3),<br>4.02(2H, m, >CH₂), 5.07(1H,<br>m, —CH—), 6.67(1H, s, =CH—),<br>   \|<br>   OH<br>6.65–7.44(6H, m, benzene ring<br>H×4, thiophene ring H×2),<br>9.90–10.70(1H, b, >NH) |
| 3-(3-hydroxypiperidin-1-ylmethyl)phenyl | =CHNO₂ | phenyl | Oily<br>NMR(CDCl₃) δ values:<br>0.99–2.97(11H, m, >CH₂×5,<br>>CH), 3.10–3.80(6H, m,<br>>CH₂×3), 4.06(2H, m, >CH₂),<br>4.92(1H, m, —CH—), 6.67(1H,<br>   \|<br>   OH<br>S, =CH—), 6.77–7.57(9H, m,<br>benzene ring H×9) |
| 3-(piperidin-1-ylmethyl)phenyl | =CHNO₂ | phenyl | *<br>Oily<br>[α]$_D^{23}$ = +11.1° (C 1.00, chloroform) |
| 3-(piperidin-1-ylmethyl)phenyl | =CHNO₂ | phenyl | **<br>Oily<br>[α]$_D^{23}$ = −10.7° (C 0.92, chloroform) |

1) *: R(+) configuration obtained by using R(−)-β-hydroxyphenethylamine {[α]$_D^{23}$ = −43.7°(C 2, ethanol) 97.5% optical purity}.
2) **: S(−) configuration obtained by using S(+)-β-hydroxyphenethylamine {[α]$_D^{23}$ = +43.0°(C 2, ethanol) 96% optical purity}.

EXAMPLE 21

With 2 ml of ethanol was mixed 1 g of 2-{[2-(dimethylamino)methyl-4-thiazolyl]methylthio}ethylamine and 1.1 g of 2-nitromethylene-5-phenyl-oxazolidine, and the resulting mixture was subjected to reaction under reflux for 1 hour. After completion of the reaction, the reaction mixture was filtered with cooling, and the solvent was removed by distillation under reduced pressure, after which the resulting residue was purified by a column chromatography (Wako Silica Gel C-200, eluent: chloroform:ethanol=20:1 by volume) to obtain 1.3 g (yield 68%) of N-{2-[[2-(dimethylamino)methyl-4-thiazolyl]methylthio]ethyl}-(dimethylamino)methyl-4-thiazolyl]methylthio]ethyl}-N'-(3-hydroxyphenethyl)-2-nitro-1,1-ethenediamine having a melting point of 100°–101° C.

NMR (CDCl₃) δ values: 2.20 (6H, s, —CH₃×2), 2.47–3.02 (2H, m, >CH₂), 3.08–3.72 (4H, m, >CH₂×2), 3.60 (2H, s, >CH₂), 3.88 (2H, s, >CH₂), 4.87

(1H, m, —CH—),
       |
       OH 6.63 h(1H, s, =CH—), 7.18 (1H, s, thiazole ring H), 7.39 (5H, s, benzene ring H×5), 10.39 (1H, bs, >NH)

EXAMPLE 22

(1) With 2 ml of acetonitrile were mixed 1 g of 2-{[2-(dimethylamino)methyl-4-thiazolyl]methylthio}ethylamine and 1.4 g of 1,1-bis(methylthio)-2-nitroethene, and the resulting mixture was subjected to reaction under reflux for 2 hours. After completion of the reaction, the solvent was removed by distillation under reduced pressure, and 5 ml of ethanol was added to the resulting residue, after which the insolubles were removed by filtration. The solvent was removed by distillation under reduced pressure, and the residue thus obtained was purified by a column chromatography (Wako Silica Gel C-200, eluent; chloroform:ethanol=20:1 by volume) to obtain 0.8 g (yield 53%) of oily 1-{2-[[2-(dimethylamino)methyl-4-thiazolyl]methylthio]ethylamino}-1-methylthio-2-nitroethene.

NMR (CDCl₃) δ values: 2.36 (6H, s, —CH₃×2), 2.49 (3H, s, —CH₃), 2.63–3.03 (2H, m, >CH₂), 3.45–3.84 (2H, m, >CH₂), 3.81 (2H, s, >CH₂), 3.92 (2H, s, >CH₂), 6.67 (1H, s, =CH—), 7.25 (1H, s, thiazole ring H), 10.67 (1H, bs, >NH)

(2) In the same manner as in Example 2, 0.8 g of 1-{2-[[2-(dimethylamino)methyl-4-thiazolyl]methylthio]ethylamino}-1-methylthio-2-nitroethene obtained in above (1) and 0.4 g of DL-β-hydroxyphenethylamine were reacted and treated to obtain 0.7 g (yield 70%) of N-{2-[[2-dimethylamino)methyl-4-thiazolyl]methylthio]ethyl}-N'-(β-hydroxyphenethyl-2-nitro-1,1-ethenediamine having a melting point of 100°-101° C.

EXAMPLE 23

(1) In the same manner as in Example 6-(2), 3.8 g of 1-{[2-(tert.-butyl)dimethylsilyloxy-2-(3-methylphenyl)ethyl]amino}-1-methylthio-2-nitroethene and 2.6 g of 2-{[5-(dimethylamino)methyl-4-methyl-2-thienyl]methylthio}ethylamine were reacted and treated to obtain 4.6 g (yield 87%) of oily N-[2-(tert.-butyl)dimethylsilyloxy-2-(3-methylphenyl)ethyl]-N'-{2-[[5-(dimethylamino)methyl-4-methyl-2-thienyl]methylthio]ethyl}-2-nitro-1,1-ethenediamine.

The physical property (NMR) of this compound was identical with that in Example 7-(3).

(2) In the same manner as in Example 7-(4), 4.5 g of N-[2-(tert.-butyl)dimethylsilyloxy-2-(3-methylphenyl)ethyl]-N'-{2-[[5-(dimethylamino)methyl-4-methyl-2-thienyl]methylthio]ethyl}-2-nitro-1,1-ethenediamine was reacted and treated to obtain 3.1 g (yield 79%) of N-{2-[[5-(dimethylamino)methyl-4-methyl-2-thienyl]merhylthio]ethyl}-N'-[2-hydroxy-2-(3-methylphenyl)ethyl]-2-nitro-1,1-ethenediamine having a melting point of 88°-89° C.

EXAMPLE 24

In the same manner as in Example 3 or 6, the corresponding starting materials were subjected to reaction, to obtain the objective compounds shown in Tables 14, 15 and 16.

TABLE 14

$$\begin{array}{c}H_3C\\ \phantom{H_3C}\diagdown\\ \phantom{H_3C}NCH_2-\!\!\left\langle\!\!\begin{array}{c}\phantom{O}\\O\end{array}\!\!\right\rangle\!-CH_2SCH_2CH_2NHCNHCH_2CHR^2\\ H_3C\phantom{\diagup}\phantom{aaaaaaaaaaaaaaaaaaaa}\|\phantom{aaaa}|\\ \phantom{aaaaaaaaaaaaaaaaaaaaaaaa}CHNO_2\ \ OH\end{array}$$

| R² | R² | R² |
|---|---|---|
| phenyl | 4-chlorophenyl | 2-methyl-4-fluorophenyl |
| 4-hydroxyphenyl | 2-chlorophenyl | 2-thienyl |
| 2-hydroxyphenyl | 4-methylphenyl | 2-methyl-thien-5-yl |
| 4-methoxyphenyl | 2-methylphenyl | 2-thienyl |
| 2-methoxyphenyl | 4-ethylphenyl | 2-furyl |
| 2-methylphenyl | 3,4-methylenedioxyphenyl | 3-pyridyl |
| 4-fluorophenyl | 2,4-difluorophenyl | 2-pyridyl |

TABLE 14-continued
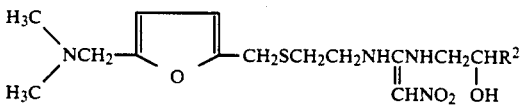
The physical properties of these compounds were identical with those in Example 1.
TABLE 15
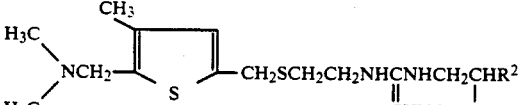

TABLE 15-continued

Structure: (CH3)2NCH2-[4-methylthiophen-2,5-diyl]-CH2SCH2CH2NHC(=CHNO2)NHCH2CHR2(OH)

| R² | R² | R² |
|---|---|---|
| 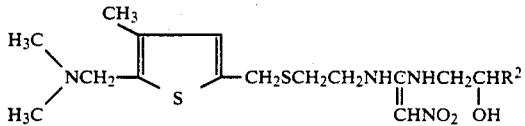 2-OCH3-phenyl | 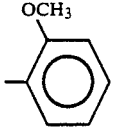 2,4-(OCH3)2-phenyl | 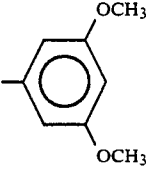 3-F-phenyl |
| 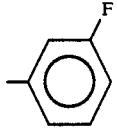 2-F-phenyl | 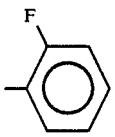 4-Cl-phenyl | 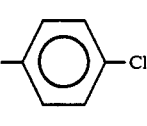 2,3,4-(OCH3)3-phenyl |
| 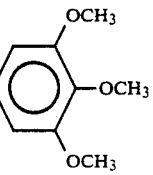 2-Cl-phenyl | 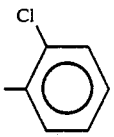 4-CH3-phenyl | 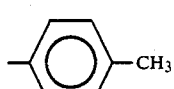 2-CH3-phenyl |
| 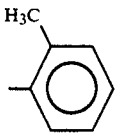 3,4-methylenedioxyphenyl | 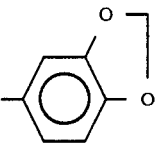 2,3-F2-phenyl | 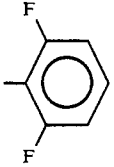 2,4-F2-phenyl |
| 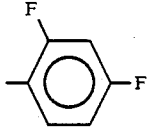 2-CH3-4-F-phenyl | 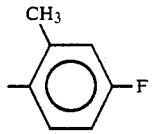 2-thienyl | 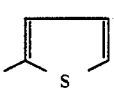 2-furyl |
| 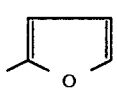 3-methyl-2-thienyl | 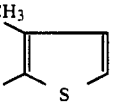 3-pyridyl | 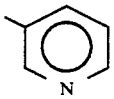 3-CN-phenyl |
| 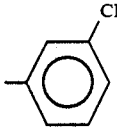 3,4-(OCH3)2-phenyl | 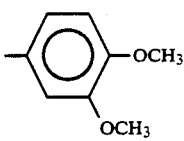 3-CH2CH3-phenyl | 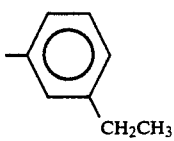 4-SO2CH3-phenyl |
| 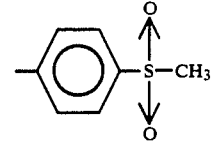 3-NO2-phenyl | 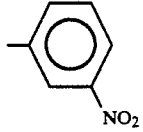 4-N(CH3)2-phenyl | 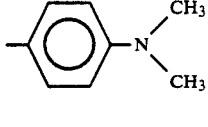 4-CH2CH2CH3-phenyl |
| 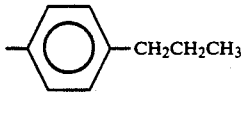 4-SCH3-phenyl | 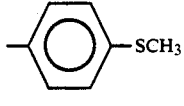 4-S(O)CH3-phenyl | |

The physical properties of these compounds were identical with those in Example 2.

TABLE 16

[Structure: piperidine-N—CH₂—(phenyl)—OCH₂CH₂CH₂NHCNHCH₂CH—R²  with =CHNO₂ and OH groups]

| R² | R² | R² |
|---|---|---|
| 4-F-phenyl | phenyl | 2-OCH₃-phenyl |
| 2-OCH₃-phenyl | 2,6-di-F-phenyl | 2,5-di-F-phenyl |
| 2,5-di-F-phenyl | 2-CH₃-4-F-phenyl | 2-F-phenyl |
| 2-thienyl | 2-furyl | 2-OH-phenyl |
| 4-OCH₃-phenyl | 4-CH₃-phenyl | indanyl |
| 3,4-methylenedioxyphenyl | 4-CH₂CH₃-phenyl | 3-Cl-phenyl |
| 3-pyridyl | 4-Cl-phenyl | 3-CH₃-phenyl |
| 3-CH₃-2-thienyl | 4-OH-phenyl | 4-NO₂-phenyl |
| 2-F-phenyl | 3-NH₂-phenyl | 4-C(O)NH₂-phenyl |

TABLE 16-continued
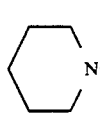
| R² | R² | R² |
|---|---|---|
| 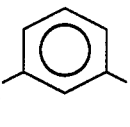 | 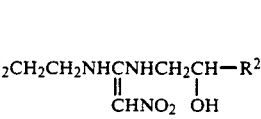 | 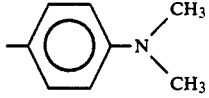 |
| 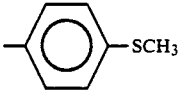 | 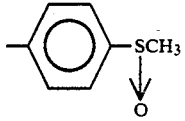 | 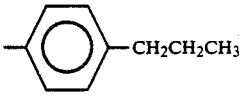 |
| 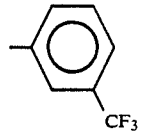 | | |
The physical properties of these compounds were identical with those in Example 10.
EXAMPLE 25
In the same manner as in Example 5, 7, 8 or 9, the corresponding starting materials were subjected to reaction, to obtain the objective compounds shown in Tables 17 and 18.
TABLE 17
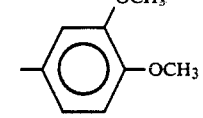
| R² | R² | R² |
|---|---|---|
| 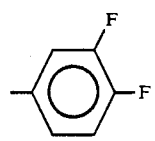 | 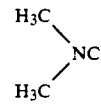 | 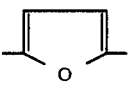 |
| 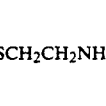 | 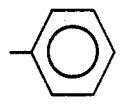 | 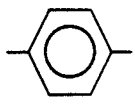 |
| 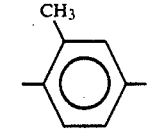 | 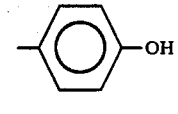 | 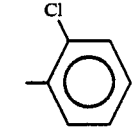 |
| 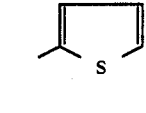 | 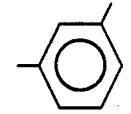 | 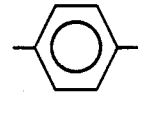 |

TABLE 17-continued

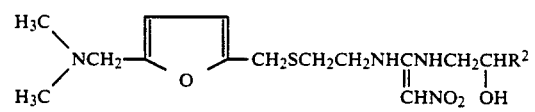

| R² | R² | R² |
|---|---|---|
| 4-methoxyphenyl | 4-ethylphenyl | furan-2-yl |
| 2-methoxyphenyl | 3,4-methylenedioxyphenyl | pyridin-3-yl |
| 4-fluorophenyl | 2,6-difluorophenyl | 2-methylpyridin-... |
| 3-fluorophenyl | 2,4-difluorophenyl | pyridin-4-yl |
| 2-fluorophenyl | 2,4-difluorophenyl | 4-cyanophenyl |
| 4-(hydroxymethyl)phenyl | 4-ethoxyphenyl | 4-(methylthio)phenyl |
| 4-(methylsulfinyl)phenyl | 4-propylphenyl | 3-(trifluoromethyl)phenyl |
| 2,3-dimethoxyphenyl | 3,4-difluorophenyl | |

The physical properties of these compounds were identical with those in Example 1.

TABLE 18

Structure:
(CH3)2N-CH2-[4-methyl-thiophene-2,5-diyl]-CH2SCH2CH2NHC(=CHNO2)NHCH2CH(OH)R²

TABLE 18-continued

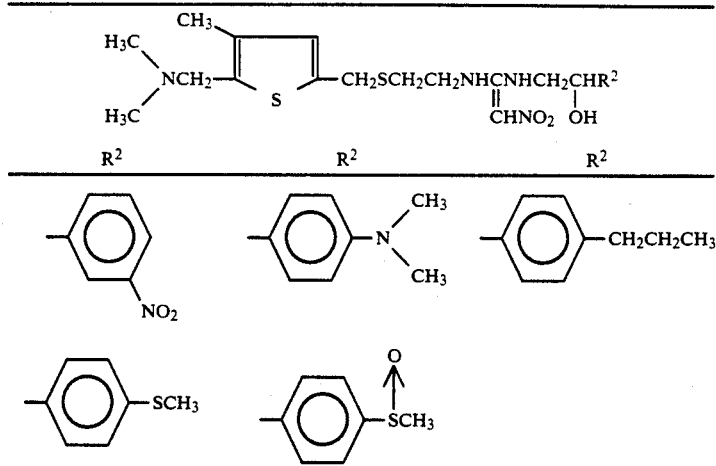

The physical properties of these compounds were identical with those in Example 2.

PREPARATION EXAMPLE 1

| | |
|---|---|
| N-[2-(4-fluorophenyl)-2-hydroxyethyl]-2-nitro-N'-[3-(3-piperidinomethylphenoxy)-propyl]-1,1-ethenediamine (Drug No. 15) | 20 mg |
| Corn starch | 25 mg |
| Crystalline cellulose | 18 mg |
| Lactose | 100.7 mg |
| Magnesium stearate | 1.3 mg |
| per tablet | 165 mg |

Tablets were prepared with the above recipe by a conventional method.

PREPARATION EXAMPLE 2

| | |
|---|---|
| N-{2-[[5-(dimethylamino)methyl-2-furyl]-methylthio]ethyl}-N'-[2-hydroxy-2-(4-hydroxyphenyl)ethyl]-2-nitro-1,1-ethenediamine (Drug No. 3) | 20 mg |
| Lactose | 278 mg |
| Corn starch | 60 mg |
| Magnesium stearate | 2 mg |
| per capsule | 360 mg |

Capsules were prepared with the above recipe by a conventional method.

PREPARATION EXAMPLE 3

As in Preparation Examples 1 and 2, tablets or capsules of each of Drug Nos. 4, 22, 29 and 32 were prepared.

What is claimed is:

1. An amine compound represented by the formula:

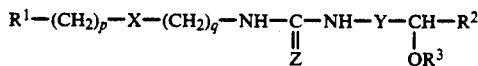

or a pharmaceutically acceptable salt thereof, wherein $R^1$ represents a phenyl, naphthyl, indanyl, thienyl or furyl group which may optionally be substituted by at least one substituent selected from the group consisting of halogen, hydroxyl, nitro, oxo, cyano, carboxyl, carbamoyl, mercapto, amino, $C_{1-8}$alkyl, $C_{2-4}$alkenyl, $C_{1-4}$alkoxy, $C_{1-4}$alkylthio, $C_{1-4}$alkylsulfinyl, $C_{1-4}$alkylsulfonyl, methylthiomethyl, ethylthiomethyl, methylthioethyl, methylsulfinylmethyl, ethylsulfinylmethyl, methylsulfinylethyl, methylsulfonylmethyl, ethylsulfonylmethyl, methylsulfonylethyl, hydroxy-$C_{1-4}$alkyl, $C_{2-4}$alkenyloxy, $C_{1-4}$alkoxy-$C_{1-4}$alkyl, 2-hydroxyethoxy, 3-hydroxypropoxy, halogeno-$C_{1-4}$alkyl, $C_{1-4}$alkylamino, di-$C_{1-4}$alkylamino, formyl, $C_{2-5}$alkanoyl, $C_{5-8}$cycloalkanecarbonyl, formyloxy-$C_{1-4}$alkyl, $C_{2-5}$alkanoyloxy-$C_{1-4}$alkyl, $C_{5-8}$cycloalkanecarbonyloxy-$C_{1-4}$alkyl, Benzoyloxy-$C_{1-4}$alkyl, toluoyloxy-$C_{1-4}$alkyl, 2-naphthoyloxy-$C_{1-4}$-alkyl, $C_{3-7}$cycloalkyl, phenyl, naphthyl, indanyl, benzyl, phenethyl, naphthylmethyl,

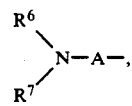

wherein $R^6$ and $R^7$ which may be the same or different, represent hydrogen, $C_{1-8}$alkyl, $C_{3-7}$cycloalkyl, $C_{2-4}$alkenyl, benzyl, phenethyl, napthylmethyl, hydroxyl, halogeno-$C_{1-4}$alkyl, hydroxy-$C_{1-4}$alkyl, $C_{1-4}$alkoxy-$C_{1-4}$alkyl, amino-$C_{1-4}$alkyl, $C_{1-4}$alkylamino-$C_{1-4}$alkyl or di-$C_{1-4}$alkylamino-$C_{1-4}$alkyl, and A is a $C_{1-4}$alkylene, or $R^6$ and $R^7$ may be bonded together forming a nitrogen-containing saturated heterocycle thereby forming a ring selected from the group consisting of 1-pyrrolidinyl, piperidino, 3-hydroxy-1-pyrrolidinyl, 3-hydroxymethyl-1-pyrrolidinyl, 2-hydroxymethyl-1-pyrrolidinyl, 3-hydroxy-1-piperidinyl, 4-hydroxy-1-piperidinyl, 3-hydroxymethyl-1-piperidinyl, and 4-hydroxymethyl-1-piperidinyl; p is 0, 1, 2 or 3; X is an oxygen or sulfur atom; q is 2, 3 or 4; Z is oxygen, sulfur, $NR^4$ wherein $R^4$ is formyl, $C_{2-5}$alkanoyl, $C_{5-8}$cycloalkanecarbonyl, benzoyl, toluoyl, 2-naphthoyl, phenyl, naphthyl, indanyl, benzenesulfonyl, naphthalenesulfonyl, phenyloxy, naphthyloxy, formylamino, $C_{2-5}$alkanoylamino, $C_{5-8}$cycloalkanecarbonylamino, benzoylamino, toluoylamino, 2-naphthoylamino, each of which may optionally be substituted by at least one substituent selected from the group consisting of $C_{1-8}$alkyl, halogen-$C_{1-4}$alkyl, $C_{1-4}$alkoxy and halogen, or hydrogen, cyano, hydroxyl, nitro, $C_{1-8}$alkyl, $C_{2-4}$-alkenyl, $C_{1-4}$alkoxy, carbamoyl, sulfamoyl, $C_{1-4}$alkoxycarbonyl, $C_{1-4}$alkylsulfonyl, $C_{1-4}$alkoxycarbonylamino or carboxy-$C_{1-4}$alkylamino; Y is $C_{1-4}$alkylene; $R^2$ is phenyl, indanyl, thienyl or furyl which may be optionally be substituted by at least one substituent selected from the group consisting of halogen, hydroxyl, nitro, amino, hydroxy-$C_{1-4}$alkyl, cyano, $C_{1-8}$alkyl, $C_{1-4}$alkoxy, $C_{1-4}$alkylthio, $C_{1-4}$alkylsulfinyl, $C_{1-4}$alkylsulfonyl, halogeno-$C_{1-4}$alkyl, di-$C_{1-4}$alkylamino, carbamoyl, or $C_{2-5}$alkanoyl, and $R^3$ is a hydrogen or hydroxyl-protecting group selected from the group consisting of formyl, $C_{2-5}$alkanoyl, $C_{5-8}$cycloalkanecarbonyl, benzoyl, toluoyl, 2-naphthoyl, 2-phenoyl, 3-furoyl, nicotinoyl, 1,1-dimethylpropoxycarbonyl, t-butoxycarbonyl, isopropoxycarbonyl, 2,2,2-trichloroethoxycarbonyl, ethoxycarbonyl, 2,2,2-tribromoethoxycarbonyl, benzyloxycarbonyl, 4-nitrobenzyloxycarbonyl, 4-brmobenzyloxycarbonyl, 4-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, monochloroacetyl, trifluoroacetyl, 2-furfuryloxycarbonyl, 1-adamantyloxycarbonyl, 8-quinolyloxycarbonyl, benzyl, diphenylmethyl, trityl, $C_{1-8}$alkyl, methoxymethyl, tetrahydrofuryl, tetrahydropyranyl, 2-nitrophenylthio, 2,4-dinitrophenylthio, trimethylsilyl and t-butyldimethylsilyl.

2. The amine compound of claim 1, wherein $R^1$ is phenyl, indanyl, thienyl or furyl or one of these groups substituted by one of the substituents of claim 1.

3. The amine compound of claim 2, wherein the substituent on $R^1$ is a member selected from the group consisting of halogen, hydroxyl, nitro, amino, hydroxy-$C_{1-4}$alkyl, cyano, $C_{1-8}$alkyl, $C_{1-4}$alkoxy, $C_{1-4}$alkylthio, $C_{1-4}$alkylsulfinyl, $C_{1-4}$alkylsulfonyl, halogeno-$C_{1-4}$alkyl, di-$C_{1-4}$alkylamino and carbamoyl.

4. The amine compound of claim 3, wherein Z is oxygen, $C_{1-4}$alkylsulfonylimino, benzenesulfonylimino, naphthalenesulfonylimino, cyanoimino or sulfamoylimino.

5. An amine compound of the formula:

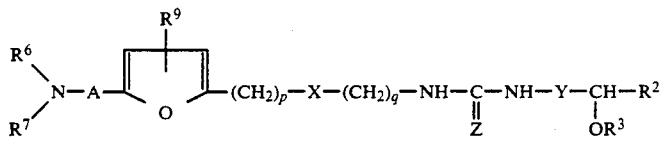

wherein $R^9$ is a hydrogen or $C_{1-8}$ alkyl group and $R^2$, $R^3$, $R^6$, $R^7$, A, p, q, X, Y and Z have the same meanings as defined in claim 1, or a pharmaceutically acceptable salt thereof.

6. An amine compound of the formula:

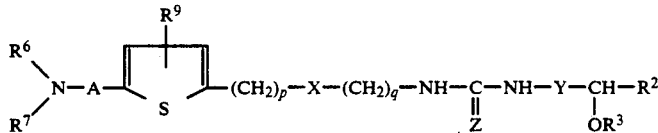

wherein $R^9$ is a hydrogen or $C_{1-8}$alkyl group, and $R^2$, $R^3$, $R^6$, $R^7$, A, p, q, X, Y and Z have the same meanings as defined in claim 1, or a pharmaceutically acceptable salt thereof.

7. An amine compound of the formula:

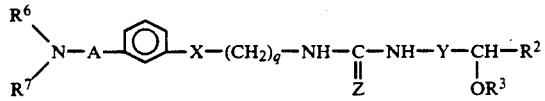

wherein $R^2$, $R^3$, $R^6$, $R^7$, A, q, X, Y and Z have the same meanings as defined in claim 1, or a pharmaceutically acceptable salt thereof.

8. The amine compound as in any preceding claim, wherein Y is methylene.

9. The amine compound as in any one of claims 1 to 7, wherein $R^3$ is hydrogen.

10. The amine compound as in any ne of claims 1 to 7, wherein $R^3$ is one of the hydroxyl-protecting groups set forth in claim 1.

11. An amine compound represented by the formula:

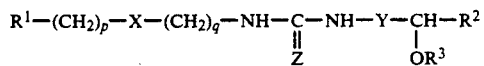

or a pharmaceutically acceptable salt thereof, wherein $R^1$ represents a phenyl, naphthyl, indanyl, thienyl or furyl group which may optionally be substituted by at least one substituent selected from the group consisting of halogen, hydroxyl, nitro, oxo, cyano, carboxyl, carbamoyl, mercapto, amino, $C_{1-8}$alkyl, $C_{2-4}$alkenyl, $C_{1-4}$alkoxy, $C_{1-4}$alkylthio, $C_{1-4}$alkylsulfinyl, $C_{1-4}$alkylsulfonyl, methylthiomethyl, ethylthiomethyl, methylthioethyl, methylsulfinylmethyl, ethylsulfinylmethyl, methylsulfinylethyl, methylsulfonylmethyl, ethylsulfonylmethyl, methylsulfonylethyl, hydroxy-$C_{1-4}$alkyl, $C_{2-4}$alkenyloxy, $C_{1-4}$alkoxy-$C_{1-4}$alkyl, 2-hydroxyethoxy, 3-hydroxypropoxy, halogeno-$C_{1-4}$alkyl, $C_{1-4}$alkylamino, di-$C_{1-4}$alkylamino, formyl, $C_{2-5}$alkanoyl, $C_{5-8}$cycloalkanecarbonyl, formyloxy-$C_{1-4}$alkyl, $C_{2-5}$alkanoyloxy-$C_{1-4}$alkyl, $C_{5-8}$cycloalkanecarbonyloxy-$C_{1-4}$alkyl, benzoyloxy-$C_{1-4}$alkyl, toluoyloxy-$C_{1-4}$alkyl, 2-naphthoyloxy-$C_{1-4}$alkyl, $C_{3-7}$cycloalkyl, phenyl, naphthyl, indanyl, benzyl, phenethyl, naphthylmethyl,

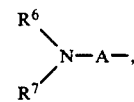

wherein $R^6$ and $R^7$, which may be the same or different, represent hydrogen, $C_{1-8}$alkyl, $C_{3-7}$cycloalkyl, $C_{2-4}$alkenyl, benzyl, phenethyl, naphthylmethyl, hydroxyl, halogeno-$C_{1-4}$alkyl, hydroxy-$C_{1-4}$alkyl, $C_{1-4}$alkoxy-$C_{1-4}$alkyl, amino-$C_{1-4}$alkyl, $C_{1-4}$alkylamino-$C_{1-4}$alkyl or di-$C_{1-4}$alkylamino-$C_{1-4}$alkyl, and A is a $C_{1-4}$alkylene; p is 0, 1, 2, 3; X is an oxygen or sulfur atom; q is 2, 3 or 4; Z is oxygen, sulfur or $NR^4$ wherein $R^4$ is formyl, $C_{2-5}$alkanoyl, $C_{5-8}$cycloalkanecarbonyl, benzoyl, toluoyl, 2-naphthoyl, phenyl, naphthyl, indanyl, benzenesulfonyl, naphthalenesulfonyl, phenyloxy, naphthyloxy, formyamino, $C_{2-5}$-alkanoylamino, $C_{5-8}$cycloalkanecarbonylamino, benzoylamino, toluoylamino, 2-naphthoylamino, each of which may optionally be substituted by at least one substituent selected from the group consisting of $C_{1-8}$alkyl, halogeno-$C_{1-4}$alkyl, $C_{1-4}$alkoxy and halogen, or hydrogen, cyano, hydroxyl, nitro, $C_{1-8}$alkyl, $C_{2-4}$alkenyl, $C_{1-4}$alkoxy, carbamoyl, sulfamoyl, $C_{1-4}$alkoxycarbonyl, $C_{1-4}$alkylsulfonyl, $C_{1-4}$alkoxycarbonylamino or carboxy-$C_{1-4}$alkylamino; Y is $C_{1-4}$alkylene; $R^2$ is phenyl, indanyl, thienyl or furyl group which may optionally be substituted by at least one substituent selected from the group consisting of halogen, hydroxyl, nitro, amino, hydroxy-$C_{1-4}$alkyl, cyano, $C_{1-8}$alkyl, $C_{1-4}$alkoxy,$C_{1-4}$alkylthio, $C_{1-4}$alkylsulfinyl, $C_{1-4}$alkylsulfonyl, halogeno-$C_{1-4}$alkyl, di-$C_{1-4}$alkylamino, carbamoyl, or $C_{1-4}$alkanoyl, and $R^3$ is a hydrogen or hydroxyl-protecting group selected from the group consisting of formyl, $C_{2-5}$alkanoyl, $C_{5-8}$cycloalkanecarbonyl, benzoyl, toluoyl, 2-naphthoyl, 2-thenoyl, 3-furoyl, nicotinoyl, 1,1-dimethylpropoxycarbonyl, t-butoxycarbonyl, isopropoxycarbonyl, 2,2,2-trichloroethoxycarbonyl, ethoxycarbonyl, 2,2,2-tribromoethoxycarbonyl, benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl 4-(phenylazo)-benzyloxycarbonyl, 4-(4-methoxyphenylazo)benzyloxycarbonyl, monochloroacetyl, trifluoroacetyl, 2-furfuryloxycarbonyl, 1adamantyloxycarbonyl, 8-quinolyloxycarbonyl, benzyl, diphenylmethyl, trityl, $C_{1-8}$alkyl, methoxymethyl, tetrahydrofuryl, tetrahydropyranyl, 2-nitrophenylthio, 2,4-dionitrophenylthio, trimethylsilyl and t-butyldimethylsilyl.

12. The amine compound of claim 1, wherein $R^4$ is $C_{1-4}$alkylsulfonyl.

13. The amine compound of claim 12, wherein the $C_{1-4}$alkylsulfonyl is methylsulfonyl.

14. The amine compound of claim 11, wherein $R^{4\ l\ is}$ $C_{1-4}$alkylsulfonyl.

15. The amine compound of claim 14, wherein the $C_{1-4}$alkylsulfonyl is methylsulfonyl.

16. N-($\beta$-hydroxyphenethyl)-N'-methanesulfonyl-N''-[3-(3-piperidinomethylphenoxy)propyl]guanidine or a pharmaceutically acceptable salt thereof.

17. An anti-ulcer composition comprising a pharmaceutically effective amount of the amine compound or a pharmaceutically acceptable salt thereof according to any one of the claims 4 and 5 to 16.

18. A method for treating mammals or human beings having ulcers, which comprises administering to said mammal a therapeutically effective amount of the amine compound or pharmaceutically acceptable salt thereof according to any one of claims 1 to 16.

* * * * *